(12) United States Patent
Tanaka et al.

(10) Patent No.: US 8,182,846 B2
(45) Date of Patent: May 22, 2012

(54) PLANT EXTRACTS AND USES THEREOF

(75) Inventors: Akiko Tanaka, St. Petersburg, FL (US);
William Guy Bradley, St. Petersburg, FL (US)

(73) Assignee: Tampa Bay Research Institute, Inc., St. Peterburg, FL (US)

( * ) Notice: Subject to any disclaimer, the term of this patent is extended or adjusted under 35 U.S.C. 154(b) by 0 days.

(21) Appl. No.: 12/950,414

(22) Filed: Nov. 19, 2010

(65) Prior Publication Data

US 2011/0064771 A1 Mar. 17, 2011

Related U.S. Application Data

(60) Continuation of application No. 11/557,019, filed on Nov. 6, 2006, now Pat. No. 7,838,046, which is a continuation-in-part of application No. 11/010,663, filed on Dec. 13, 2004, now Pat. No. 7,338,676, which is a division of application No. 09/964,240, filed on Sep. 26, 2001, now Pat. No. 6,866,875.

(51) Int. Cl.
*A61K 36/00* (2006.01)
*A61K 36/15* (2006.01)
*A61K 45/00* (2006.01)

(52) U.S. Cl. .................................... 424/725; 424/278.1

(58) Field of Classification Search ....................... None
See application file for complete search history.

(56) References Cited

FOREIGN PATENT DOCUMENTS

SU 301148 A * 3/1972

* cited by examiner

*Primary Examiner* — Qiuwen Mi
(74) *Attorney, Agent, or Firm* — Innovus Law Group; Thomas E. Toner

(57) ABSTRACT

Plant extracts obtainable by extracting various plant materials with an alkaline agent, methods for preparing such extracts, compositions comprising such extracts, and methods for using the extracts or compositions thereof are described.

4 Claims, 44 Drawing Sheets

Loquat, Black tea and japanese black pine combo

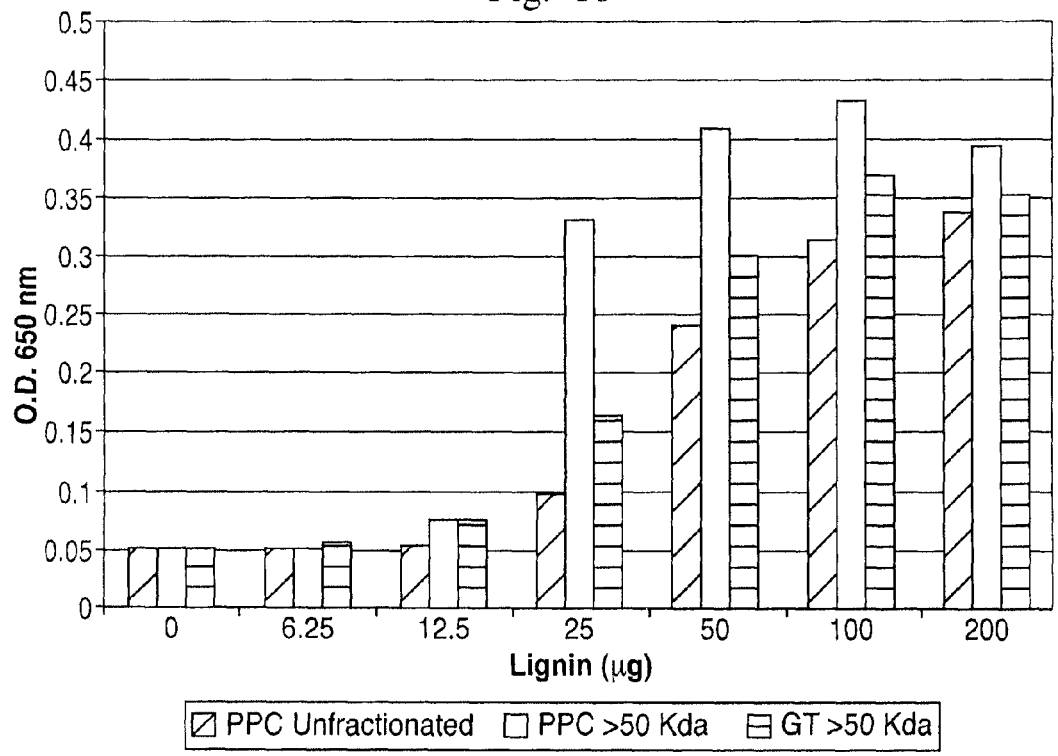

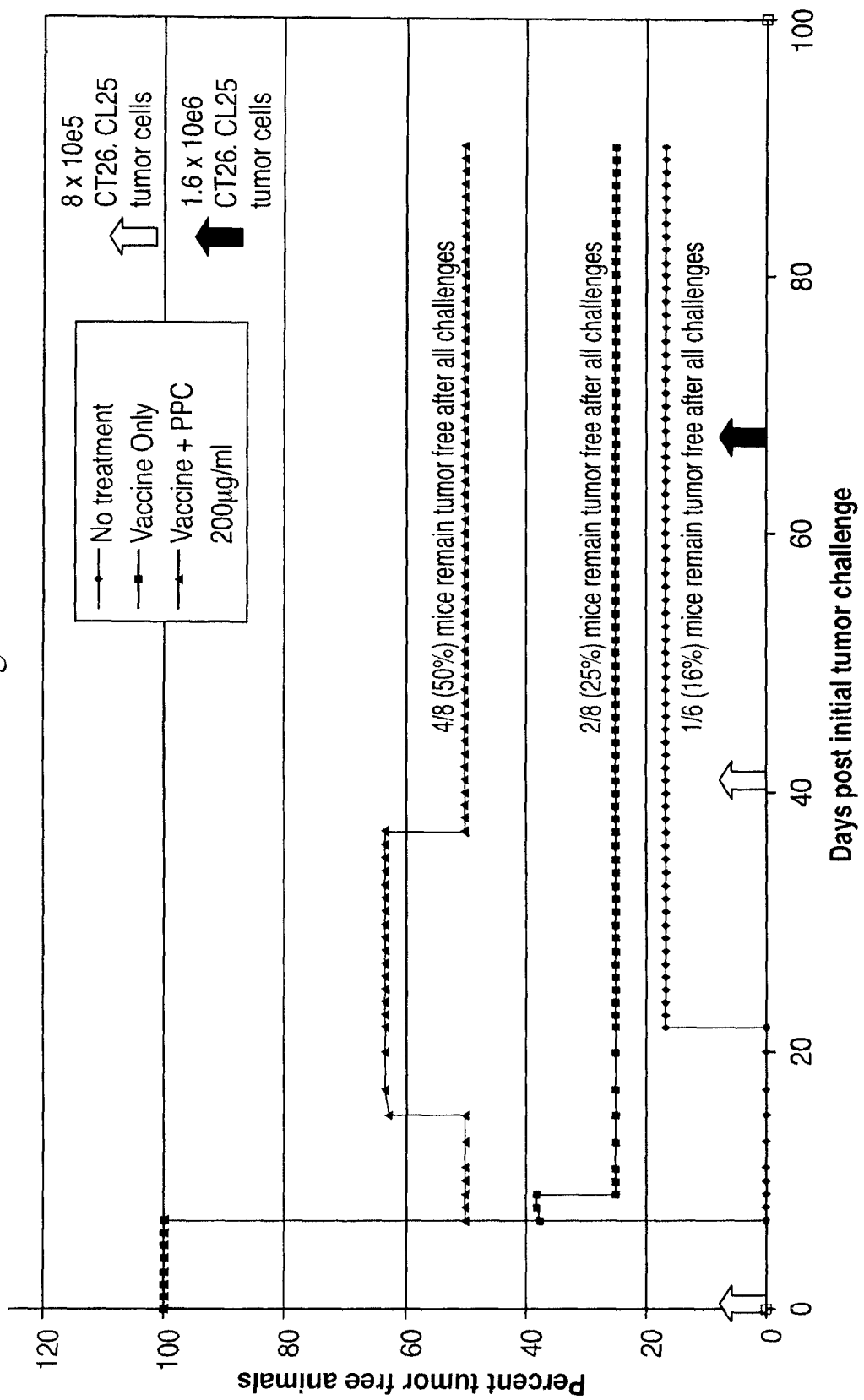

PLANT EXTRACTS AND USES THEREOF

CROSS REFERENCE TO RELATED APPLICATIONS

This application is a continuation of U.S. patent application Ser. No. 11/557,019, issued as U.S. Pat. No. 7,838,046, filed Nov. 6, 2006 which is a continuation-in-part of U.S. patent application Ser. No. 11/010,663 now U.S. Pat. No. 7,338,676 filed Dec. 13, 2004, which is a divisional of U.S. patent application Ser. No. 09/964,240 filed Sep. 26, 2001 (issued on Mar. 15, 2005 as U.S. Pat. No. 6,866,875), the entire disclosures of which are hereby incorporated by reference.

FIELD OF THE INVENTION

The present invention relates generally to preparation of alkaline extracts obtainable, for example, by extracting a variety of plants cells with a solution comprising an alkaline agent, to the alkaline extracts themselves, to compositions containing the alkaline extracts, and to uses thereof.

BACKGROUND OF THE INVENTION

As researchers gain an increased understanding of the vertebrate immune system, methods to harness and specifically employ the immune system in preventing and fighting of illnesses are constantly being sought. Because of the immune system's extraordinary versatility, this approach, in principle, offers the possibility to react on any substance of sufficient size. Numerous attempts have been made to establish vaccination and/or immunological treatment methods of cancer, bacterial and viral infections.

Vaccination methods commonly employ exposing the organism to be vaccinated to vaccine preparations of an antigenic substance in order to generate an immune response. Particularly, the antigenic substance (antigen) is used to initiate production of immunoglobulins and/or cytotoxic phagocytic cells capable of detecting the antigenic substance itself or parts thereof (epitope), thereby becoming rapidly recognizable to the immune system. An antigen that has such an epitope becomes rapidly recognizable and can be inactivated or destroyed, e.g. by uptake into T cells and subsequent disintegration or by destruction of the cells comprising the antigen.

A similar method of vaccination or treatment is to extract lymphocytes, particularly lymphocyte stem cells, from the organism to be treated, exposing the extracted cells to the antigen, thus inducing production of immunoglobulins capable of detecting the antigen, and then reintroducing the immunoglobulin-producing lymphocytes into the organism to be treated (ex vivo treatment).

There are two general types of immune responses that contribute to the eradication of microbial infections and tumors. These are referred to as innate (natural, non-specific) and adaptive (acquired, specific) immune responses. Recently, several studies have demonstrated innate and adaptive immunity are linked in a variety of ways. Many types of adaptive immune responses are not successful in the absence of the appropriate collaborative innate stimulus.

In human peripheral blood, there are two subsets of professional antigen presenting cells (APC) that are the central coordinators of adaptive T cell responses. These are plasmacytoid (also called natural Interferon producing cells) dendritic cells (pDC) and myeloid dendritic cells (mDC). Both of these dendritic cell (DC) subsets express members of the Toll-like Receptor (TLR) family of pattern recognition receptors, so-called for their ability to bind conserved structural components of various microbes. Binding of such structures by TLRs initiates a signal transduction pathway that activates the DC for antigen presentation. During viral infections, pDCs activate mDCs by producing type I interferons (IFN-alpha) in response to ssRNA detected by the TLR8 pathway. Myeloid DCs derived from monocytes stimulated with the cytokines GM-CSF and IL4 can produce IL12 in response to bacterial structures such as lipopolysaccharide (LPS) and dsRNA via TLR4 and TLR3, respectively. Neither pathway is believed to result in the production of type I interferons in mDCs.

An important discovery has been the definition of tumor associated antigens (TAA) recognized by human T lymphocytes. The identification and molecular characterization of TAA is widely believed to have provided the means to create cancer vaccines. Current efforts in the creation of such vaccines are based on nucleic acid mediated immunization techniques, i.e. insertion of one or more antigen coding sequences (e.g. a TAA encoding sequence) into suitable expression (host) vectors capable of causing expression of the antigen coding sequence directly within transfected cells.

Commonly employed host vectors are bacteria and viruses or bacterial and viral genomes, respectively. Recent studies have shown that a cellular or encapsulated vector is not always necessary for vaccine preparation. Immunization with "naked" plasmid DNA and/or with RNA (e.g. with the nucleic acid being devoid of any other structural components such as proteins, lipids, or carbohydrates) can elicit powerful cellular and antibody responses. Nucleic acid vaccines, also termed recombinant vaccines, are thus vaccines in which the genome of the host vector integrates a nucleic acid sequence coding for an immunogen (antigen).

Compared to cell-based vaccines or cell lysates, recombinant vaccines have multiple advantages, the most prominent is probably that they can focus the immune response against a single, specific antigen like a TAA, and thus limit the possibility of releasing an uncontrolled autoimmune aggression against hitherto unknown antigens being present in normal tissues and tumor cells.

Currently, vaccination and therapeutic success vary greatly for different ailments and even among patients treated for the same ailment. Furthermore, vaccination does not always have satisfactory duration of effect, but can wear off within weeks. These drawbacks hold true also for a number of other vaccination methods, which may involve administration of live or inactivated vaccines. In general, vaccines are not always able to generate an appropriate and effective immune response by themselves.

Certain substances, when administered simultaneously with a specific antigen, will enhance the immune response to that antigen. Such substances, known as adjuvants, are routinely included in inactivated or purified antigen vaccines. Examples of adjuvants in common use are aluminium salts, liposomes and immunostimulating complexes (ISCOMS), complete and incomplete Freund's adjuvant, muramyl dipeptide and cytokines like interleukin (IL) 2, IL-12 and interferon (IFN) gamma.

Yet, while some adjuvants are suited for combination with some antigens or vaccines, they may fail in other combinations, or they may be toxic themselves to vertebrates like humans, promote poor cell mediated immunity, they may be unstable or too expensive and/or cumbersome to prepare. Improved methods for vaccination and treatment of illnesses and ailments in vertebrates are therefore needed.

Under certain circumstances, it is advantageous to boost patient's immune system without subsequent vaccination of the patient against a particular antigen. For example, patients suffering from diabetes have weakened immune responses that make them prone to different ailments, e.g. pneumonia or cancer. Patients with weakened immune responses will benefit greatly from development of medicaments that strengthen patients' immune system and improve patients' immune responses.

Generation of specific cell types, e.g. for tissue transplant purposes, is frequently needed. Among the cell types that can be used are dendritic cells and recently discovered fibrocytes.

Dendritic cells are potent antigen presenting cells. They are also reported to act as stimulators of a mixed lymphocyte reaction, to migrate selectively through tissues, to take up, process and present antigens, and serve as passenger cells that elicit rejection of transplanted tissues. For a review see for example Hart D N J "Dendritic cells: unique leukocyte populations which control the primary immune response", Blood, 1997, 90:3245-3287. The study of dendritic cells offers potential applications in any field where the correct recognition of antigens and generation of immune responses is desirable. Such fields are, for example, transplantation medicine, vaccination, therapy of cancer and other illnesses connected with antigen presentation, prevention and treatment of autoimmune diseases and the like, see for example Dallal R M and Lotze M T, "Dendritic cells and human cancer vaccines", Current Opinion in Immunology, 2000, 12:583-588. However, understanding of dendritic cells and their differentiation is insufficient. It is desirable to have methods for producing dendritic cells.

Current protocols for the production of dendritic cells rely on their differentiation from peripheral blood mononuclear cells, bone marrow cells or other $CD34^+$ cells by exposing such cells to multiple cytokine combinations including granulocyte-macrophage colony stimulating factor (GM-CSF), stem cell factor (SCF), tumor necrosis factor alpha (TNFα), tumor growth factor beta (TGFβ) and IL-4. For a review see for example Strunk, D. et al., "Generation of human dendritic cells/Langerhans cells from circulating CD34+ hematopoietic progenitor cells", Blood, 1996, 87:1292-1302 and Soligo, D. et al., "Expansion of dendritic cells derived from human $CD34^+$ cells in static and continuous perfusion cultures", British Journal of Hematology, 1998, 101:352-363. Likewise, dendritic cells have been produced from $CD14^+$ blood monocytes and different maturation stages have been described. For a review see Winzler, C. et al., "Maturation stages of mouse dendritic cells in growth factor-dependent long-term cultures", Journal of Experimental Medicine, 1997, 185:317-328 and U.S. Pat. No. 6,194,204 to Crawford and Chester. Yet, present protocols rely on expensive and unstable cytokine media components. Likewise, the yield of present protocols for the production of dendritic cells is often considered unsatisfactorily low and improvement in this area is needed.

Fibrocytes are a recently described type of cell characterized by their distinct phenotype (collagen+, $CD34^+$), which normally is also vimetin$^+$, $CD13^+$ and $CD45^+$. They are reported to enter rapidly from blood into subcutaneously implanted wound chambers. They are also frequently present in connective tissue scars and may play an important role in wound repair and pathological fibrotic responses. For a review see for example Bucala, R. et al., "Circulating fibrocytes define a new leukocyte subpopulation that mediates tissue repair", Mol. Med. 1994, 1:71-81, and Chesney J and Bucala R, "Peripheral blood fibrocytes: novel fibroblast-like cells that present antigen and mediate tissue repair", Biochemical Society Transactions, 1997, 25:520-4. Like dendritic cells, protocols for the production of fibrocytes rely on expensive and unstable cytokine media components and provide often unsatisfactorily low yields and improvements in this area are likewise needed.

Serum amyloid P component (SAP) is a member of the pentraxin family of proteins (Bharadwaj et al., J. Immunology, 2001 166: 6735-6741). These proteins are characterized by cyclic pentameric structure, calcium-dependent ligand binding, and frequent regulation as acute-phase serum proteins. SAP is the serum precursor of the P component of amyloid. It binds to a broad group of molecules, including autoantigens, through a pattern recognition binding site. The related pentraxin, C-reactive protein (CRP), is a strong acute-phase reactant in man and an opsonin. CRP and SAP bind to leukocytes through Fc receptors for IgG (FcgammaR) (Bharadwaj et al., J. Immunology, 2001 166: 6735-6741).

Fc receptors (FcRs) are membrane receptors expressed on a number of immune effector cells. Upon interaction with target immunoglobulins, FcRs mediate a number of cellular responses, including, activation of cell mediated killing, induction of mediator release from the cell, uptake and destruction of antibody coated particles, and transport of immunoglobulins. Deo et al., 1997, *Immunology Today* 18:127-135. Further, it has been shown that antigen-presenting cells, e.g., macrophages and dendritic cells, undergo FcR mediated internalization of antigen-antibody complexes, allowing for antigen presentation and the consequent amplification of the immune response. As such, FcRs play a central role in development of antibody specificity and effector cell function. Deo et al., 1997, *Immunology Today* 18:127-135.

Each member of the Fc receptor family is defined by its specificity for a particular immunoglobulin isotype; Fc receptors for IgG antibodies are referred to as FcγR, for IgE as FcεR, and for IgA as FcαR. Three subclasses of human gamma receptors have been identified: FcγRI (CD64), FcγRII (CD32) and FcγRIII (CD16). Because each human FcγR subclass is encoded by two or three genes, and alternative RNA splicing leads to multiple transcripts, a broad diversity in Fcγ isoforms exists. The three genes encoding the human FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. FcRs are reviewed in Ravetch and Kinet, Annu. Rev. Immunol 9:457-92 (1991); Capel et al., Immunomethods 4:25-34 (1994); and de Haas et al., J Lab. Clin. Med. 126:330-41 (1995).

Because of the central role of FcγR as a trigger molecule in numerous immune responses, it has become a target for developing therapeutics. For example, several ongoing clinical trials are based on activating a cancer patient's effector cells by treating the patient with tumor-specific monoclonal antibodies (Mabs). These studies have shown that the tumor-specific antibodies mediate their effects in part through FcγR binding, and subsequent effector cell activity. (Adams et al., 1984, *Proc. Natl. Acad. Sci.* 81:3506-3510; Takahashi et al., 1995, *Gastroenterology* 108:172-182; Riethmeuller et al., 1994, *Lancet* 343:1177-1183, Clynes, R. A., Towers, T. L., Presta, L. G., and Ravetch, J. V., 2000, *Nature Med.* 6:443-446). Further, a novel series of bispecific molecule antibodies (BSMs), molecules engineered to have one arm specific for a tumor cell and the other arm specific for a target FcγR, are in clinical trials to specifically target a tumor FcγR mediated, effector cell destruction of the tumor cells. (Valone et al., 1995, *J. Clin. Oncol.* 13:2281-2292; Repp et al., 1995, *Hematother* 4:415-421). FcγRs can also be used as therapeutic targets in infectious diseases and autoimmune disorders (Deo et al., 1997, *Immunology Today* 18:127-135; Ierino et al., 1993, *J. Exp. Med.* 178:1617-1628; Debre et al., 1993, *Lancet* 342:945-949). There is currently an unmet need for non-toxic modulators of Fc R.

If one or more of the above problems or needs could be addressed, a significant advance in the art would result.

SUMMARY OF THE INVENTION

In one embodiment, the present invention provides a method for production of a composition (hereinafter referred to as an "alkaline extract") wherein the composition is prepared by alkaline extraction of one or more of a variety of plant materials. Such alkaline extracts represent further embodiments of the present invention.

In another embodiment, the present invention provides methods for enhancing or improving the immune response in a vertebrate subject, for example a mammal. In one embodiment, the method comprises the steps of increasing an amount of one or more immunogens in the vertebrate subject and administering to the vertebrate subject an alkaline extract of the invention.

In still another embodiment, the present invention provides methods for vaccination and/or treatment of mammalian subjects with an alkaline extract or compositions thereof. In other embodiments, the present invention provides alkaline extract compositions useful for enhancing and/or improving the immune response or for enhancing and/or improving effects of nucleic acid vaccines and medicaments.

In yet another embodiment, the present invention provides compounds having a UV spectrum as shown in any one of FIG. 1-2 or 9. In one embodiment, the compounds are in substantially pure (e.g. at least about 90% or at least about 95%) form. The present invention also provides pharmaceutical compositions comprising one or more compounds having a spectrum as shown in any one of FIG. 1-2 or 9, and one or more pharmaceutically acceptable excipients. In still another embodiment, the present invention provides pharmaceutical compositions comprising lignin or alkaline extracts as disclosed herein.

Compositions of the invention can be co-administered with vaccines or medicaments for immunotherapy according to embodiments of the invention. The term "co-administered" or "co-administration" herein refers to administration of two or more dosage forms or active ingredients. The two or more dosage forms or active ingredients can be administered substantially simultaneously or sequentially over a period of time, for example hours, days, weeks or months.

In another embodiment, the invention provides a kit for vaccination and/or therapy of vertebrates, wherein the kit comprises an alkaline extract of the invention, one or more vaccines, and optionally one or more adjuvants.

In other embodiments, the present invention provides methods for the preparation of cells with dendritic and/or fibrocyte-like phenotype. In still other embodiments, compositions of the invention are useful for inducing differentiation of a number of cell types into cells with a phenotype of immature and/or mature dendritic and/or fibrocyte cells. In yet another embodiment, the invention provides a method for producing phenotypically immature and/or mature dendritic and/or fibrocyte cells. Such methods can comprise exposing cells selected from the group consisting of blood mononuclear cells, thymocytes, splenocytes, umbilical cord blood cells, bone marrow cells, $CD34^+$-cells, $CD14^+$-cells or mixtures thereof to an effective amount of an alkaline extract as described herein.

In other embodiments, the present invention also provides methods for obtaining IFN-alpha-producing myeloid dendritic cells by incubating peripheral blood mononuclear cells with an alkaline extract, and methods of treating patients with the IFN-alpha producing myeloid dendritic cells.

These and other embodiments of the present invention are described in further detail hereinbelow.

BRIEF DESCRIPTION OF THE DRAWINGS

FIG. 9 shows spectra of alkaline extracts prepared from various plants.

FIG. 16 shows adherence of human PBMCs 48 hours after treatment with GTX or PPC (unfractioned and >50 kDa).

FIG. 26B shows the presences of a memory immune response following vaccination with a whole cell tumor vaccine and delivery of a pine cone alkaline extract.

DETAILED DESCRIPTION OF THE INVENTION

Figure 1:
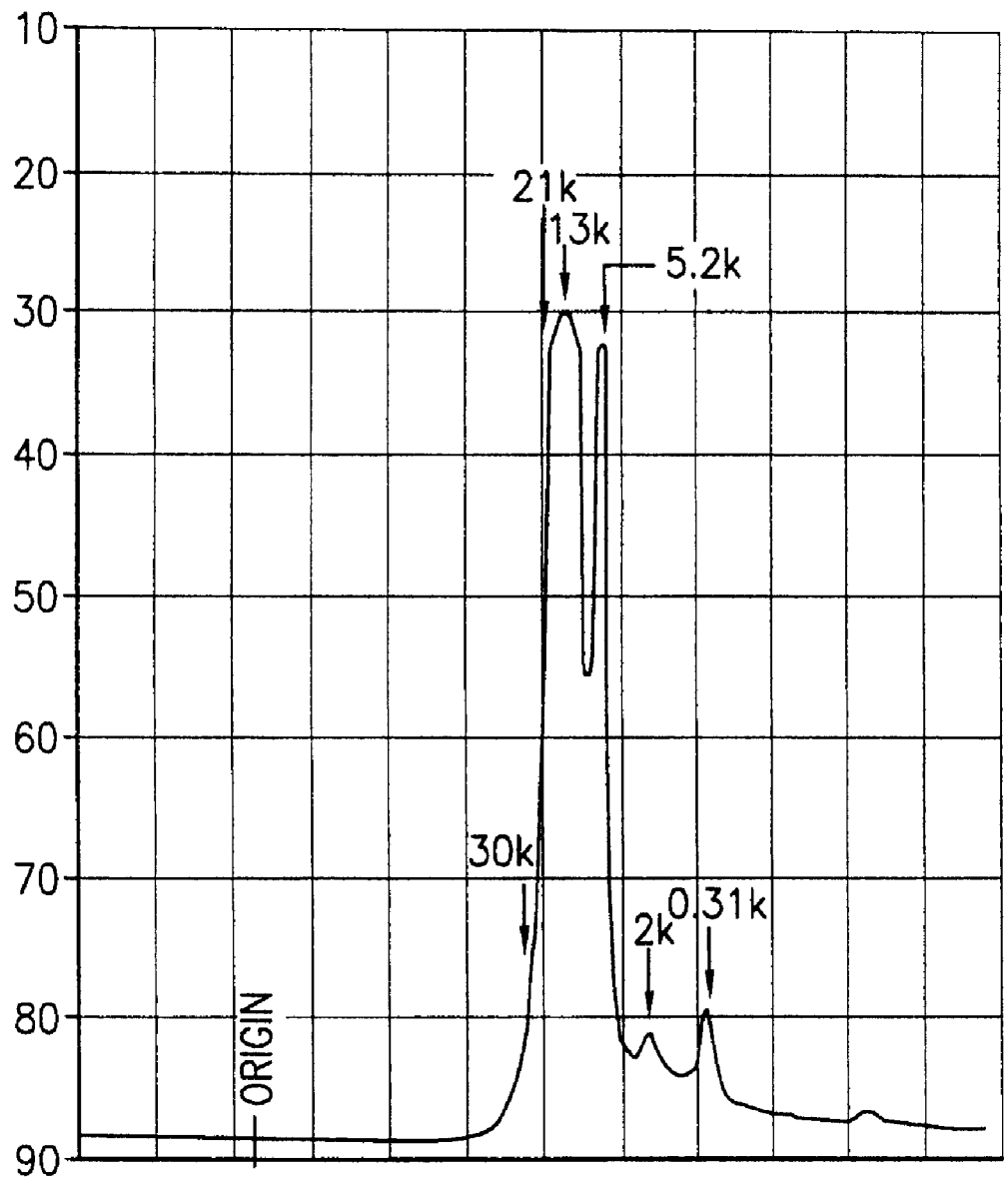
FIG. 1 shows fast protein liquid chromatography (FPLC) spectrum of a pine cone extract (also referred to as "PPC") extracted with potassium hydroxide of Phase 1, Example 1.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed thereby. This includes ranges that can be formed that do or do not include a finite upper and/or lower boundary. Accordingly, the skilled person will appreciate that many such ratios, ranges, and ranges of ratios can be unambiguously derived from the data and numbers presented herein and all represent embodiments of the present invention.

The term "vaccination" denotes treatments of vertebrates primarily to prevent disease or ailment by creating, enhancing or maintaining the immune system's capacity to respond to antigens correlated with the disease or ailment. The term "treatment" is the context of an immune disease or disorder denotes creating, enhancing or maintaining the immune system's capacity to respond to antigens correlated with a disease or ailment after the first onset of the disease or ailment, thus being therapeutic in nature. The active ingredient in a vaccination treatment is often termed "vaccine", whereas the active ingredient in a therapeutic treatment is often termed a "medicament" or "compound". These terms can be used interchangeably.

The term "sequence" hereinafter refers to a nucleic acid characterized by the sequence of its nucleotides. The term "nucleic acid" herein may mean any nucleic acid containing molecule including, but not limited to, DNA or RNA wherein one or more nucleotides are selected from the group consisting of adenine, guanine, cytosine, thymine, uracil or their functional equivalents like, for example, inosine and hypoxanthine, and wherein each nucleobase is linked to a backbone comprising a pentose such as ribose and/or deoxyribose, another sugar or an amino acid, and wherein the individual backbones are linked/connected to one another by, for example, phosphodiester. The term encompasses sequences that include any base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methyl guanine, 3-methylcytosine, 5-methylcytosine, N6-methyladenine, 7-methylguanine, 5-methylaminomethyluracils, 5-methoxyaminomethyl-2-thiouracil, ÿ-D-maminosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

In one embodiment, the present invention provides compositions comprising lignin. In various embodiments, lignin is present in a composition of the invention in an amount of at least about 0.01%, at least about 0.05%, at least about 0.1%, at least about 0.5%, at least about 1%, at least about 2.5%, at least about 5%, at least about 10%, at least about 15%, at least about 20%, at least about 25%, at least about 30%, at least about 40%, at least about 50%, at least about 60%, at least about 70%, at least about 80%, or at least about 90%, by weight. In another embodiment, a composition of the invention comprises a therapeutically effective amount of lignin. The related terms "therapeutically effective amount," "prophylactically effective amount," "effective amount" or "amount effective to treat" as used herein refer to an amount of lignin that is sufficient to elicit the required or desired therapeutic and/or prophylactic response, as the particular treatment context may require. Such compositions optionally comprise one or more pharmaceutically acceptable excipients. The phrase "pharmaceutically acceptable" in the present context means that the excipient in question does not produce unacceptable toxicity when administered to a vertebrate subject and does not have unacceptable interaction with other components of the composition.

In one embodiment, compositions of the invention can be prepared by, inter alia, heat extracting plant materials with an alkaline agent. Illustrative plant materials include pine cones.

Pine cones suitable for use in the present invention can be of any species and variety of genus *Pinus*, especially those of Table 1, without intended limitation to the correctness of the taxonomical classification of that table. In one embodiment, suitable pine cones are those of *P. taeda* (loblolly), *P. elliottii* (slash), and *P. palustris* (long leaf). Pine cones in general and pine cones of the latter group in particular contain substances and compounds (active ingredients) useful in vaccination and/or therapy methods and likewise comprise substances and compounds useful for the production of dendritic and/or fibrocyte cells. It is also presently believed, without being bound by theory, that the lignin fraction of pine cone extracts is necessary but not sufficient for satisfactory immunostimulatory properties of pine cone extracts, particularly in nucleic acid vaccination and/or treatment methods.

TABLE 1

Pines producing pine cones useful for preparing pine cone extracts

| | |
|---|---|
| Subgenus *Pinus* | |
| Section *Pinus*, Subsection *Pinus* | *P. densata, P. densiflora, P. heldreichii, P. hwangshanensis, P. kesiya, P. luchuensis, P. massoniana, P. mugo, P. nigra, P. resinosa, P. sylvestris, P. tabuliformis, P. thunbergii, P. tropicalis, P. yunnanensis* |
| Section *Pinea*, Subsection *Pinaster* Loudon | *P. brutia, P. canariensis, P. halepensis, P. latteri, P. merkusii, P. pinaster, P. roxburghii* |
| Section *Pinea*, Subsection *Pineae* Little & Critchfield | *P. pinea* |
| Section *Trifoliis*, Subsection *Contortae* Little & Critchfield | *P. banksiana, P. contorta* |
| Section *Trifoliis*, Subsection *Australes* Loudon | *P. caribaea, P. clausa, P. cubensis, P. echinata, P. elliottii, P. glabra, P. occidentalis, P. palustris, P. pungens, P. rigida, P. serotina, P. taeda, P. virginiana* |
| Section *Trifoliis*, Subsection *Ponderosae* Loudon | 'Sabinianae Group': *P. coulteri, P. sabiniana, P. torreyana*<br>'Ponderosa Group': *P. arizonica, P. durangensis, P. engelmannii, P. jeffreyi, P. ponderosa, P. washoensis*<br>'Montezumae Group': *P. devoniana, P. hartwegii, P. montezumae*<br>'Pseudostrobus Group': *P. douglasiana, P. maximinoi, P. pseudostrobus* |
| Section *Trifoliis*, Subsection *Oocarpae* Little & Critchfield | 'Attenuata Group': *P. attenuata, P. muricata, P. radiata*<br>'Oocarpa Group': *P. greggii, P. jaliscana, P. oocarpa, P. patula, P. praetermissa, P. pringlei, P. tecunumanii*<br>'Teocote Group': *P. herrerae, P. lawsonii, P. teocote* |
| Section *Trifoliis*, Subsection *Leiophyllae* Loudon | *P. leiophylla, P. lumholtzii* |
| Subgenus *Ducampopinus* | |
| Section *Ducampopinus*, Subsection *Krempfianae* Little & Critchfield | *P. krempfii* |
| Section *Gerardiana*, Subsection *Gerardianae* Loudon | *P. bungeana, P. gerardiana, P. squamata* |

TABLE 1-continued

Pines producing pine cones useful for preparing pine cone extracts

| | |
|---|---|
| Section *Parryana*, Subsection *Nelsoniae* Van der Burgh | *P. nelsonii* |
| Section *Parryana*, Subsection *Rzedowskianae* Carvajal | *P. maximartinezii, P. pinceana, P. rzedowskii* |
| Section *Parryana*, Subsection *Cembroides* Engelmann | *P. cembroides, P. culminicola, P. discolor, P. edulis, P. johannis, P. juarezensis, P. monophylla, P. orizabensis, P. remota* |
| Section *Parryana*, Subsection *Balfourianae* Engelmann | *P. aristata, P. balfouriana, P. longaeva* |
| Subgenus *Strobus* | |
| Section *Strobus*, Subsection *Strobi* Loudon | *P. amamiana, P. armandii, P. ayacahuite, P. bhutanica, P. chiapensis, P. dalatensis, P. fenzeliana, P. flexilis, P. lambertiana, P. monticola, P. morrisonicola, P. parviflora, P. peuce, P. pumila, P. strobiformis, P. strobus, P. wallichiana, P. wangii* |
| Section *Strobus*, Subsection *Cembrae* Loudon | *P. albicaulis, P. cembra, P. koraiensis, P. sibirica* |

Alkaline extracts in accordance with various embodiments of the present invention can be obtained from a variety of plants. Such plants include, but are not limited to, magnolia trees, bamboo trees, palm trees, Spanish moss, orange pekoe tea, pekoe black tea, green tea, mountain araucaria or bushy bluestem. Various plant materials, including leaves, needles, bark, stalk or sheath can be used for preparation of an alkaline extract in accordance with the present invention (see Table 2).

TABLE 2

Various Plants Useful for Preparing Alkaline extracts

| # | Section of Plant | Common Name | Genus Species |
|---|---|---|---|
| 1 | Leaves | Loquat | *Eriobotrya Japonica* |
| 2 | Leaves | Orange Pekoe and Pekoe Black tea | *Camellia sp.* |
| 3 | Leaves (needles) | Japanese Black Pine | *Pinus Thunbergii* |
| 4 | Bark | Japanese Black Pine | *Pinus Thunbergii* |
| 5 | Leaves (needles) | Mountain Araucaria | *Araucaria Montana* |
| 6 | Bark | Mountain Araucaria | *Araucaria Montana* |
| 7 | Leaves | Southern Magnolia | *Magnolia Grandiofloria* |
| 8 | Stalk | Bamboo Golden Goddess | *Bambusa Multiplex* |
| 9 | Sheath | Golden Goddess | *Bambusa Multiplex* |
| 10 | Leaves (needles) | Sargent Juniper | *Juniperus Sargentii* |
| 11 | Leaves | Bushy Bluestem | *Andropogon Glomeratus* |
| 12 | Leaves (needles) | Loblolly Pine | *Pinus Taeda* |
| 13 | Bark | Slash Pine | *Pinus Elliottii* |
| 14 | Cone | Loblolly Pine | *Pinus Taeda* |
| 15 | Leaves | Scrub Palm | *Sabal Etonia* |
| 16 | Whole plant | Spanish Moss | *Tillandsia Usneoids* |
| 17 | Leaves (needles) | Slash Pine | *Pinus Elliottii* |

Figure 9A:
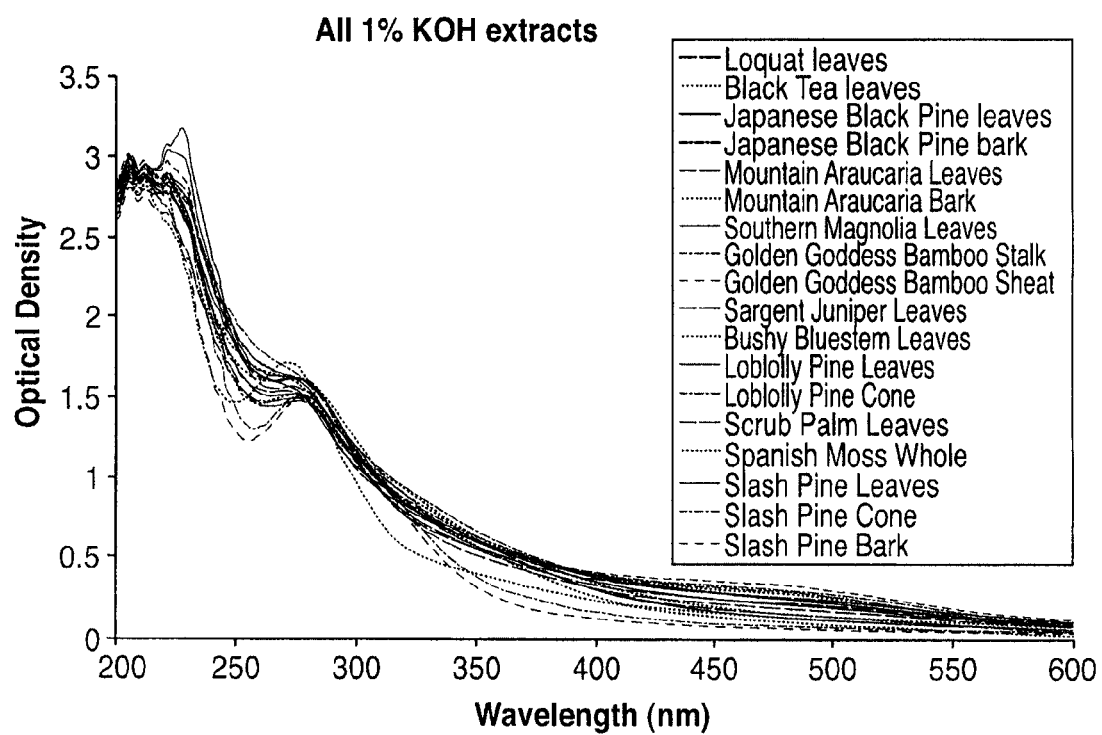
FIG. 9A shows spectra taken in the 200 to 600 nm range for 20 different samples.

As seen in FIG. 9A, the spectra of alkaline extracts obtained from the majority of plants are similar to a spectrum of alkaline extract obtained from pine cones. Extracts obtained from different sections (e.g. bark versus leaves) of the same plant generated similar spectra (compare spectra for Japanese black pine leaves and bark in FIG. 9B). While alkaline extracts obtained from the majority of plants have spectra similar to the spectrum of potassium hydroxide extract obtained from pine cones, alkaline extracts of several plants were found to contain an additional peak in comparison to the pine cone extract.

Figure 9B:
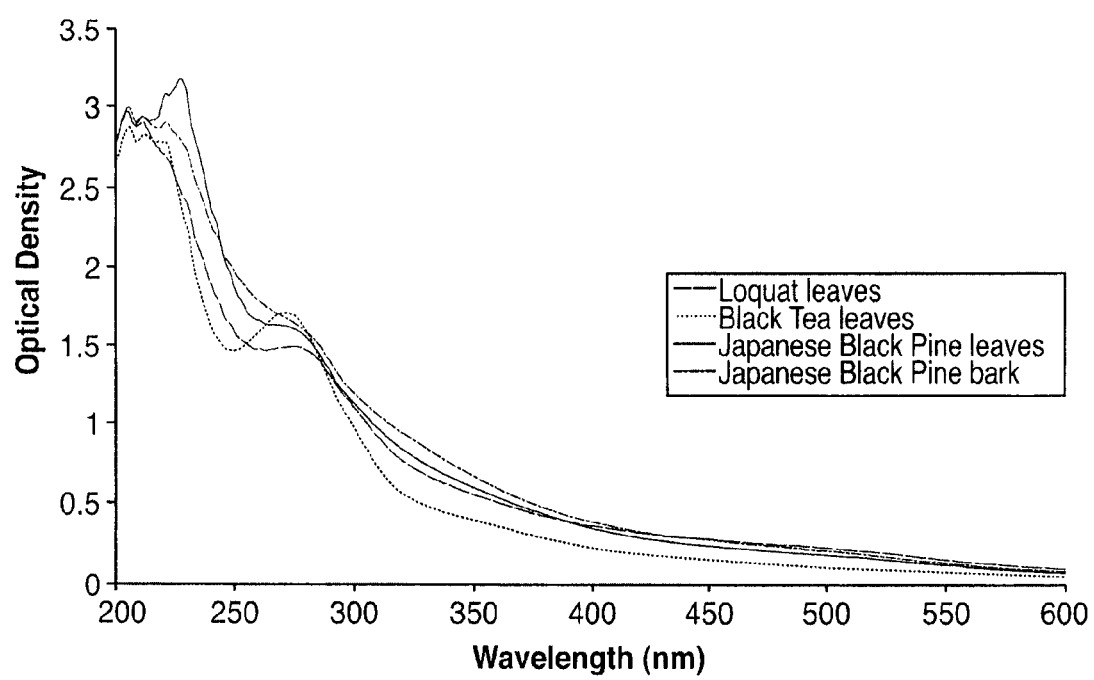
FIG. 9B shows an additional peak seen at about 250 nm in alkaline extracts of black tee leaves. In this particular extract, the peak is at 272 nm and has an optical density of 1.706.
Figure 9C:
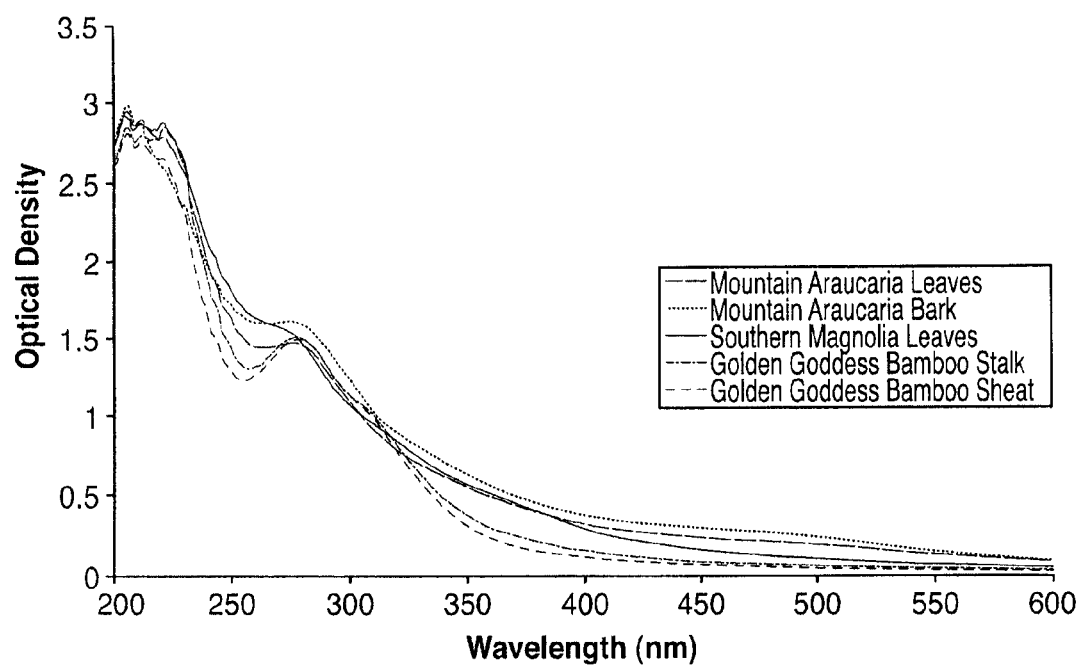
FIG. 9C shows golden goddess bamboo stalk and sheath alkaline extracts have additional peaks at about 250. In this particular preparation, the stalk has a peak at 278 nm and has an optical density of 1.51. The sheath has a peak at 278 nm and has an optical density of 1.497.

For example, as seen in FIG. 9B, an additional peak observed at about 250 nm in alkaline extracts of black tee leaves that was not present in pine cone extracts. Another example of an extract whose spectrum contains an additional peak is an alkaline extract made from golden goddess bamboo stalk or sheath. As shown in FIG. 9C, the spectrum of alkaline extract made from golden goddess bamboo stalk or sheath revealed an additional peak at 278 nm.

Figure 9D:
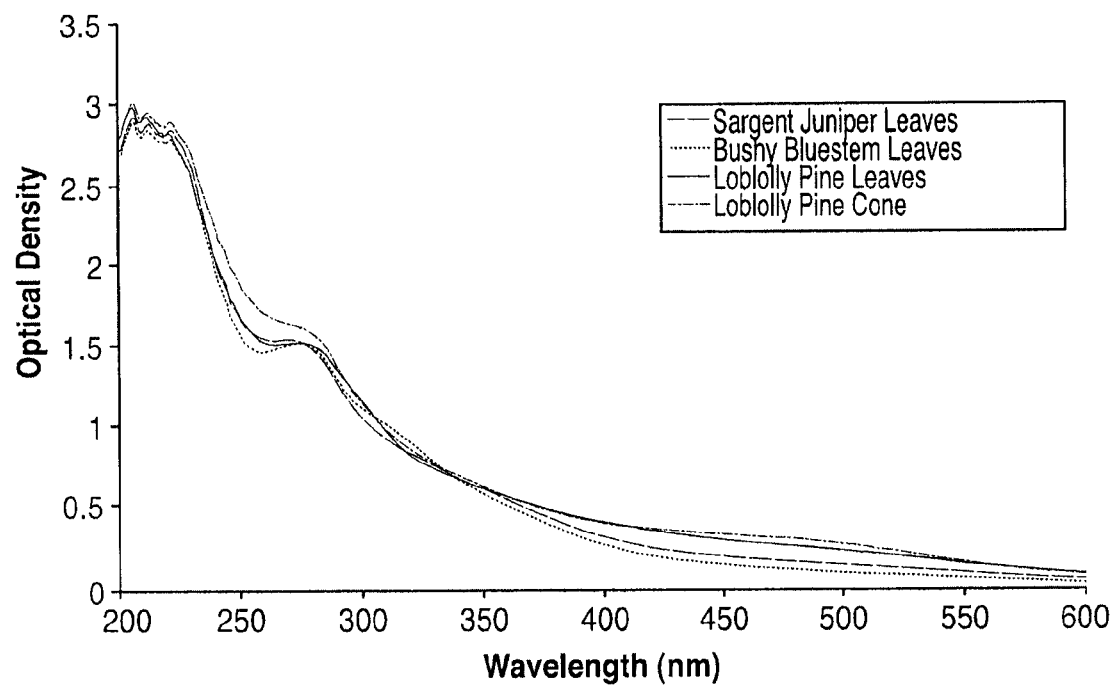
FIG. 9D shows spectra of alkaline extracts obtained from Sargent Juniper, Bushy Bluestem and Loblolly.
Figure 9E:
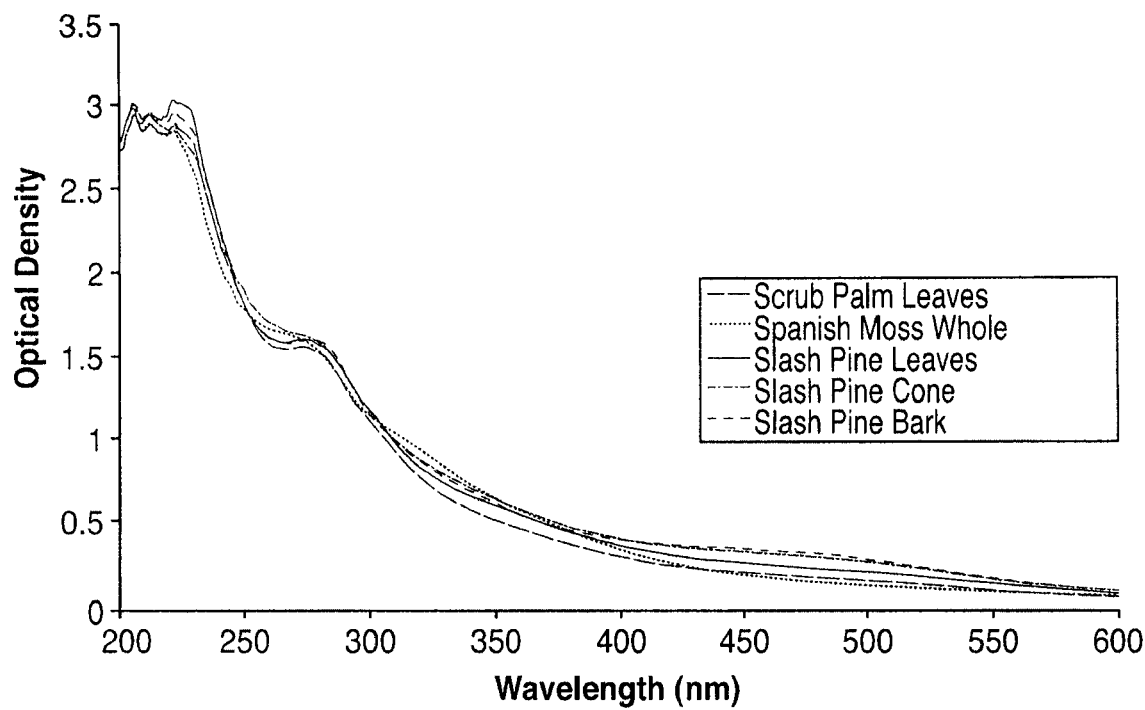
FIG. 9E shows spectra of alkaline extracts obtained from Scrub Palm, Spanish Moss, Slash Pine Leaves, Slash Pine Cones and Slash Pine Bark.

Spectra of alkaline extracts obtained from Sargent Juniper, Bushy Bluestem and Loblolly (FIG. 9D) and spectra of alkaline extracts obtained from Scrub Palm, Spanish Moss, Slash Pine Leaves, Slash Pine Cones and Slash Pine Bark (FIG. 9E) are very similar to the spectrum of alkaline extract obtained from pine cones.

In one embodiment, extraction methods of the invention can be divided into two phases, hereinafter termed Phase 1 and Phase 2. Extraction methods of the invention can involve either phase 1 or phase 2, or both phase 1 and phase 2 (also referred to as methods 1 and 2).

Phase 1

Phase 1 involves heat extraction of the material to be extracted (e.g. plant material, bacterial cell material or mammalian cell material) with an aqueous solvent having a pH greater than 7, for example potassium hydroxide. After the extraction, particulate matter with an average particle size (on a weight or number basis) greater than about 0.1 nm, about 0.15 nm, about 0.2 nm, or about 0.2 µm is removed. A resulting aqueous solution is obtained (supernatant); pH of the supernatant can be adjusted to be between 6.0 and 8.0 to obtain the extract of Phase 1.

Phase 2 utilizes the extract (supernatant) obtained by Phase 1. In Phase 2, the extract of Phase 1 (a solution) is subjected to further filtration to obtain a retentate fraction. By way of a centrifugal filtration process, a remaining particulate matter is removed, for example particulate matter smaller than about 10, 20, 30, 40 or 50 kDa. What remains is particulate matter greater than about 10, 20, 30, 40 or 50 kDa on top of the filter. This retentate fraction is alkaline extract of Phase 2.

For the purpose of the above methods, the plant material can be in the form of whole, ground, minced, or shredded material. Shredded material facilitates subsequent extraction, is commercially available, easily transportable and maintains sufficiently stable and uniform composition throughout several batches.

Prior to use in the above methods, the starting material can be cleaned if desired. Cleaning can be accomplished by washing plant material with, for example, deionized water or washing cells with phosphate-buffered saline (PBS).

In one embodiment, the plant material is defatted prior to aqueous extraction. Defatting can be achieved by washing the plant material with ethanol and subsequent drying of plant material or centrifuging of the cells. The defatted plant material can be stored at room temperature or stored at −70° C. in a closed container prior to extraction. Alternatively, starting material can be stored directly after harvesting and washing with deionized water or PBS and prior to defatting. If the starting material is stored directly after harvest, the defatting step can be undertaken at a later time, for example immediately prior to subsequent extraction.

Prior the extraction step, plant material can ground into small particles. This treatment facilitates release of active ingredients. In one embodiment, the particle size of the starting material is in the range of 80-120 mesh.

In another embodiment, the solvent for heat extraction of plant material is an aqueous solution having a pH of at least about 7. In one embodiment, the solution comprises an alkaline agent. The term "alkaline agent" herein refers to an agent possessing activity as a weak or strong base. In one embodiment, the alkaline agent comprises a salt of a Group IA metal including, for example, a bicarbonate salt of a Group IA metal, a carbonate salt of a Group IA metal, an alkaline earth metal agent, an amino acid, an alkaline salt of an amino acid, alkali (sodium and potassium) or alkaline earth (calcium and magnesium) phosphates, bicarbonates, citrates, borates, acetates, phthalates, tartrates, succinates and the like, such as sodium or potassium phosphate, citrate, borate, acetate, bicarbonate and carbonate.

In various embodiments, the alkaline agent is selected from aluminum hydroxide, magnesium hydroxide, aluminum hydroxide/magnesium hydroxide co-precipitate, aluminum hydroxide/sodium bicarbonate co-precipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium hydroxide, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and mixtures thereof.

In one embodiment, the solvent comprises at least about 0.1% w/w, at least about 0.2% w/w, at least about 0.25% w/w, or about 0.5% to about 2% w/w, for example about 1% w/w, of an alkaline agent. In various embodiments, pH of the solvent is at least about 8, at least about 9, at least about 10, or in the range of 11-13.

Extraction of plant material (also referred to as "starting material") is performed by adding solvent to the starting material to form a mixture, and heating the mixture, for example to temperatures at or above 80° C. (176° F.). Heating the mixture can be accomplished in any manner, for example by boiling or autoclaving, for example at 121° C.

After extraction, the mixture can be allowed to cool, for example to room temperature. If necessary, the mixture can be stored in a refrigerator or freezer, for example for 12 hours, 24 hours, days or weeks, prior to further processing.

Particulate matter with an average particle size greater than 0.10 µm, 0.15 µm, 0.20 µm or 0.25 µm can be removed from the mixture to form a particle-depleted mixture. This can be achieved by any particle separation method. In on embodiment, the separation method comprises a two step process, wherein in the first step coarse particulate matter is removed by filtration, and in the second step, remaining unwanted particulate matter is removed by centrifugation, for example at 4° C.±2° C.

The resulting particle-depleted mixture can be treated to adjust its pH to about 6.0 to about 8.0, for example by titration with 1 N HCl. The particle-depleted mixture can then optionally be divided into two or more units for packaging and can be sterilized before or after any such division step takes place.

The particle-depleted mixture obtained by above Phase 1 can be stored after pH adjustment and optional sterilization. Long-term storage stability is best ensured by storage at low temperatures, for example at or below 4° C., in a frozen state, or at −20° C. In other embodiments, the mixture can be further used without storage.

Phase 2

After pH adjustment and optional sterilization, the mixture of Phase 1 can be subjected to further filtration to remove material smaller than 50 kDa, 40 kDa, 30 kDa, 20 kDa or 10 kDa, for example using Millipore Ultrafree Centrifugal concentrators. In one embodiment, filtration can include centrifugation, for example at 2000×g for 60 min, to filter the solution and recover the retentate fraction.

The retentate fraction can optionally be returned to its original volume using an alkaline solvent, for example aqueous 10 mM potassium hydroxide solution at a pH between 6.0 and 8.0, for example 7.0. The volume of alkaline solvent can be adjusted according to the desired concentration of retentate fraction.

If the retentate fraction is mixed with alkaline solvent, the solution can optionally be sterilized, for example by filtration (e.g. with a 0.2 µm filter), sterilization, irradiation, etc. Other sterilization techniques may likewise be applied. The resulting extract of Phase 2, via the further filtration and optionally sterilized concentrate, can be further used according to various embodiments of the present invention. Alternatively, the non-solubilized retentate can be used according to various embodiments of the present invention.

Lignin Compounds, Compositions and Dosage Forms

Figure 2:
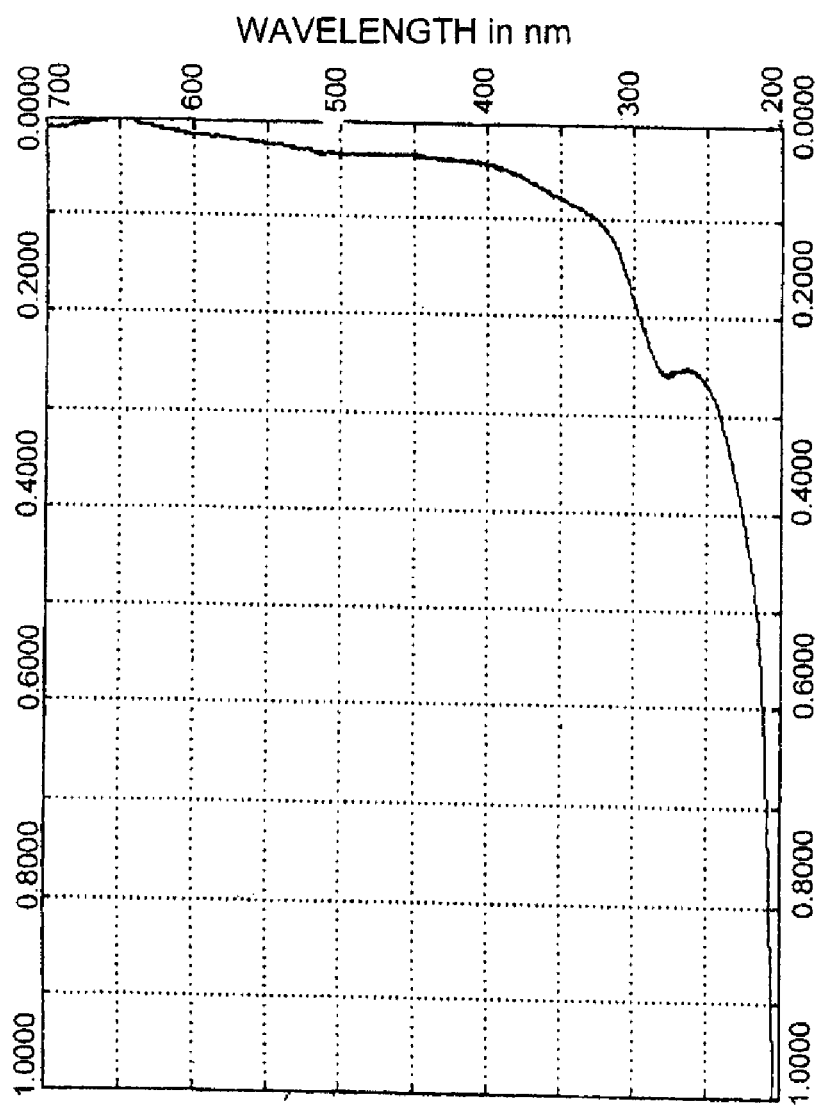
FIG. 2 shows an absorption spectrum of the pine cone extract of Phase 1, Example 1.

The present invention also provides lignin compounds. The term "lignin compound" herein refers to a compound or complex or mixture of compounds comprising lignin. The term "lignin" refers to phenolic polymers (e.g. polyphenylpropenoid) that confer strength and/or rigidity to the cell wall of plants, for example the woody cell wall of plant. In one embodiment, the lignin compound has a UV spectrum as shown in any one of FIG. 1-2 or 9. In another embodiment, the lignin compound comprises alkaline extract of the invention.

In another embodiment, the lignin compound is complexed or mixed with a carbohydrate, for example a sugar. In one embodiment, the lignin is a covalently linked polyphenylpropenoid-polysaccharide complex. In still another embodiment, the lignin compound is in substantially pure form (i.e. is not complexed or mixed with other compounds). In yet another embodiment, the lignin compound comprises at least about 25%, at least about 50%, at least about 60%, at least about 70%, at least about 80%, at least about 90% or at least about 95% phenolic compounds, by weight. In yet another embodiment, the lignin compound comprises not more than about 90%, not more than about 80%, not more than about 70%, not more than about 60%, not more than about 50% not more than about 40%, not more than about 30%, not more than about 20%, or not more than about 10% of non-phenolic material (e.g. carbohydrate), by weight. In another embodiment, the lignin compound has a molecular weight greater than about 90, about 95, or about 100 kDa, for example about 90 to about 1000 kDa, about 95 to about 500 kDa or about 100 to about 250 kDa.

In still another embodiment, the present invention provides substantially pure compounds having a spectrum as shown in any one of FIG. 1-2 or 9-12.

The present invention also provides pharmaceutical compositions comprising a lignin compound or alkaline extract as described herein and at least one pharmaceutically acceptable excipient. In one embodiment, the lignin compound is present in the composition in a total amount of at least about 10%, 20%, 40%, 60% or 80%, by weight of the composition.

The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, about 10% to about 85%, or about 20% to about 80%, of the total weight of the composition.

Compositions of the invention optionally comprise one or more pharmaceutically acceptable disintegrants as excipients. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, typically comprise in total about 0.2% to about 30%, about 0.2% to about 10%, or about 0.2% to about 5%, of the total weight of the composition.

Compositions of the invention optionally comprise one or more antioxidants. Illustrative antioxidants include sodium ascorbate and vitamin E (tocopherol). One or more antioxidants, if present, are typically present in a composition of the invention in an amount of about 0.001% to about 5%, about 0.005% to about 2.5%, or about 0.01% to about 1%, by weight.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the composition. Glidants can be used to promote powder flow of a solid formulation. Suitable glidants include colloidal silicon dioxide, starch, talc, tribasic calcium phosphate, powdered cellulose and magnesium trisilicate.

Compositions of the present invention can comprise one or more flavoring agents, sweetening agents, and/or colorants. Flavoring agents useful in the present invention include, without limitation, acacia syrup, alitame, anise, apple, aspartame, banana, Bavarian cream, berry, black currant, butter, butter pecan, butterscotch, calcium citrate, camphor, caramel, cherry, cherry cream, chocolate, cinnamon, citrus, citrus punch, citrus cream, cocoa, coffee, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, MagnaSweet®, maltol, mannitol, maple, menthol, mint, mint cream, mixed berry, nut, orange, peanut butter, pear, peppermint, peppermint cream, Prosweet® Powder, raspberry, root beer, rum, saccharin, safrole, sorbitol, spearmint, spearmint cream, strawberry, strawberry cream, stevia, sucralose, sucrose, Swiss cream, tagatose, tangerine, thaumatin, tutti fruitti, vanilla, walnut, watermelon, wild cherry, wintergreen, xylitol, and combinations thereof, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, etc.

Sweetening agents that can be used in the present invention include, for example, acesulfame potassium (acesulfame K), alitame, aspartame, cyclamate, cylamate, dextrose, isomalt, MagnaSweet®, maltitol, mannitol, neohesperidine DC, neotame, Prosweet® Powder, saccharin, sorbitol, stevia, sucralose, sucrose, tagatose, thaumatin, xylitol, and the like.

Flavoring agents, sweetening agents, and/or colorants can be present in compositions of the invention in any suitable amount, for example about 0.01% to about 10%, about 0.1% to about 8%, or about 1% to about 5%, by weight.

The foregoing excipients can have multiple roles as is known in the art. For example, starch can serve as a filler as well as a disintegrant. The classification of excipients above is not to be construed as limiting in any manner. Excipients categorized in any manner may also operate under various different categories of excipients as will be readily appreciated by one of ordinary skill in the art.

Solid Dosage Forms

In some embodiments, compositions of the invention are in the form of solid dosage forms or units. Non-limiting examples of suitable solid dosage forms include tablets (e.g. suspension tablets, bite suspension tablets, rapid dispersion tablets, chewable tablets, effervescent tablets, bilayer tablets, etc), caplets, capsules (e.g. a soft or a hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

Tablets are an illustrative dosage form for compositions of the invention. Tablets can be prepared according to any of the many relevant, well known pharmacy techniques. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms such as tablets can be prepared by mixing a lignin compound with at least one excipient as described herein above to form a substantially homogeneous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the invention. The term "compressed tablet" generally refers to a plain, uncoated tablet suitable for oral ingestion, prepared by a single compression or by pre-compaction tapping followed by a final compression. Tablets of the present invention may be coated or otherwise compounded to provide a dosage form affording the advantage of improved handling or storage characteristics. Preferably, however, any such coating will be selected so as to not substantially delay onset of therapeutic effect of a composition of the invention upon administration to a subject. The term "suspension tablet" as used herein refers to a compressed tablet that rapidly disintegrates after placement in water.

Liquid Dosage Forms

In another embodiment of the invention, compositions can be liquid dosage forms or units. Non-limiting examples of suitable liquid dosage forms include solutions, suspension, elixirs, syrups, liquid aerosol formulations, etc.

Vaccination and Therapy

In another aspect, the present invention provides a system for vaccination and/or therapy. Subjects eligible for the treatment or vaccination include any vertebrates (terrestrial or aquatic), for example vertebrate mammals including humans, apes, dogs, cats, rabbits, goats, guinea pigs, hamsters, cows, horses, sheep, mice and rats. The general properties of the immune system of these vertebrates are similar enough so that experimental findings in one species can be interpolated with reasonable confidence to other species.

In one embodiment, the system for vaccination and/or therapy comprises a composition or kit comprising (a) a vaccine or medicament and (b) one or more of an alkaline extract, a lignin compound, or a composition comprising either.

Without being bound by theory, it is believed that the beneficial effect of alkaline extract or lignin compound is not dependent on the simultaneous administration of vaccine and extract. The alkaline extract can be administered to the vertebrate before, during, simultaneously with or after administration of the vaccine or medicament. The inventive system for vaccination and/or therapy is therefore not limited to compositions comprising both vaccine and alkaline extract, but can also be a kit comprising, as separate entities, the vaccine, optionally also comprising an alkaline extract, and the alkaline extract itself. A composition comprising vaccine and/or medicament and a lignin compound or alkaline extract is particularly useful for simultaneous administration of both ingredients to the vertebrate to be treated. The kit allows for the independent administration of vaccine (or medicament) and alkaline extract. The kit is therefore particularly suitable if administration of the alkaline extract to the vertebrate is to start before, simultaneous with, or after administration of the vaccine.

In one embodiment, the vaccine or medicament is a nucleic acid vaccine or medicament. With nucleic acid vaccines and/or medicaments, a particularly high degree of immunization or activation of the immune system can be achieved when used with an alkaline extract of the invention.

In a further embodiment of the invention, the lignin compound or alkaline extract comprises an alkaline extract produced by Phase 1 (supra), that is by heat extraction of any of the starting material with an aqueous solvent containing an alkaline agent, then removing particulate matter with an average particle size greater than a desired size, and finally adjusting the pH of the resulting solution to between 6.0 and 8.0.

Another embodiment of the invention provides a kit or composition wherein the alkaline extract comprises an alkaline extract produced by Phase 2, wherein the extract is fractionated. Such alkaline extract, being in effect the fraction of molecules with a desired minimum kDa size obtained by Phase 1, comprises essentially all immunoactive ingredients required for stimulating the immune system or, in ex vivo or in vitro applications, the cells required in mediating the immune response to the antigen of the vaccine or medicament.

The invention also provides a method of vaccinating or treating a vertebrate, wherein the vertebrate is administered a compound or composition comprising a lignin compound or alkaline extract as described herein, optionally together with, before or after administration of a vaccine or medicament to the vertebrate.

Lignin compound or alkaline extracts prepared according to the methods of the invention may also be used for improving general immune responses (e.g. in subjects with weakened or compromised immune systems). To improve subject's general immune responses, the alkaline extracts of the invention can be administered to the subject either alone or in combination with other compositions. In a further embodiment, the invention provides alkaline extract produced by Phase 1.

The present invention further provides methods for treatment and prevention of tumors. In one embodiment, the method includes the use of a lignin compound or alkaline extract as disclosed herein as an antigen in the prevention and treatment of tumors by enhancing the response to tumor-specific antigens or tumor-associated antigens that may otherwise by weakly immunogenic or not immunogenic.

Examples of tumor-associated antigens include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE I, MAGE 2, TRP I, TRP 2, tyrosinase, MART-I, PAP, CEA, BAGE, MAGE, RAGE, and related proteins.

Examples of tumors that may be treated by the present invention include, without limitation, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia). Because of the powerful adjuvant properties of the pine cone extract of the present invention, the method is particularly suited to the treatment and prevention of weakly immunogenic tumors.

In other embodiments, the invention provides a method for increasing the immune response in a vertebrate subject. In one embodiment, the method includes the step of administering to the subject a lignin compound or alkaline extract of the present invention. In another embodiment, the method further includes the step of increasing the amount of one or more immunogens in the vertebrate. The amount of the immunogen or immunogens may be increased, for example, by promoting release of a preexisting immunogen, administering an immunogen to the subject, administering a cell comprising an immunogen, administering a cell fraction comprising an immunogen, administering a polynucleotide encoding an immunogen, or by any combination of such methods.

As used herein, the term "immunogen" encompasses any antigenic or immunogenic polypeptides including polyaminoacid materials having epitopes or combinations of epitopes, and immunogen-encoding polynucleotides. In addition, an "immunogen" is also intended to encompass any polysaccharide material useful in generating immune response. As used herein, an antigenic polypeptide or an immunogenic polypeptide is a polypeptide which, when introduced into a vertebrate, reacts with the immune system molecules of the vertebrate, i.e., is antigenic, and/or induces an immune response in the vertebrate. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens. Examples of such antigenic and immunogenic polypeptides are listed in U.S. Pat. No. 6,586,409 which is hereby incorporated by reference herein in its entirety.

As used herein, the term "pre-existing immunogen" includes tumor associated antigens and antigens that may be rendered more antigenic by a treatment promoting its release. The term "release" in the present context is to be broadly understood as including a change in the location, milieu, physical structure, or the like, of an immunogen such that the change renders the immunogen more available or apparent to the immune system. Examples of treatments releasing immunogen include, but are not limited to, ultrasound, chemotherapy, radiation therapy, and electrochemotherapy. Electrochemotherapy is described, for example, in U.S. Pat. Nos. 5,702,359; 6,418,341; 6,451,002; 6,569,149; and 6,714,816, which are hereby incorporated herein by reference herein.

Administration of a vaccine, lignin compound, alkaline extract and/or composition comprising the same can be accomplished in any suitable manner, for example by oral, nasal or anal administration, transdermal or cutaneous administration, subcutaneous injection, intramuscular injection or intravenous injection, etc. The term "oral administration" herein includes any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration.

Injection can be accomplished using syringe systems or devices commonly termed "particle guns". The mode of administration of the vaccine or medicament is chosen in accordance with the nature of the vaccine or composition to be delivered. While some vaccines achieve high immunization levels by intramuscular injection, others are preferentially administered orally.

According to another aspect, the invention provides a method for producing phenotypically immature and/or mature dendritic and/or fibrocyte cells. This method comprises exposing cells selected from the group of blood mononuclear cells, thymocytes, splenocytes, umbilical cord blood cells, bone marrow cells, $CD34^+$-cells, $CD14^+$-cells or mixtures thereof to an effective amount of a lignin compound or alkaline extract as described herein.

Figure 28:
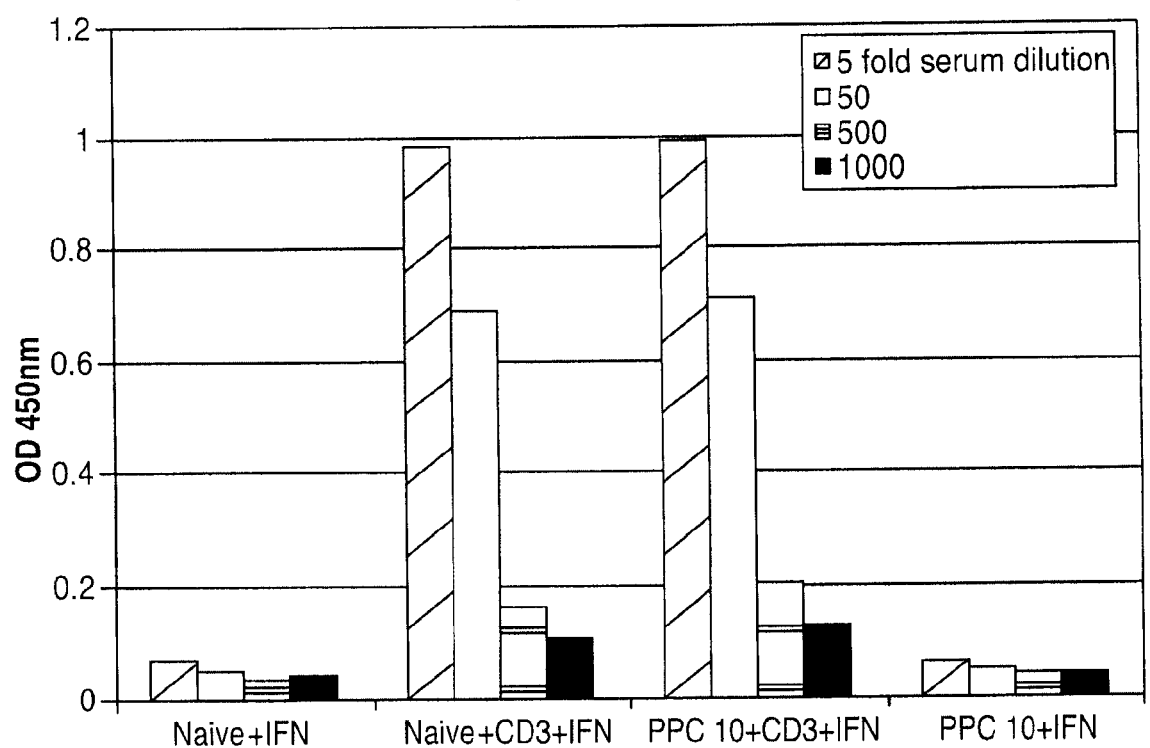
FIG. 28 shows ELISA measurement of anti-IFNgamma/IFN-gamma complex in serum of Balb/c mice gavaged with pine cone alkaline extract or injected with T-cell mitogenic anti-CD3E antibody.

Without being bound by theory, it is believed that lignin compounds and alkaline extracts of the invention have a pronounced effect on the differentiation process of cells of the immune system. In particular, lignin compounds and alkaline extracts can induce differentiation to phenotypically immature and/or mature dendritic cells and fibrocytes. The invention now enables attainment of a particularly high yield of cells that have differentiated into immature and/or mature dendritic cells. Such high yields were not believed to be attainable previously by common methods of induction of differentiation, e.g. doses of cytokines. As seen in FIG. 28, treatment of human peripheral blood mononuclear cells (PBMC) with a PPC extract results in the development of myeloid DCs with a phenotype that is distinct from the GM-CSF/IL4-derived mDCs. Differentiation can be advantageously enhanced by further exposing the selected cells or the selected mixture to CD3-cells.

In one embodiment, the alkaline extract used to achieve a high yield of immature and/or mature dendritic and/or fibrocyte cells is produced according to Phase 1 or Phase 2. Such alkaline extracts are particularly effective in inducing the desired differentiation into phenotypically immature or mature dendritic cells and/or fibroblasts. This method of differentiation can be advantageously combined with exposure to $CD3^+$-cells to achieve and maintain a high yield of differentiation.

Several methods for measuring activity of lignin compound/alkaline extract can be utilized. In one embodiment, the concentration of alkaline extract can be measured by spectroscopy as O.D. at 280 nM. Alkaline extract activity can also be measured in an adherence assay of peripheral blood mononuclear cells. In such an assay, mononuclear cells are incubated with the alkaline extract at concentrations in the range of about 5 to about 500 μg of alkaline extract per 1 ml of media, or about 150 to about 250 μg of alkaline extract per 1 ml of media, for 36 to 80 hours, for example about 72 hours. Attachment to the bottoms of culture dishes of cells treated with the alkaline extract in comparison to attachment of cells not treated with the alkaline extract can then be measured by counting the percentage of the attached cells in each plate. Incubation with the alkaline extract may increase adherence of peripheral blood mononuclear cells.

EXAMPLES

The following examples illustrate various aspects of the present invention and are not to be construed as limiting the invention in any manner.

Example 1

Preparation of a Pine Cone Extract According to Phase 1

This example illustrates the production of pine cone extracts (PCE) according to Phase 1. Commercially available shredded pine cone material from International Forest Company such as, loblolly pine, slash pine and long leaf pine is provided. 5 kg of the shredded pine cone material is washed twice in about 10 liters of deionized water. The washed pine cone material is then defatted by briefly washing it in 10 liters of 95% ethanol with agitation. The pine cone material is air dried over night and can be stored at room temperature (18-25° C.) if not used immediately.

The cleaned and defatted pine cone material is ground to a particle size of approximately 80-120 mesh in a blender. Of this ground material, 600 g are placed in a 20 l spinner flask. 4.5 l of 1% w/w aqueous potassium hydroxide solution are added. The opening of the flask is plugged with a cotton ball wrapped with cheesecloth. The flask is then autoclaved for 1 h with slow exhaust at 121° C. under liquid cycle conditions. After autoclaving, the flask is allowed to cool off. If its contents are not immediately processed further, the flask can be stored in a refrigerator at 4° C.

Large particles are filtered out of the autoclaved suspension with a nylon mesh filter on a Buchner funnel attached to a suction flask with vacuum applied thereto. Fine particles are removed by centrifuging the filtrate in a Beckman medium speed centrifuge using a JA-10 rotor and corresponding bottles, centrifuging at 8000 rpm for 10 min at 4° C. The supernatant is taken off and processed further.

The pH of the centrifugation supernatant (extract) is adjusted to 7.0 by adding 1 N aqueous hydrochloric acid. A control sample of 10 ml of the neutralized supernatant is retained.

The neutralized extract is distributed into 500 ml glass bottles (approx. 400 ml per bottle). If not used immediately, the extract is stored in a refrigerator. The extract is sterilized by autoclaving for 20 min at 121° C. under liquid cycle conditions. After cooling, the autoclaved extract (extract according to Phase 1) is ready to be used. It can be stored in a refrigerator.

Example 2

Preparation of a Pine Cone Extract According to Phase 2 of Example 1

This example illustrates the production of pine cone extracts according to Phase 2.

15 ml of the pine cone extract of example 1 is placed in a sterile 50 ml conical polypropylene centrifuge bottle (Millipore Ultrafree-15 centrifugal concentrator, Fisher cat. no. UFV2 BTK 10) and centrifuged for 1 h at 2000×g (Eppendorf model 5810R centrifuge) (room temperature to 4° C.). The retentate fraction is drawn off and saved. The filtrate, containing molecules smaller that 30 kDa is discarded.

The retentate fraction is suspended in 10 mM aqueous potassium hydroxide buffer at pH 7.0 to produce a final extract volume of 15 ml.

The suspended retentate fraction (extract Phase 2) is sterilized by vacuum filtration with a 0.2 µm filter (Nalgene PES membrane, cat. no. 124-0020).

The sterilized pine cone extract of Phase 2 is then ready to be used. It can be stored in a refrigerator.

Example 3

Properties of Pine Cone Extracts of Examples 1 and 2

This example illustrates the properties of pine cone extracts according to methods 1 and 2.

The pine cone extracts of phase 1 and 2 are brown liquids. They are miscible with water, with mixtures of water and ethanol and with acetone. They comprise polysaccharides and polyphenylpropenoids. The molecular weights of the main components are given in table 3. A fast protein liquid chromatography (FPLC) spectrum of the pine cone extract of Phase 1 is given in FIG. 1. An UV/VIS absorption spectrum of the pine cone extract of Phase 1 is given in FIG. 2.

TABLE 3

Molecular weights of pine cone extract main components

| Component nr. | Extract of Phase 1 [kDa] | Extract of Phase 2 [kDa] |
|---|---|---|
| 1 | >30 | >30 |
| 2 | 21.0 | — |
| 3 | 13.5 | — |
| 4 | 3.6 | — |
| 5 | 2.1 | — |

Example 4

Preparation of Peripheral Blood Mononuclear Cells

This example illustrates the preparation of peripheral blood mononuclear cells (PBMC).

Peripheral blood mononuclear cells are isolated from buffy coats. Buffy coats are the retrieved white cell layer after centrifugation of donated units of whole blood. The PBMC are harvested over a density gradient (Histopaque 1.077, Sigma Chemical Company). The PBMC are recovered from the gradient and washed with phosphate buffered saline (PBS, see Sambrook J C et al., "Molecular Cloning: A Laboratory Manual", Cold Spring Harbor Laboratory Press 1989), pH 7.4. After washing, the cells are suspended in an augmented RPMI 1640 complete medium comprising standard RPMI 1640 medium as defined in Moore, G E, Gerner, R E, and Franklin, H A (1967) A.M.A. Vol. 199, page 519, and additionally 10% fetal calf serum, 100 units/ml penicillin, 100 µg/ml streptomycin and 50 µM 2-mercaptoethanol. The final cell concentration is adjusted to be $2 \times 10^6$ cells/ml. Of these, $CD14^+$ and $CD3^+$ cells were isolated with CD14 or CD3 microbeads (Miltenyi Biotech, Auburn, Calif.), respectively, according to the manufacturer's instructions. The isolated cells are checked to be more than 95% $CD14^+$ and $CD3^+$, respectively, as determined by immunofluorescent staining.

Example 5

Exposition of PBMC With Pine Cone Extracts

This example illustrates morphological changes induced by exposition of PBMC to pine cone extracts.

PBMC of example 4 with a cell concentration of $2 \times 10^6$ cells/ml in augmented RPMI 1640 medium (medium definition as in example 4) are distributed to the wells of 96 well flat-bottom microtitration plates (Nunc) with 100 µl cell suspension per well. Pine cone extracts of methods 1 and 2 (examples 1 and 2, respectively) are added to each well to a final concentration of 0, 6.25, 12.5, 25, 50, 100 and 300 µg/ml, respectively.

Figure 3:
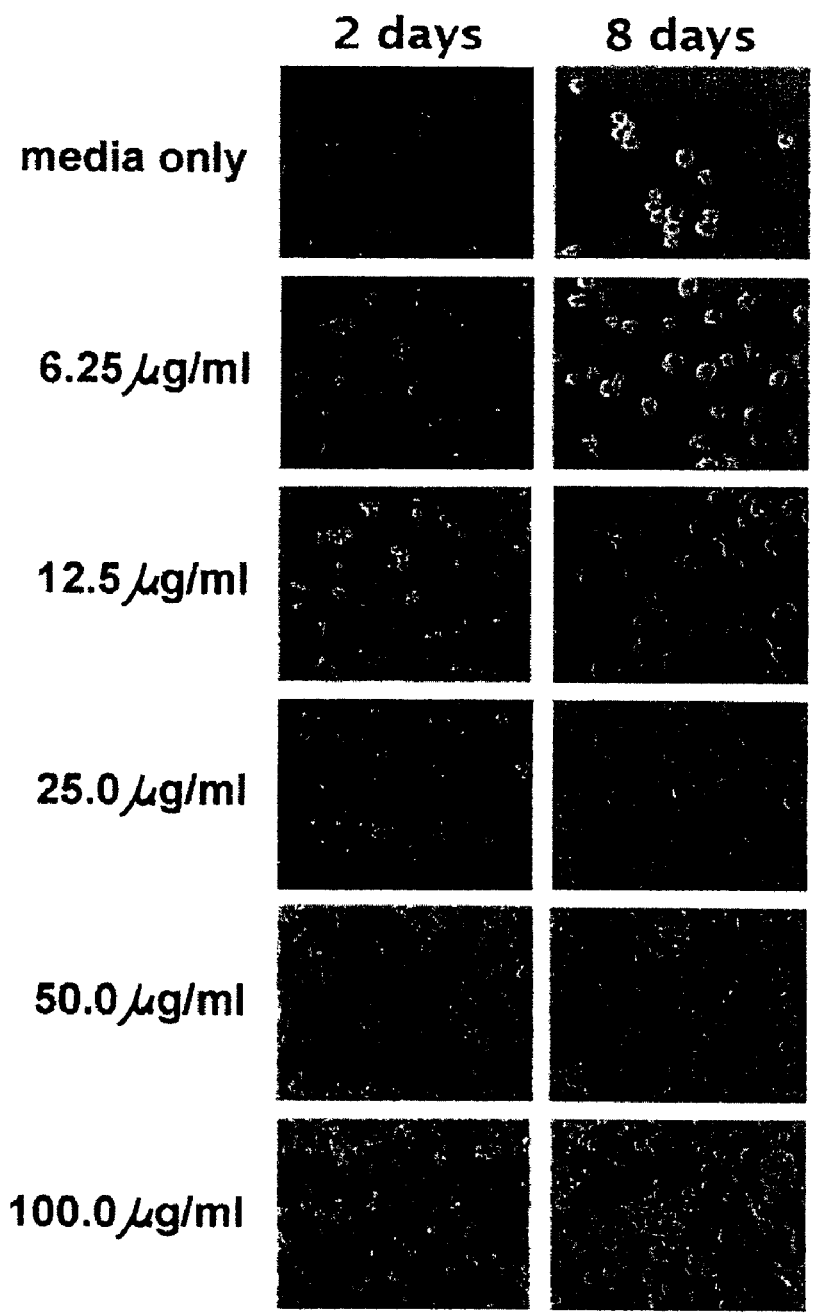
FIG. 3 shows phase contrast microscopy of PBMC exposed to varying concentrations of pine cone extracts of Phase 1, Example 1.

The cells are cultivated for up to 8 days at 37° C. in an atmosphere comprising 5% $CO_2$. FIG. 3 shows a typical phase contrast microscopy image of PBMC exposed to varying concentrations of pine cone extracts of Phase 1. Clearly, a marked increase in cell number roughly proportional to pine cone extract concentration is visible. Furthermore, cell morphology changes from disk shaped PBMC morphology to dendritic cell morphology upon exposure to pine cone extract; this effect is best visible at higher concentrations (12.5-100 and 8 days exposure time, but can already be seen at these concentrations on day 2. No visible differences were detected between PBMC exposed to pine cone extracts of Phase 1 and PBMC exposed to pine cone extracts of Phase 2 (images not shown).

Example 6

Effects of Cytokines and Pine Cone Extracts on PBMC

This example illustrates the effects on PBMC caused by exposition to cytokines and pine cone extracts.

500 µl of PBMC of example 4 (cell concentration: $2 \times 10^6$ cells/ml) are distributed each into the wells of a first 24 well tissue culture plate (Nunc). Then, to each well 500 µl of augmented RPMI 1640 medium (see example 4) are added, wherein the media samples added comprise (=concentrations in media added, not final concentrations!) either no extra substances, 200 µg/ml GM-CSF, 20 ng/ml IL-4, 20 ng/ml TNFα or 200 µg/ml PCE of Phase 1. After 72 h (initial cultivation) the non adherent cells are harvested and placed in wells of a second 24 well plate. To each of these wells 500 µl of augmented RPMI 1640 medium (see example 4) with pine cone extract of Phase 1 at a concentration of 200 µg/ml PCE (final concentration 100 µg/ml PCE) is added. After 48 h of cultivation (second cultivation) the non-adherent cells are removed. The adherent cells were washed with PBS (see example 4) and photographed under phase contrast microscopy.

Figure 4:
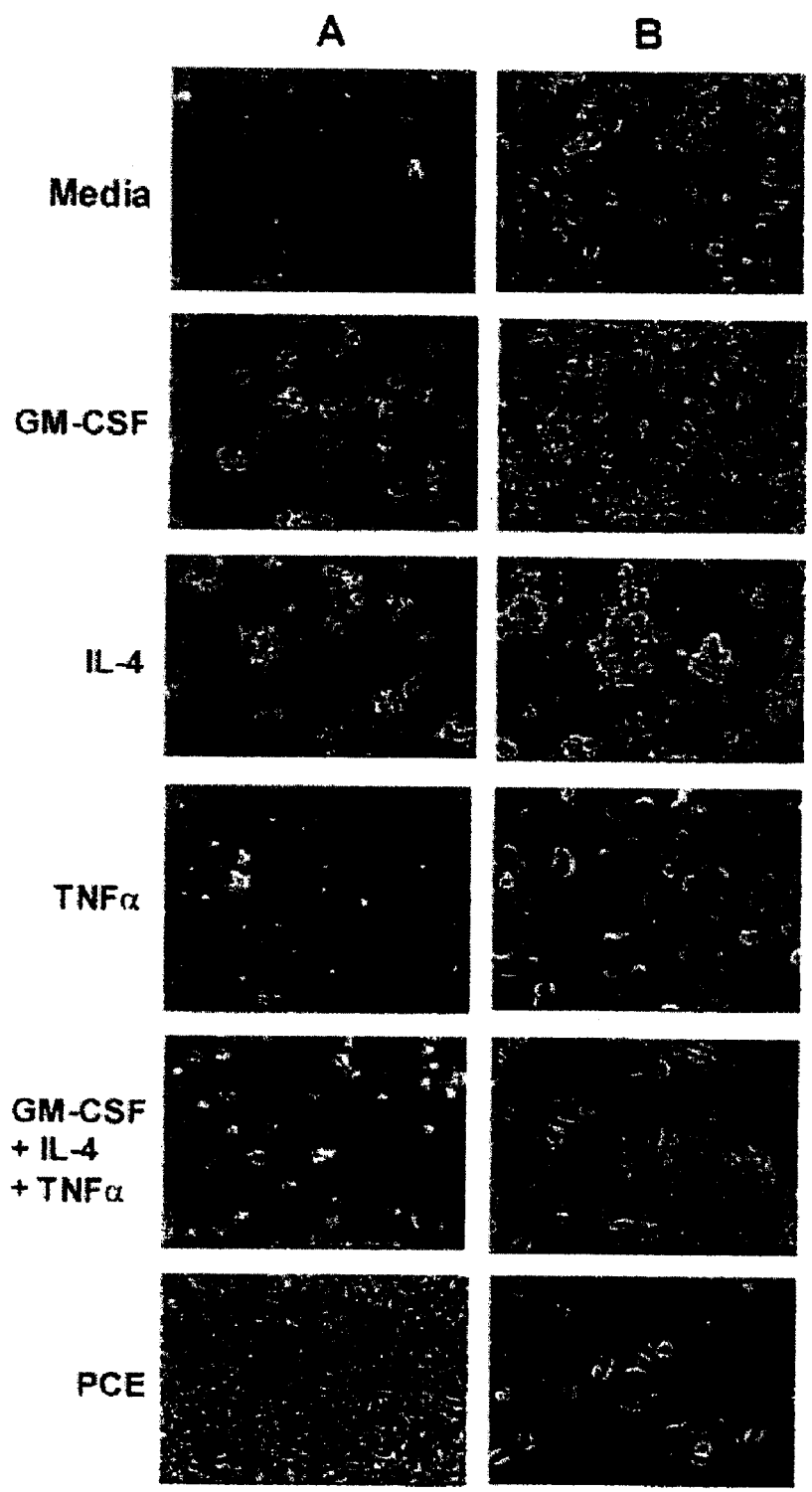
FIG. 4 shows phase contrast microscopy of PBMC exposed to cytokines and pine cone extract of Phase 1, Example 1.

FIG. 4 shows phase contrast microscopy images of PBMC exposed to the cytokines and pine cone extract of Phase 1. Images of column A show adherent cells after 72 h of exposure to cytokines or PCE. Images of column B show adherent cells generated by second cultivation from the fraction of non-adherent cells obtained after initial cultivation. The images show that exposition of PBMC to either one of the cytokines tested still allows for a considerable increase in adherent cells by exposure to PCE. They also show that the effect of exposure of PBMC to pine cone extract is similar to that of exposure of PBMC to a cytokine combination known to induce differentiation into dendritic cells. No differences were observed between effects of pine cone extracts of Phase 1 and pine cone extracts of Phase 2.

Example 7

Generation of Dendritic Cells by Conventional Method

This example illustrates a conventional method of inducing differentiation of PBMC to dendritic cells by exposition to cytokines.

PBMC of example 4 are cultured for 5 days in augmented RMPI 1640 medium (medium definition as in example 4) with additional 100 ng/ml human GM-CSF (R&D Systems, Minneapolis, cat. no. 215-GM-005) and 10 ng/ml IL-4 (R&D Systems, Minneapolis, cat. no. 204-IL-005). Cells are then cultivated for at least 3 days in RMPI 1640 medium as above with additional 10 ng/ml. TNFα (R&D Systems, Minneapolis, cat. no. 210-TA-010).

Example 8

Detection of Cytokine Production by PBMC Exposed to Pine Cone Extracts

This example illustrates the changes in cytokine production of PBMC caused by exposure to the pine cone extract of Phase 1.

PBMC are exposed to increasing concentrations of pine cone extract of Phase 1 as detailed in example 5. Cytokine production is then analyzed by ELISA. ELISAs were performed using the supernatants from 48 hr cultures of PBMC that had been treated with increasing doses of PCE. The ELISAs to detect the following cytokines, GM-CSR (cat# DGM00), IL-1β (cat#DLB50), IL-6 (cat# D6050), and TNFα (cat# DTA50), were performed according to the manufacturer's instructions (R&D Systems, Minneapolis, Minn.). Essentially, 100 µl of the culture supernatant was added to appropriate wells in the 96 well plate provided in the ELISA kit and incubated at room temperature for 2 hours. The wells were washed with the wash buffer provided and then blotted dry. Next, biotinylated antibody specific for the cytokine was added to the well and incubated at room temperature for 2 hours. The wells were washed and blotted dry. Streptavidin-conjugated horseradish peroxidase was added to each well for 20 minutes and then detected using tetramethylbenzidine in hydrogen peroxide as the substrate. After 30 minutes the reaction was terminated by the addition of an acidic solution and the absorbance of the mixture at 450 nm was measured using a plate spectrophotometer (Molecular Devices, Mountainview, Calif.)

Figure 5:
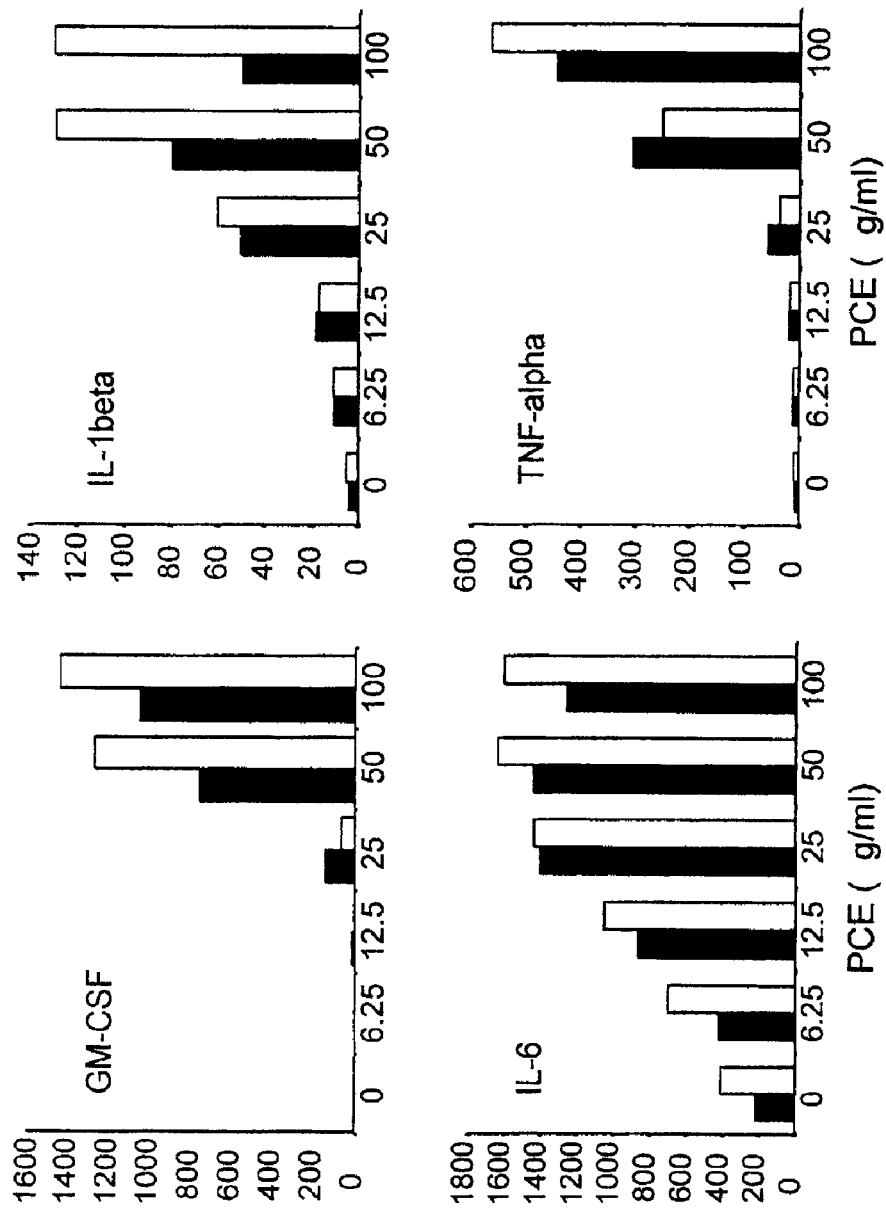
FIG. 5 shows pine cone extract induced production of cytokines in cultures of PBMC derived from two different blood donors.

FIG. 5 shows pine cone extract induced production of cytokines in cultures of PBMC derived from two different blood donors. Cytokine production data of one donor is consistently given in black bars, whereas data of the other donor is given in light bars. The diagrams show pine cone induced production of GM-CSF (upper left diagram), IL-1β (upper right diagram), IL-6 (lower left diagram) and TNFα (lower right diagram). Final pine cone extract concentration in the cultivation media is given in µg/ml. The diagrams show a general increase in cytokine production roughly proportional to pine cone extract concentration during exposure. The inventors could not detect IL-4 or IL-10 in the media (data not shown). No differences in cytokine expression were observed between cells exposed to pine cone extracts of Phase 1 and cells exposed to pine cone extracts of Phase 2.

Example 9

Activation of Naïve Allogeneic T Cells by CD14+ Cells Exposed to Pine Cone Extracts This example illustrates the ability of CD14+ having been exposed to pine cone extracts of Phase 1 to activate naïve allogeneic CD3+ cells.

A pure population of phenotypically dendritic cells is derived from PBMC of example by extraction with magnetic beads (CD14+ Miltenyi Biotech, Auburn Calif., cat #502-01) according to the manufacturer's instructions.

The thus isolated CD14+ cells are distributed into the wells of a 6 well tissue culture plate (Nunc) and exposed to augmented RPMI 1640 medium as defined in example 4 with a pine cone extract of Phase 1 at a final concentration of 100 µg/ml for 8 days. The cells differentiate into phenotypically dendritic cells as described in example 5.

The remaining non-adherent cells are removed. The phenotypically dendritic cells are harvested (see example 5), transferred to fresh augmented RPMI 1640 medium as defined in example 4 and distributed in 100 µl volumes into the wells of a 96 well round bottom tissue culture plate (Nunc) to final varying concentrations of phenotypically dendritic cells per well.

Naïve allogeneic and autologous CD3+ cells are obtained by using CD3+ microbeads (Miltenyi Biotech) according to the manufacturers instructions.

The CD3+ cells are harvested and distributed in augmented RPMI 1640 medium as defined in example 4 in 100 µl volumes to the phenotypically dendritic cells on the second tissue culture plate to a final concentration of $10^5$ CD3+ cells per well. The mixed cells were coincubated for 3 days. After 3 days, concentrations of IFN-gamma are determined by ELISA (R&D Systems, Minneapolis, cat. no. DIF50) according to manufacturer's instructions.

Figure 6:
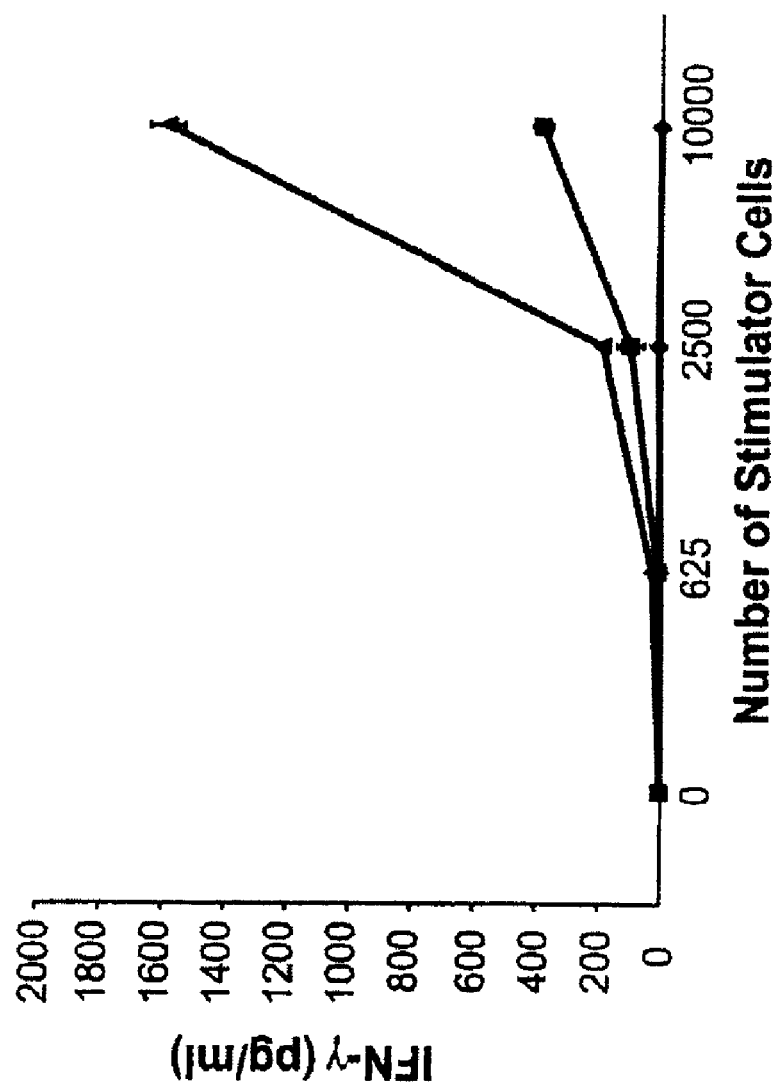
FIG. 6 shows interferon gamma production by allogeneic and autologous $CD3^+$ cells upon coincubation with varying concentrations of $CD14^+$ cells having been exposed to pine cone alkaline extracts of Phase 1, Example 1.

FIG. 6 shows IFN-gamma production by allogeneic and autologous CD3+ cells determined after coincubation. Triangles show IFN-gamma concentrations after coincubation of CD3+ cells with dendritic cells that were obtained as described in example 7. Squares show IFN-gamma concentrations after coincubation with phenotypically dendritic cells as described above (prepared in the presence of PCE). Diamonds show IFN-gamma concentrations of CD3+ cells incubated with PBMC exposed to media only. Dendritic cells as obtained by the method described in example 7 are most effective in stimulating IFN-gamma production. Phenotypically dendritic cells obtained by the method described above are significantly more effective in stimulating IFN-gamma production than is medium alone, but are less effective than dendritic cells as obtained by the method of example 7. No significant differences in effect were observed between use of pine cone extracts of Phase 1 and 2 (data not shown).

Cells obtained by exposure to pine cone extracts appear to be immature and not fully mature dendritic cells.

Example 10

Adjuvant Activity of Pine Cone Extract in an HIV DNA (gag) Vaccine Model

This example illustrates the effects of pine cone administration in a DNA vaccination procedure. Balb/c mice are injected intramuscularly in each quadriceps with 50 µg of vaccine DNA, suspended in 50 µl PBS or suspended in 50 µl of a 40 µg/ml pine cone extract composition of Phase 1 (co-injection). Vaccine DNA is a plasmid vector expressing HIV gag as immunogen, viz pCIgag. Control DNA is a plasmid vector expressing CAT, viz pCICAT. In another treatment group, Balb/c mice were supplied 200 µg/ml pine cone extract in their drinking water for the duration of the experiment. These mice were also vaccinated with the plasmid vectors as described above.

Three weeks after vaccination, the vaccinated mice are challenged with an intravenous injection of $3 \times 10^6$ pfu of a vaccinia expression vector expressing HIV gag. 3 days after this challenge, the mice are killed, their spleens are harvested and their splenocytes are isolated by common techniques, see Bradley, W. G., Ogata, N., Good, R. A., and N. K. Day; "Alteration of in vivo cytokine gene expression in mice infected with a molecular clone of the defective MAIDS virus", 1994, J. Acquired Immune Deficiency Syndromes. 7:1-9.

The splenocytes are washed with PBS (see example 5), pelleted by low speed centrifugation and then suspended in ice cold PBS containing 2% w/w heat inactivated fetal calf serum and placed on ice for 15 min. Then, the appropriate antibodies recognizing $CD4^+$ or $CD8^+$ and IFN-gamma are added to the cells. Cells and antibodies are incubated for 30 min on ice in the dark to label the cells. The cells are then washed with ice cold PBS. The washed cells are fixed in 1 ml freshly prepared 1% w/w aqueous paraformaldehyde. The labeled and fixed cells are analyzed for antigen expression using a Becton Dickinson FACS Caliber flow cytometer. A minimum of 10,000 events is collected for analysis.

Figure 7:
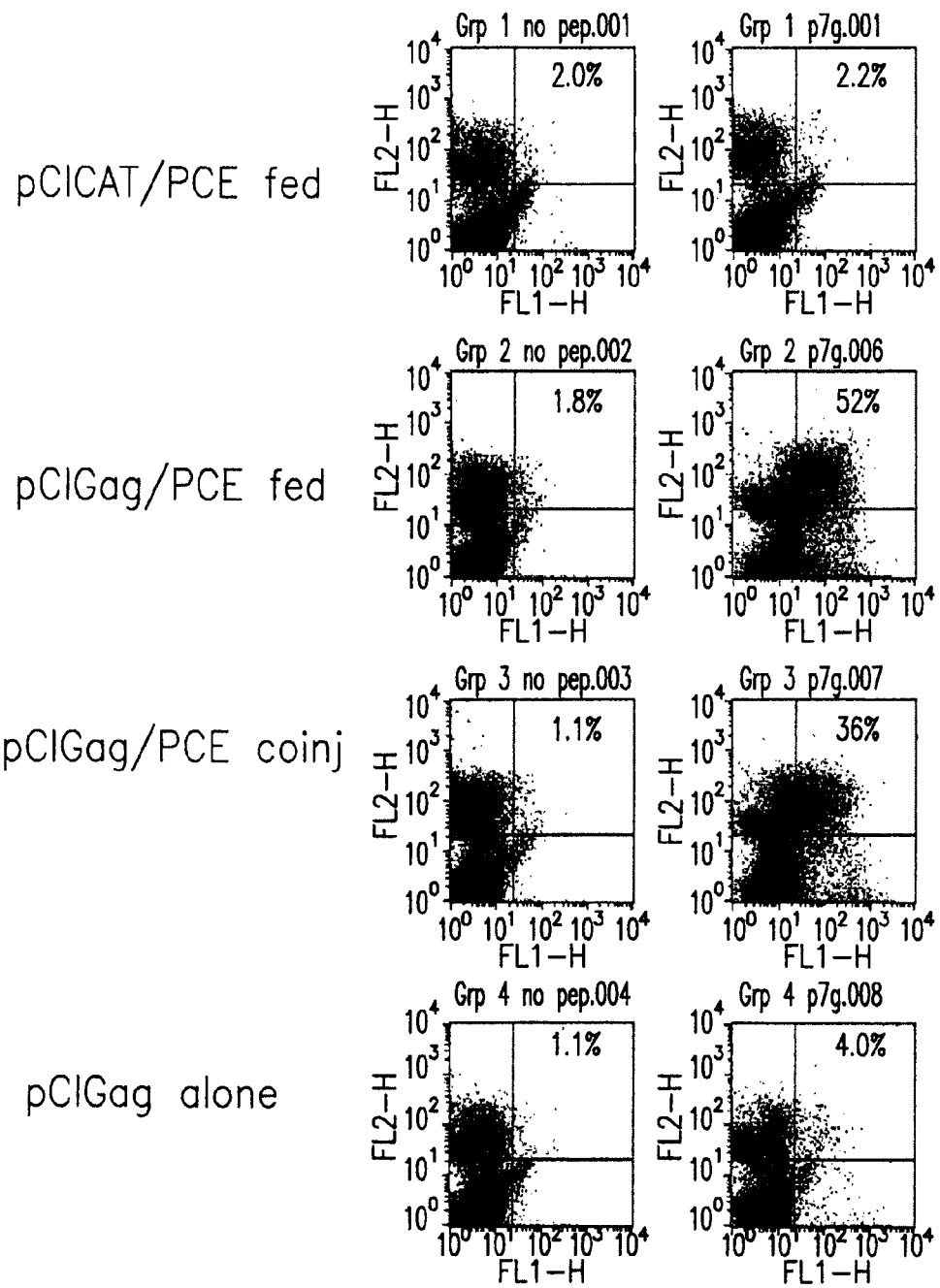
FIGS. 7 and 8 show effects of pine cone alkaline extracts on intracellular IFN-gamma production by $CD8^+$ and $CD4^+$ splenocytes of animals vaccinated with DNA vaccines.
Figure 8:
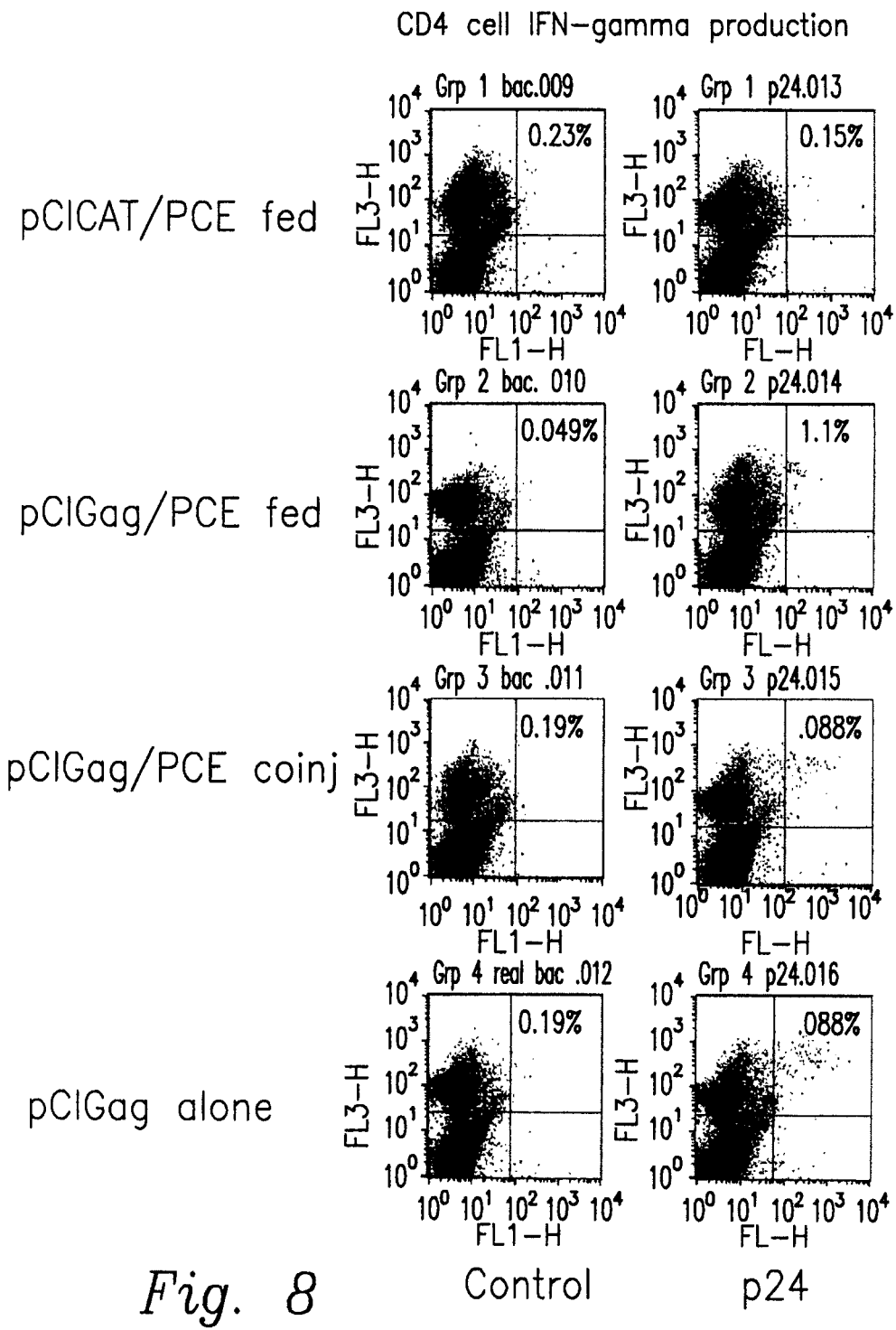

FIGS. 7 and 8 show the effect of pine cone administration on vaccination effects measured by IFN-gamma production by murine $CD8^+$ and $CD4^+$ splenocytes. The peptide portion of HIV p7g is a stimulant that T cells recognize, specifically $CD8^+$ T cells. Recombinant p24=gag=whole gag protein is the stimulant and is recognized by $CD4^+$ T cells. The response to p24 is optimal for $CD4^+$ T cells. The data show that both oral and intramuscular administration of pine cone extracts during or immediately after vaccination with a nucleic acid vaccine enhances the activation of $CD8^+$ cells (panels "pCIGag/PCE fed" and "pCIGag/PCE coinj"). The enhancement is stronger than for vaccine (pCIGag) administered without pine cone extract adjuvant (panel "pCIGag alone") or control "vaccination" DNA (panel "pCICAT/PCE fed"). Again, no significant differences are observed between pine cone extracts obtained according to Phase 1 and Phase 2.

Example 11

Preparation of Alkaline Extracts from Various Plants

Approximately thirty grams of bark and leaf were cut from each local plant species and saved in labeled bags. All samples were then cut into 1 cm squares with a sterilized blade. Fresh weight was measured immediately after the 1 cm squares were made. The squares were dried overnight (or longer depending on leaf moisture content) under hood. The dry weight was then recorded immediately after.

The following steps were performed with strict sterility. Prior to addition of plant matter, 100 mL of 1% w/v KOH was prepared in an autoclaved, endotoxin-free 250 ml beaker (i.e. 10 mL 50% KOH in 490 mL ultraPURE Distilled Water). The resulting volume ratio between plant material and 1% KOH solution was 1:8.

The plant matter/1% KOH mixture was then placed in an autoclave set at 121° C. for 1 hr in the liquid cycle. After extraction, the beaker was removed and allowed to cool to room temperature. The contents of the beaker were poured through a 70 µm cell strainer atop a 50 ml centrifuge tube to the 45 ml mark and repeated in another 50 ml tube (the volume can be recorded as approximate volume of plant matter). The tubes were then poured into 150 ml endotoxin-free ungraduated glass media bottles.

3 ml of the extract was removed and added to a 15 ml centrifuge tube to determine the starting pH. Small amounts (i.e. 20 µl) of 5N HCl or 1% KOH were added and mixed into the extract. 3 ml of the extract was then removed and pH was rechecked. Addition of small amounts of 5N HCl or 1% KOH was repeated until a pH of 8.0+/−0.2 was reached.

The plant matter extract was then autoclaved at 121° C. for 20 minutes. The bottles were allowed to cool to room temperature and 20 µl was removed and added to 10 ml of distilled water. 200 µl was removed from the vortexed dilution and added to a 96 well U.V. plate for measuring the O.D. of the prepared extract.

Using the Biotek µquant plate reader and K4 software the plate was read at 280 nm and 232 nm with the path length correction feature selected.

Using the following equation, lignin concentration was determined: Lignin Conc. (mG/ml)=0.0625*(O.D. 280 corr.) *(Dilution factor). The concentration was then adjusted with ULTRAFree distilled water to approximately 10 mG/ml of lignin for long term storage.

The bottles with freshly prepared PPC extract were then autoclaved at 121° C. for 20 minutes for sterility and saved at room temperature until the bottle was opened, then it was refrigerated. Table 4 summarizes data on alkaline extracts obtained from 12 different plants.

TABLE 4

Preparation of PPC Extracts from Different Plants

| Plant Matter 1% KOH Lot # 02 2205 | Approximate Volume of Extract Post PH | O.D. Original 280 corr. | O.D. Original 232 corr. | Original Lignin Concentration |
|---|---|---|---|---|
| Loquat | 32.03 | 0.735 | 1.199 | 22.97 |
| Lipton Loose Tea (pekoe and pekoe) | 42.8 | 1.798 | 2.403 | 56.19 |
| Japanese Black Pine (leaves-needles) | 53.555 | 0.927 | 1.843 | 28.66 |
| Japanese Black Pine (bark) | 21.02 | 1.21 | 2.08 | 37.81 |
| Mountain Araucaria (leaves-needles) | 59.61 | 0.829 | 1.444 | 25.91 |
| Mountain Araucaria (bark) | 40.51 | 1.683 | 2.443 | 52.59 |
| Southern Magnolia (leaves) | 48.965 | 0.529 | 0.95 | 16.53 |
| Golden Goddess Bamboo (stalk) | 59.905 | 0.654 | 1.048 | 20.44 |
| Golden Goddess Bamboo (sheath) | 51.02 | 0.516 | 0.763 | 16.13 |
| Sargent Juniper (leaves-needles) | 50.085 | 0.731 | 1.271 | 22.84 |
| Bushy Bluestem (leaves) | 38.545 | 10.27 | 1.71 | 32.09 |

TABLE 4-continued

Preparation of PPC Extracts from Different Plants

| | | | | |
|---|---|---|---|---|
| Loblolly pine (leaves-needles) | 31.032 | 10.65 | 1.826 | 33.28 |
| Loblolly pine (female cone) | 32.04 | 1.143 | 1.957 | 35.72 |
| Scrub palm (leaves) | 70.51 | 0.749 | 1.35 | 23.41 |
| Spanish moss (whole plant) | 43.534 | 0.695 | 1.161 | 21.72 |
| Slash pine (leaves-needles) | 36.5 | 1.064 | 2.14 | 36.38 |
| Slash pine (female cone) | 41.05 | 10.98 | 1.86 | 34.31 |
| Slash pine (bark) | 47.04 | 1.759 | 3.064 | 54.97 |

| Plant Matter 1% KOH Lot # 02 2205 | Final Approximate volume of Extract | O.D. Final 280 corr. | O.D. Final 232 Corr. | Final conc. Lignin | Lignin yield in grams | % Yield of lignin |
|---|---|---|---|---|---|---|
| Loquat | 73.57 | 0.35 | 0.595 | 10.94 | 0.80 | 6.44 |
| Lipton Loose Tea (pekoe and pekoe) | 240.48 | 0.428 | 0.638 | 13.38 | 3.22 | 25.73 |
| Japanese Black Pine (leaves-needles) | 153.47 | 0.369 | 0.753 | 11.53 | 1.77 | 14.16 |
| Japanese Black Pine (bark) | 79.48 | 0.33 | 0.605 | 10.31 | 0.82 | 6.56 |
| Mountain Araucaria (leaves-needles) | 154.43 | 0.322 | 0.594 | 10.06 | 1.55 | 12.43 |
| Mountain Araucaria (bark) | 216.03 | 0.328 | 0.549 | 10.25 | 2.18 | 17.47 |
| Southern Magnolia (leaves) | 80.95 | 0.332 | 0.617 | 10.38 | 0.84 | 6.72 |
| Golden Goddess Bamboo (stalk) | 122.43 | 0.315 | 0.537 | 9.84 | 1.21 | 9.64 |
| Golden Goddess Bamboo (sheath) | 82.27 | 0.341 | 0.531 | 10.66 | 0.88 | 7.01 |
| Sargent Juniper (leaves-needles) | 114.41 | 0.35 | 0.636 | 10.94 | 1.25 | 10.01 |
| Bushy Bluestem (leaves) | 123.71 | 0.355 | 0.627 | 11.09 | 1.37 | 10.98 |
| Loblolly pine (leaves-needles) | 103.28 | 0.441 | 0.786 | 13.78 | 1.42 | 11.39 |
| Loblolly pine (female cone) | 114.44 | 0.348 | 0.631 | 10.88 | 1.24 | 9.96 |
| Scrub palm (leaves) | 165.04 | 0.363 | 0.665 | 11.34 | 1.87 | 14.98 |
| Spanish moss (whole plant) | 94.55 | 0.31 | 0.547 | 9.69 | 0.92 | 7.33 |
| Slash pine (leaves-needles) | 132.77 | 0.408 | 0.775 | 12.75 | 1.69 | 13.54 |
| Slash pine (female cone) | 140.85 | 0.31 | 0.559 | 9.69 | 1.36 | 10.92 |
| Slash pine (bark) | 258.57 | 0.266 | 0.499 | 8.31 | 2.15 | 17.20 |

Example 12

Further Filtration and Separation Methods of Alkaline Extracts Prepared from Plants The plant extracts prepared according to a protocol of Example 11 were further fractioned into >10 kDa and <10 kDa fractions. The fractionation was carried out using Amicon centricon columns Ym-10 Lot #L4DN4673A. Ultra pure DNAse, RNAse free water was used in all filtration procedures.

Table 5 provides lignin concentrations for >10 kDa and <10 kDa fractions of alkaline extracts prepared from various plants in comparison to lignin concentration of the original non-fractionated extract for each of the plants.

TABLE 5

Lignin Concentration In >10 Kda and <10 Kda Fractions of Alkaline Extracts Prepared from Various Plants

| | Original, Non-fractioned | | | >10 kda Fraction | | | <10 Kda Fraction | | |
|---|---|---|---|---|---|---|---|---|---|
| Plant | 280 Corr. | 232 Corr. | Lignin | 280 Corr. | 232 Corr. | Lignin | 280 Corr. | 232 Corr. | Lignin |
| Loquat | 0.350 | 0.595 | 10.94 | 0.264 | 0.481 | 8.25 | 0.299 | 0.511 | 4.67 |
| Lipton Loose Tea(Pekoe and Pekoe) | 0.428 | 0.638 | 13.38 | 0.267 | 0.474 | 8.34375 | 0.395 | 0.51 | 6.17 |
| Japanese Black Pine (Leaves-needles) | 0.369 | 0.753 | 11.53 | 0.296 | 0.604 | 9.25 | 0.383 | 0.703 | 5.98 |
| Japanese Black Pine (Bark) | 0.330 | 0.605 | 10.31 | 0.212 | 0.401 | 6.625 | 0.221 | 0.408 | 3.45 |
| Mountain Araucaria (Leaves-needles) | 0.322 | 0.594 | 10.06 | 0.206 | 0.395 | 6.4375 | 0.306 | 0.544 | 4.78 |
| Mountain Araucaria (Bark) | 0.328 | 0.549 | 10.25 | 0.279 | 0.484 | 8.71875 | 0.271 | 0.408 | 4.23 |
| Southern Magnolia (Leaves) | 0.332 | 0.617 | 10.38 | 0.197 | 0.379 | 6.15625 | 0.419 | 0.794 | 6.55 |
| Golden Goddess Bamboo (Stalk) | 0.315 | 0.537 | 9.84 | 0.187 | 0.378 | 5.84375 | 0.389 | 0.624 | 6.08 |
| Golden Goddess Bamboo (sheath) | 0.341 | 0.531 | 10.66 | 0.176 | 0.353 | 5.5 | 0.437 | 0.619 | 6.83 |
| Sargent Juniper (Leaves-needles) | 0.350 | 0.636 | 10.94 | 0.274 | 0.488 | 8.5625 | 0.426 | 0.759 | 6.66 |
| Bushy Bluestem(Leaves) | 0.355 | 0.627 | 11.09 | 0.265 | 0.479 | 8.28125 | 0.353 | 0.593 | 5.52 |
| Loblolly pine (Leaves-needles) | 0.441 | 0.786 | 13.78 | 0.36 | 0.64 | 11.25 | 0.365 | 0.625 | 5.70 |
| Loblolly pine (Female cone) | 0.348 | 0.631 | 10.88 | 0.233 | 0.451 | 7.28125 | 0.185 | 0.337 | 2.89 |
| Scrub palm (Leaves) | 0.363 | 0.665 | 11.34 | 0.26 | 0.487 | 8.125 | 0.219 | 0.397 | 3.42 |
| Spanish moss (Whole plant) | 0.310 | 0.547 | 9.69 | 0.223 | 0.446 | 6.96875 | 0.339 | 0.609 | 5.30 |
| Slash pine (Leaves-needles) | 0.408 | 0.775 | 12.75 | 0.197 | 0.367 | 6.15625 | 0.346 | 0.612 | 5.41 |
| Slash pine (Female cone) | 0.310 | 0.559 | 9.69 | 0.275 | 0.535 | 8.59375 | 0.331 | 0.577 | 5.17 |
| Slash pine (Bark) | 0.266 | 0.499 | 8.31 | 0.256 | 0.477 | 8 | 0.224 | 0.398 | 3.50 |
| Original PPC Lot # 062397 | 0.525 | N/A | 16.41 | 0.626 | 1.155 | 19.5625 | 0.168 | 0.330 | 2.63 |

Example 13

Peripheral Blood Mononuclear Cell (PBMC) Adherence Assay for Measuring Activity of Alkaline Extract On day 1, dilutions of alkaline extract in Complete Medium were prepared at a 2× concentration to be assayed (i.e. 100 µg/ml dose should be made up at 200 µg/ml). 100 µL of alkaline extract to be assayed or media control was added per well into a 96-well flat bottom plate.

A vial of human PBMCs was thawed into 5 mL Complete Medium, centrifuged for 5 minutes at 400-500×g and re-suspended in Complete Medium for counting. PBMC was adjusted to a final concentration of $3 \times 10^6$ cells/ml and seeded at 100 µL/well for a final concentration of $3 \times 10^5$ cells/well. The plate was then incubated for approximately 72 hours at 37° C. in 5% $CO_2$ incubator.

On day 3, the plate was washed twice with Dulbecco's PBS with Calcium and Magnesium. The plate was then fixed with 100 µl/well methanol for 5 minutes at room temperature. The plate was flicked to remove methanol, 100 µl/well of 0.25% methylene blue was added and the plate was incubated for 30 minutes at room temperature.

The plate was flicked to remove methylene blue and flooded with tap water repeatedly to ensure removal of excess methylene blue. 100 µl/well of acid ethanol was added to release color for 1-2 minutes at room temperature. Absorbance was then read at 650 nm.

Following this protocol, activity of alkaline extract prepared from green tea leaves (GTX) was measured. Specifically, freshly thawed PBMCs were plated at $3 \times 10^6$/ml per well in a 96-well plate and the PPC extract was added at concentrations: 200 µg/ml, 100 µg/ml, 50 µg/ml, 25 µg/ml 12.5 µg/ml, 6.25 µg/ml or 0 µg/ml. As a control, some wells were incubated with an alkaline extract prepared from pine cones used at the same concentrations as GTX. Cells were incubated for 72 hours, then fixed and cell adherence was measured in a plate reader at 650 nm.

Figure 10:
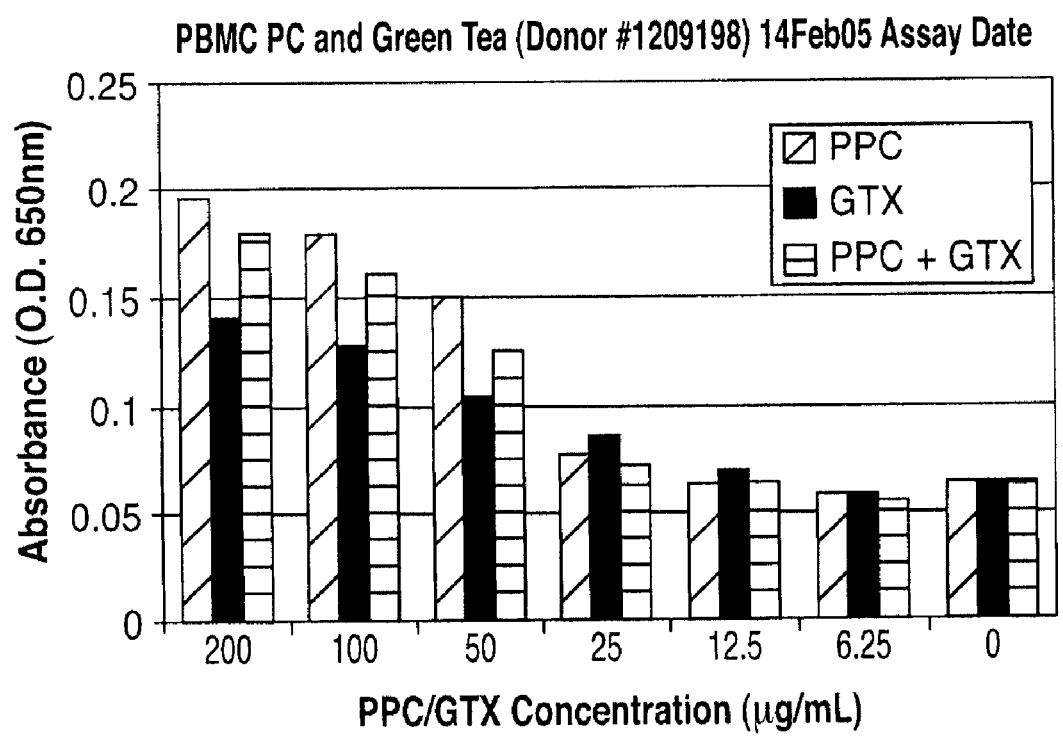
FIG. 10 shows that alkaline extracts prepared from green tea leaves (GTX) and pine cones (PPC) stimulate adherence of peripheral blood mononuclear cells (PBMCs) in a standard adherence assay.

As seen in FIG. 10, GTX stimulated adherence of peripheral blood mononuclear cells (PBMCs). The effect was concentration-dependent: cells incubated with 200 µg/ml of GTX adhered to the plate 1.5 times more efficiently than cells incubated with 50 µg/ml of GTX.

Figure 11:
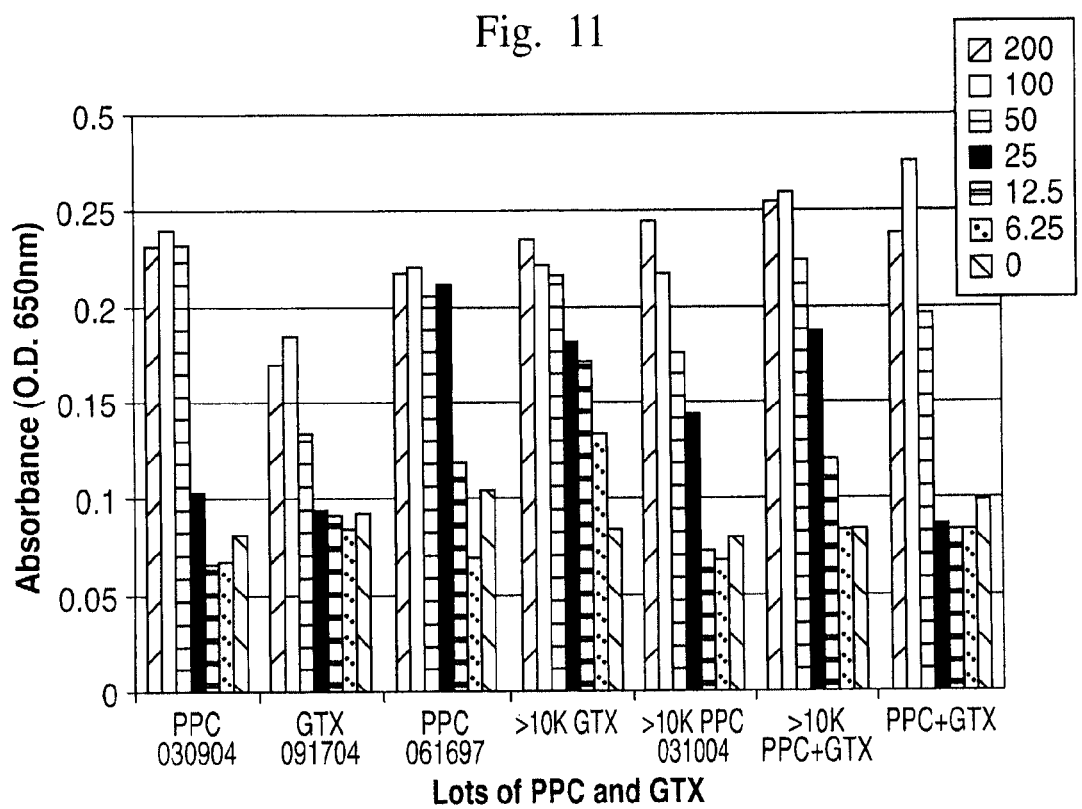
FIG. 11 shows >10 kDa fraction of alkaline extract is enriched for activity stimulating adherence of PBMCs. PBMCs were incubated either with alkaline extract from green tea leaves (GTX) or pine cones (PPC), >10 kDa fractions from the extracts or a combination of PPC and GTX preparations at concentrations 0 µg/ml, 6.25 µg/ml, 12.5 µg/ml, 25 µg/ml, 50 µg/ml, 100 µg/ml 100 µg/ml or 200 µg/ml.

In another experiment, PBMCs were incubated either with alkaline extract from green tea leaves (GTX) or pine cones (PPC) or >10 kDa fractions from the extracts at concentrations 0 µg/ml, 6.25 µg/ml, 12.5 µg/ml, 25 µg/ml, 50 µg/ml, 100 µg/ml 100 µg/ml or 200 µg/ml of each preparation or a combination of PPC and GTX preparations for 72 hours and then fixed and examined for PPBC adherence. As seen in FIG. 11, >10 kDa fraction of extract made from green tea leaves was enriched for the activity that stimulated adherence of PPBCs.

Example 14

Figure 12:
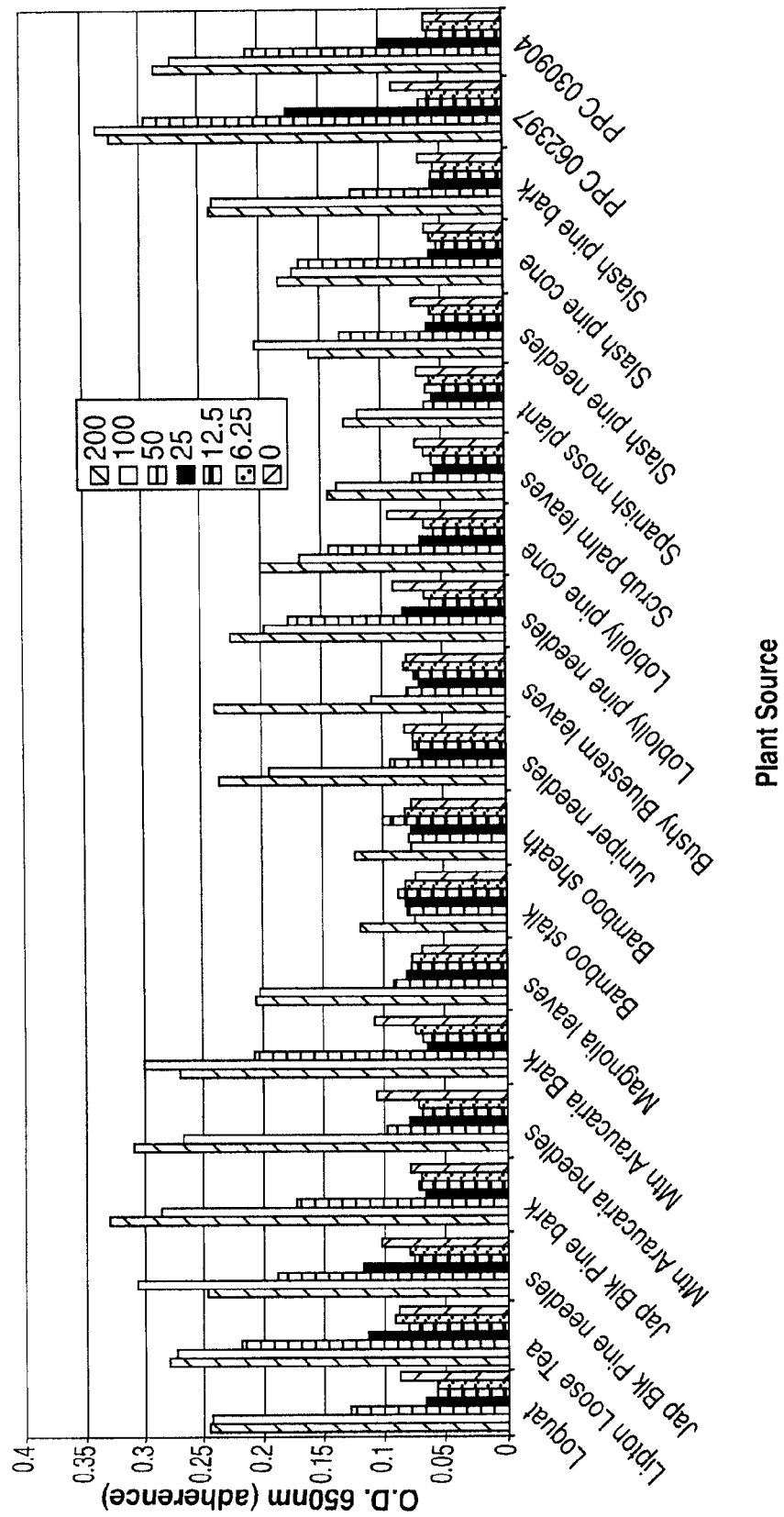
FIG. 12 shows adherence of human peripheral blood mononuclear cells 3 days post treatment with alkaline extracts made from various terrestrial plants.

Measuring Activity of Alkaline Extracts Made from Various Plants via PBMC Adherence Assay Peripheral blood mononuclear cells (PBMCs) were plated in 96-well plates and treated with PPC extracts from various plants at 0 µg/ml, 6.25 µg/ml, 12.5 µg/ml, 25 µg/ml, 50 µg/ml, 100 µg/ml 100 µg/ml or 200 µg/ml per well. As shown in FIG. 12, alkaline extract prepared from either bamboo stalk or sheath was toxic to cells, while alkaline extracts prepared from other plants were able to stimulate adherence of PBMCs to the same extent as extract made from pine cones.

Figure 13:
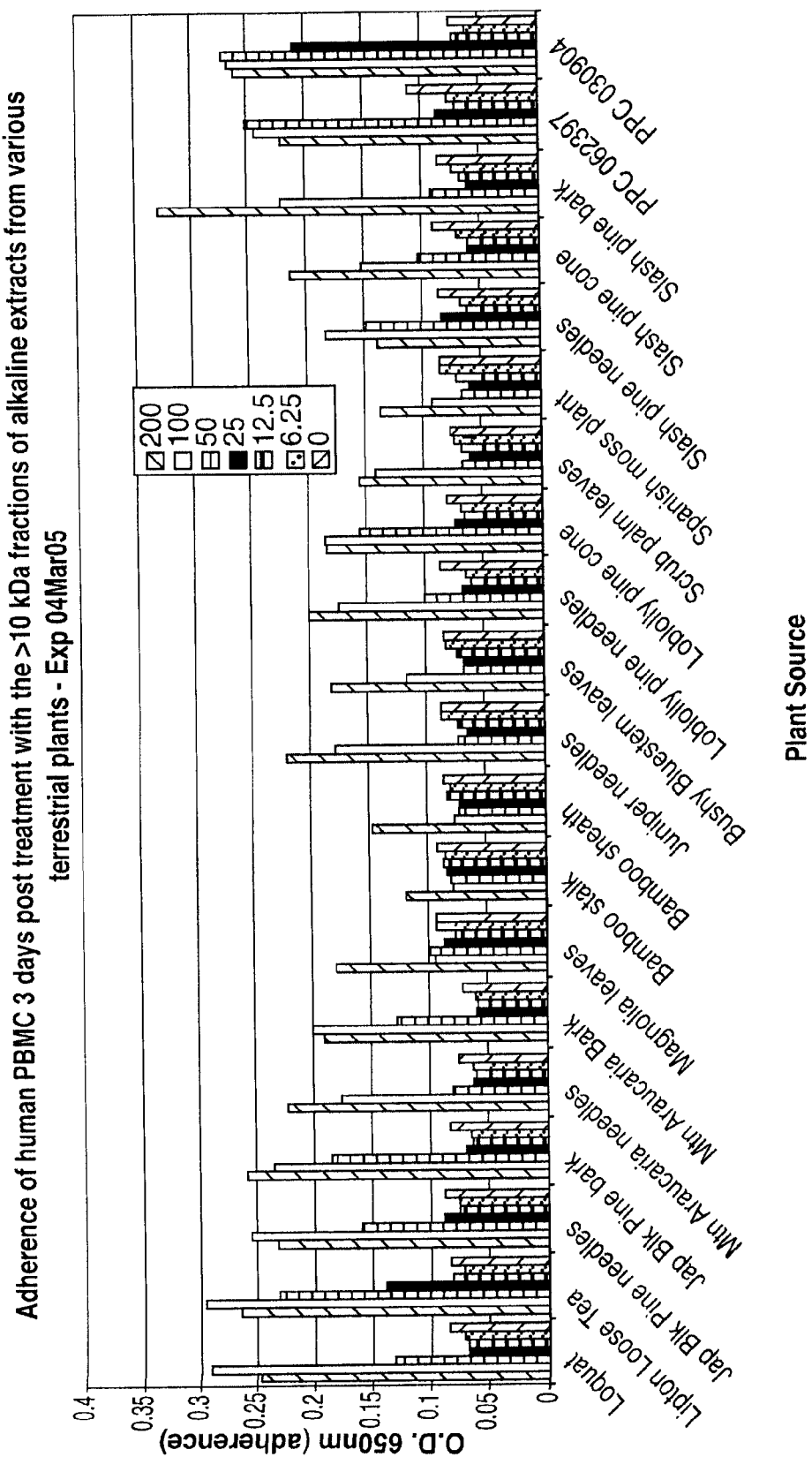
FIG. 13 shows adherence of human peripheral blood mononuclear cells 3 days post treatment with the >10 kDa fractions of alkaline extracts made from various terrestrial plants.

As shown in FIG. 13, >10 kDa fractions of alkaline extracts made from various plants (except for bamboo stalk and sheath) were enriched for activity that stimulates adherence of PBMCs.

Example 15

Analyzing Alkaline Extract from Green Tea (GTX)

Figure 14:
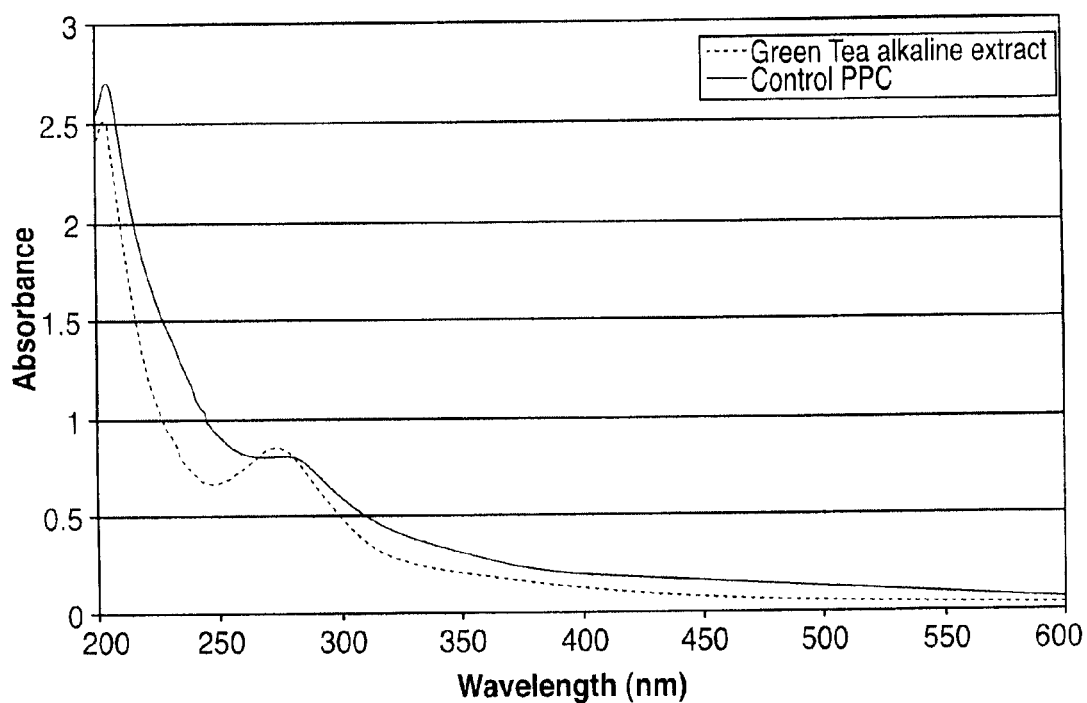
FIG. 14 shows UV-visible scan of 50 µg of unfractionated PPC and GTX.
Figure 15A:
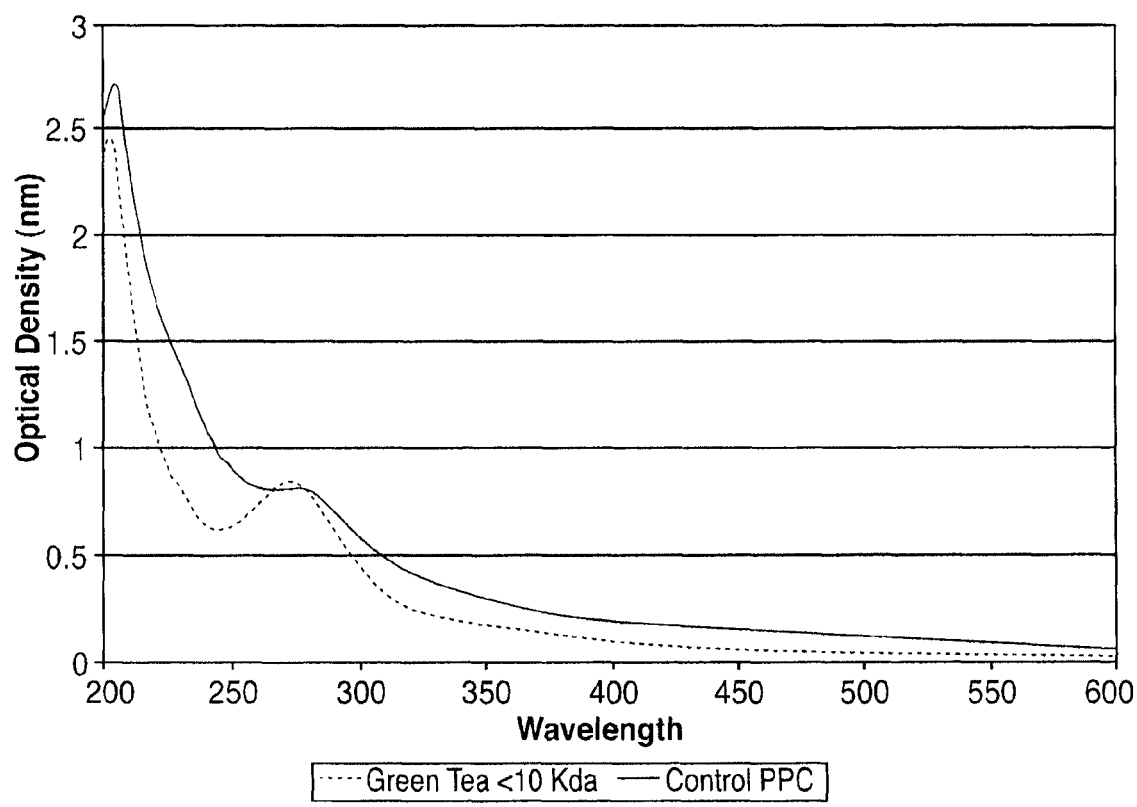
FIG. 15A shows UV-Visible scan of PPC and a GTX<10 kDa fraction at 50 µg.
Figure 15B:
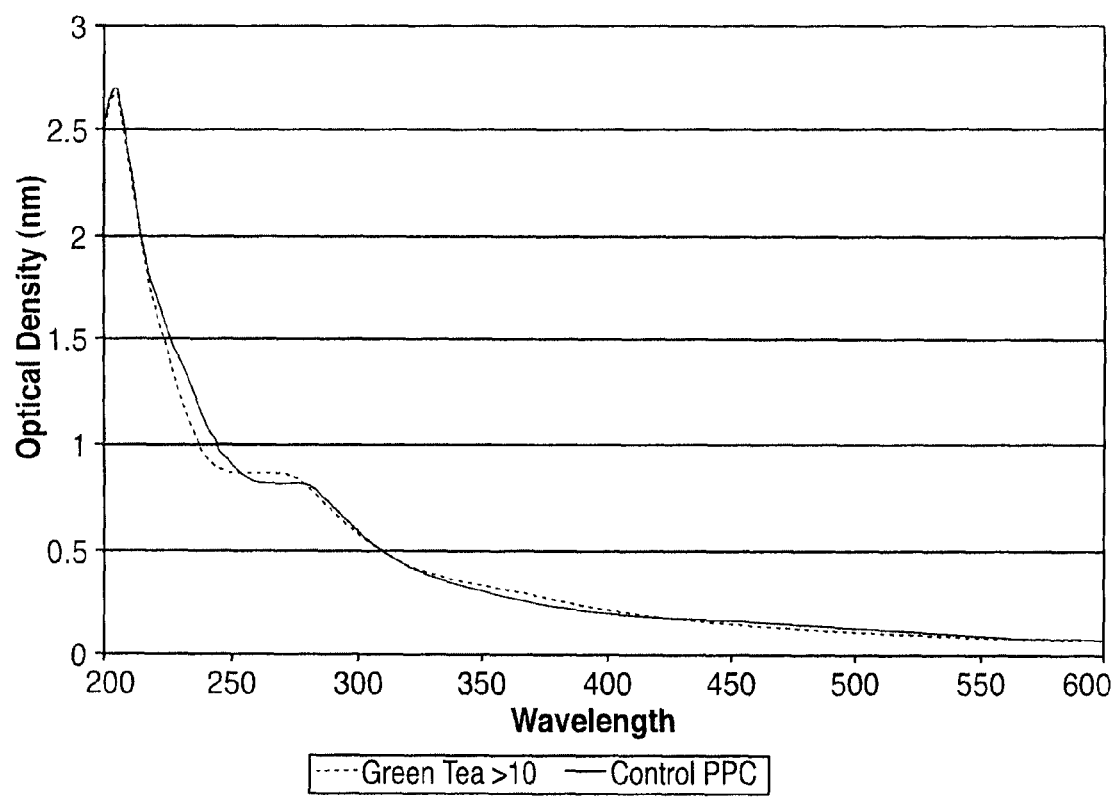
FIG. 15B shows UV-Visible scan of PPC and a GTX>10 kDa fraction at 50 µg.

Green tea leaves were extracted with 1% KOH at 121° C. for 1 hour in an autoclave with a solute to solvent ratio 1:8. Three different lots of green tea leaves were used. As shown in Table 6, lignin-containing extract was obtained from each of the three batches used for preparing GTX. The spectrum of the GTX was then examined in comparison to the spectrum of PPC prepared from pine cones (FIG. 14). GTX was then fractioned into >10 kDa and <10 kDa fractions and spectroscopic profiles of <10 kDa GTX fraction (FIG. 15A) and >10 kDa GTX fraction (FIG. 15B) were compared to a profile of a non-fractioned extract. Peak characteristic of the alkaline extract was retained in a <10 kDa GTX fraction (FIG. 15A), but disappeared from a >10 kDa GTX fraction (FIG. 15B).

TABLE 6

GTX and PPC Extraction Results.

| | Grams of Extractable Material | Milliliters of 1% KOH | pH post extraction | Lignin (mg/ml) | Final Volume | Yield | % Yield |
|---|---|---|---|---|---|---|---|
| GTX (Lot 1) | 62.5 | 500 | 8.13 | 41.03 | 175 | 7180.25 | 11.49 |
| GTX (Lot 2) | 62.5 | 500 | 8.3 | 43 | 200 | 8600 | 13.76 |
| PPC | 62.5 | 500 | 12.4 | 23.93 | 225 | 5384.25 | 8.61 |

Unfractioned GTX, <50 kDa GTX fraction and <50 kDa PPC fraction were then analyzed in the adherence assay of human PBMCs (protocol described above). In this assay, PBMCs were treated with different concentrations (from 0 µg to 200 µg) of either unfractioned GTX, the <50 kDa GTX fraction or the <50 kDa PPC fraction for 48 hours.

The results of this assay are presented in FIG. 16, which shows that PBMCs treated with 100 µg of the >50 kDa GTX fraction adhered at least seven times better to a plate in comparison to PBMCs not treated with the extract. Furthermore, PBMCs treated with the >50 kDa GTX fraction adhered to the plate as efficiently as PBMCs treated with non-fractioned extract, suggesting that most of the adherence-stimulating activity in GTX is contained in the >50 kDa GTX fraction.

Figure 17:
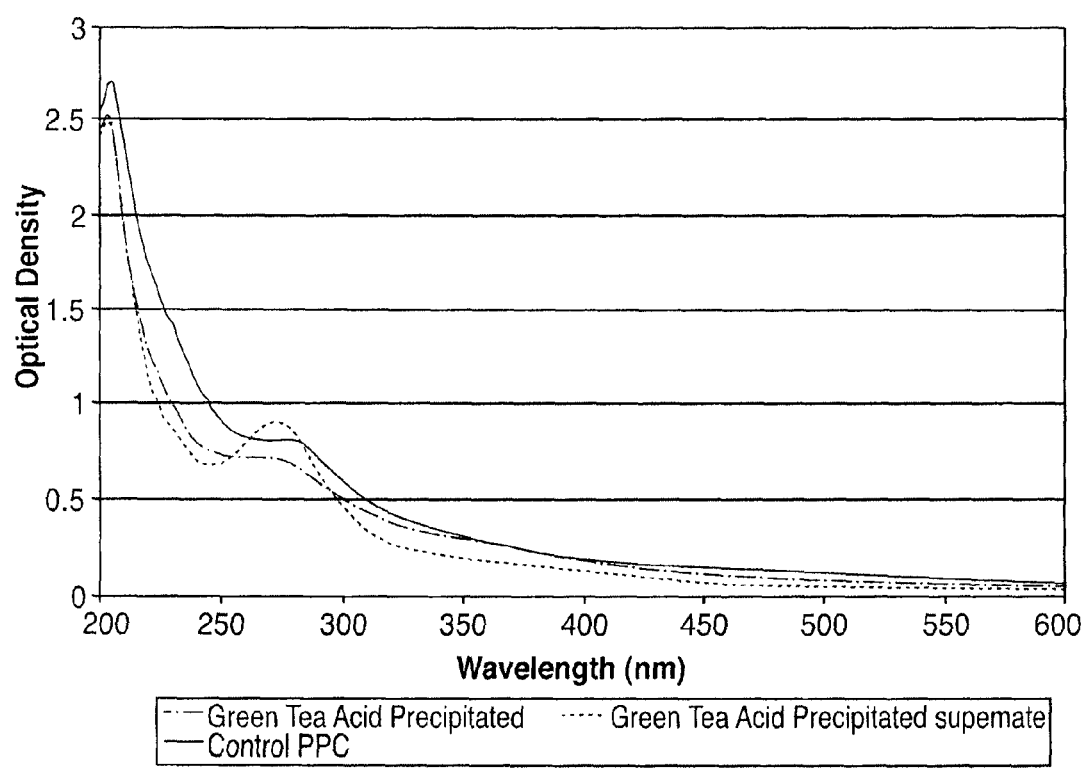
FIG. 17 shows the UV-visible absorption pattern of acid-precipitated GTX is similar to size-fractioned GTX.

The inventors also discovered that the GTX activity can be retrieved from a soluble fraction of acid-precipitated GTX. As seen in FIG. 17, the spectrum of acid-soluble GTX fraction was similar to the spectrum of <10 kDa GTX fraction, while the spectrum of acid-insoluble fraction was similar to the spectrum of >10 kDa GTX fraction.

Figure 18:
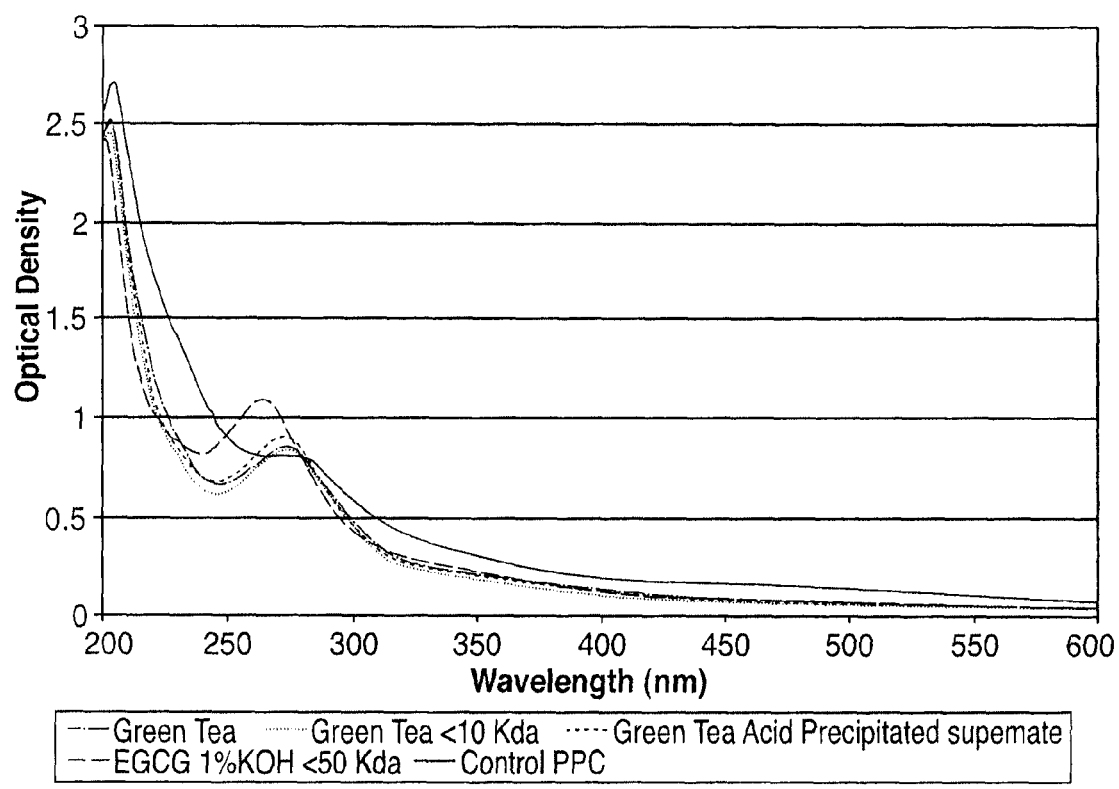
FIG. 18 shows the spectrum of alkaline-treated EGCG in comparison to spectra of PPC and GTX.
Figure 19:
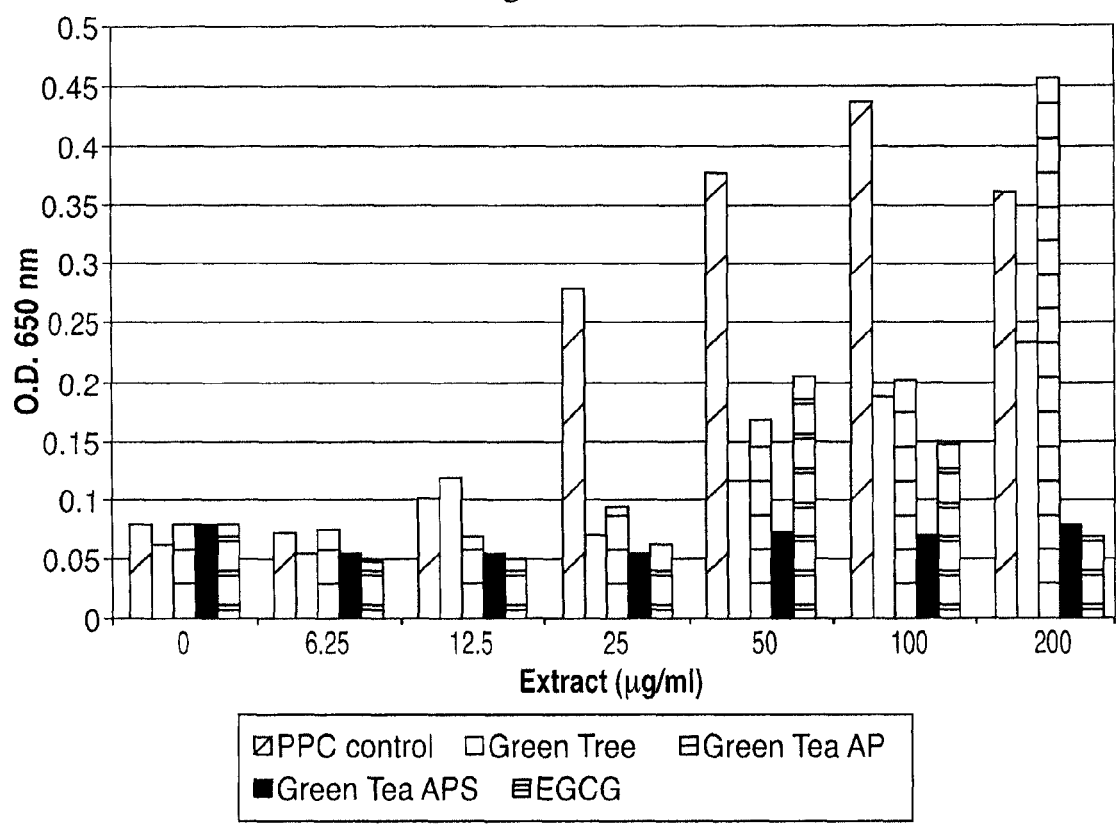
FIG. 19 shows adherence of human PBMCs 48 hours after treatment with PPC, GTX or EGCG.

Having noticed that the main polyphenol in green tea is epigallocatechin-3-gallate (EGCG), the inventors compared the spectrum of EGCG to spectra of PPC and GTX. FIG. 18 shows the spectrum of alkaline-treated EGCG is comparable to the spectrum of PPC, acid-soluble fraction of GTX and GTX>10 kDa fraction. The inventors then examined the effect of EGCG extract on adherence of human PBMCs in comparison to the effect of PPC and GTX and found that EGCG did not stimulate adherence of human PBMCs in the same way as PPC does (FIG. 19).

Example 16

Figure 20A:
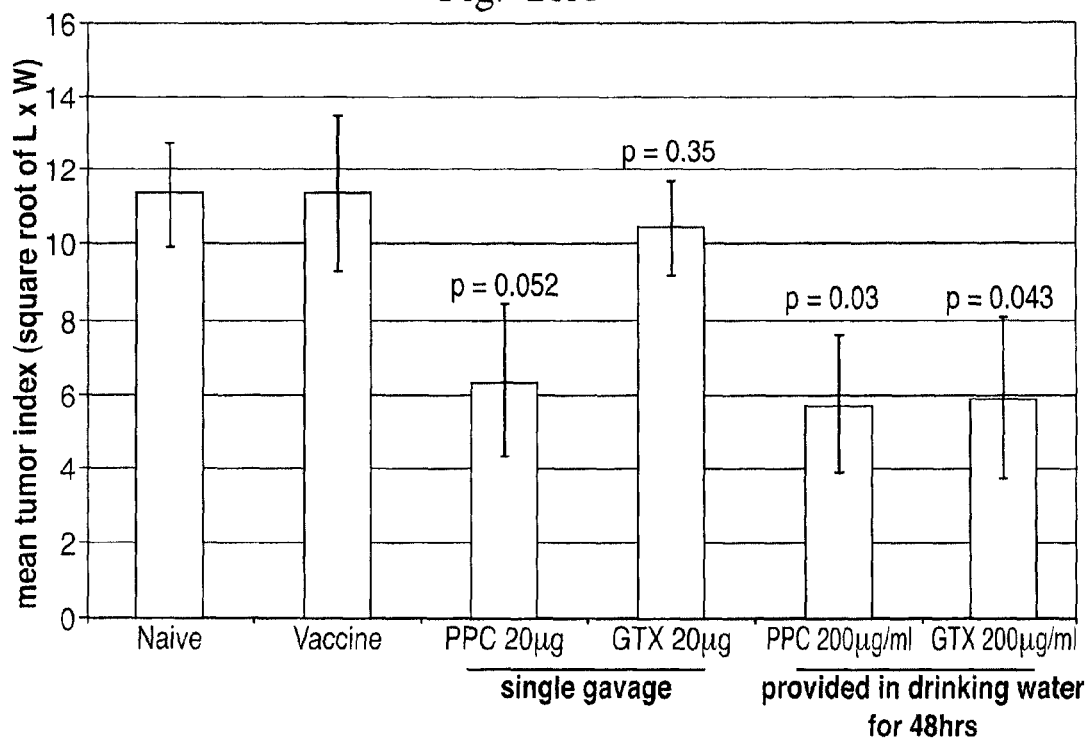
FIG. 20A shows mean tumor index 17 days post tumor challenge.

Extracts From Pine Cones and Green Tea Exhibit Similar Adjuvant Activity For an Anti-tumor DC Vaccine The inventors also examined the effect of GTX as a vaccine adjuvant. Specifically, mice (C57BI/6) were vaccinated by subcutaneous injection of 500,000 bone marrow-derived dendritic cells that had been pulsed with 10 µg/ml of the chicken ovalbumin peptide (SIINFEKL 258-265, Accession number NP 990483) just prior to injection. At the time of vaccination the mice were gavaged with 20 or 200 µg of PPC or GTX or were provided PPC or GTX at 200 µg/ml in their drinking water ad libitum. Seven days after vaccination the mice were challenged with $1 \times 10^6$ EG7.OVA injected subcutaneous. The rate of tumor growth was then monitored for 27 days using digital calipers. FIG. 20A shows mean tumor index for the following groups of mice 17 days post tumor challenge: mice challenged with tumor without vaccination (naïve), mice challenged with tumor and vaccinated with vaccine alone or vaccinated with vaccine and either with 20 µg/ml of PPC or 200 µg/ml of PPC (ad libitum), or 20 µg/ml of GTX or 200 µg/ml of GTX (ad libitum). P values were measured for vaccine versus treatment group. As seen in FIG. 20A, tumor growth was inhibited almost two-fold in mice vaccinated with a combination of vaccine and 200 µg/ml GTX in comparison to tumor growth in mice not vaccinated or mice vaccinated with the vaccine alone. Furthermore, the efficiency of GTX at 200 µg/ml for inhibiting tumor growth was comparable to that of PPC extract which also decreased the rate of tumor growth by two-fold.

Figure 20B:
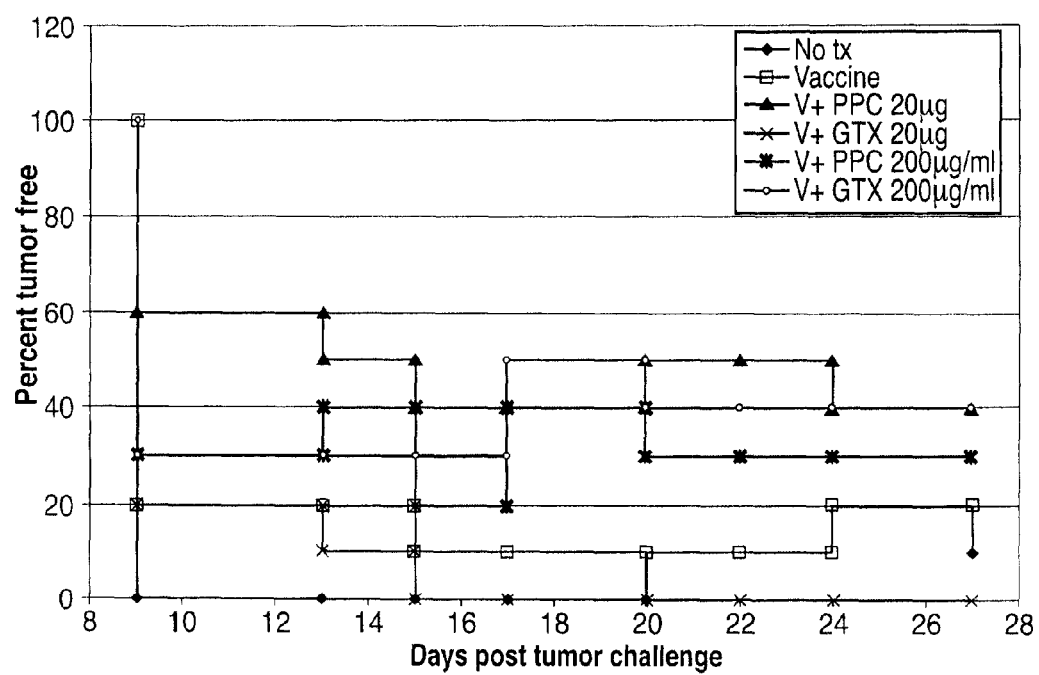
FIG. 20B shows number of tumor-free DC vaccinated C57BI/6 mice 27 days post challenge with $1 \times 10^6$ EG7.OVA cells.

The inventors also calculated the number of tumor-free DC vaccinated C57BI/6 mice at 27 days post challenge with $1 \times 10^6$ EG7.OVA cells and found that the number of mice that remained tumor-free 27 days post challenge was two-fold higher in the group vaccinated with a vaccine and 200 µg/ml GTX combination in comparison with a group vaccinated with vaccine alone (FIG. 20B).

Example 17

PPC Extracts Activate Immune Responses in an Animal Model

Mice were gavaged with 100 µl of water or 2 µg, 20 µg, 200 µg of PPC extract. Immediately thereafter, the mice were injected with 2 mg of FITC-labeled ovalbumin in 200 µl of PBS. Six hours later, spleens were isolated from the mice and splenocytes were purified by Ficoll gradient. Isolated splenocytes were then stained with APC-CD11c (DC marker) or -CD11b (macrophage marker).

Figure 21A:
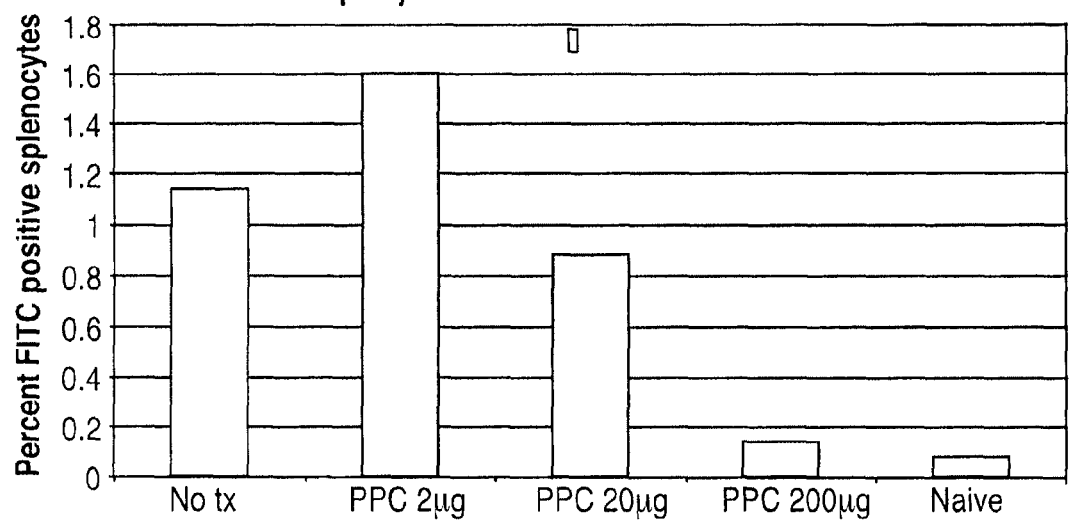
FIG. 21A shows effects of a single PPC gavage on the uptake of i.p. injected FITC labeled ovalbumin.
Figure 21B:
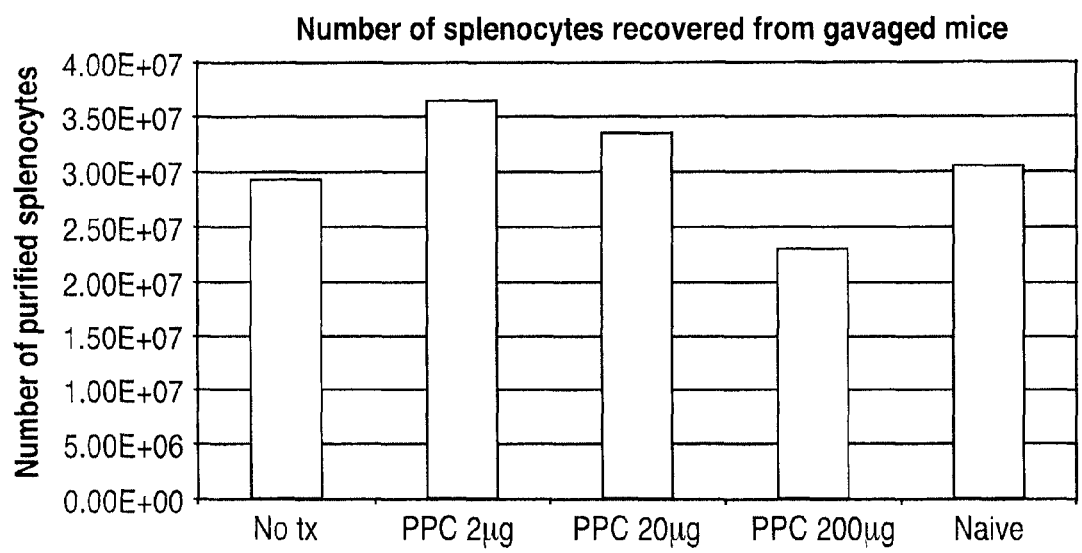
FIG. 21B shows number of splenocytes recovered from the gavaged mice of FIG. 21A.

FIG. 21A shows effects of a single PPC gavage on the uptake of i.p. injected FITC labeled ovalbumin. An increase in percentage of FITC positive splenocytes isolated from mice gavaged with 2 µg of PPC extract was observed in comparison with mice not gavaged with any PPC extract, suggesting that treatment with PPC extract stimulates splenocytes. FIG. 24B accompanies FIG. 24A and provides information with respect to the effects of different PPC concentrations on immune responses of the gavaged mice. As shown in FIG. 21B, there was an increase in the number of activated splenocytes in animals gavaged with 2 µg of PPC extract. However, there was a decrease in the number of activated splenocytes when concentration of PPC extract was increased to 200 µg.

Figure 21C:
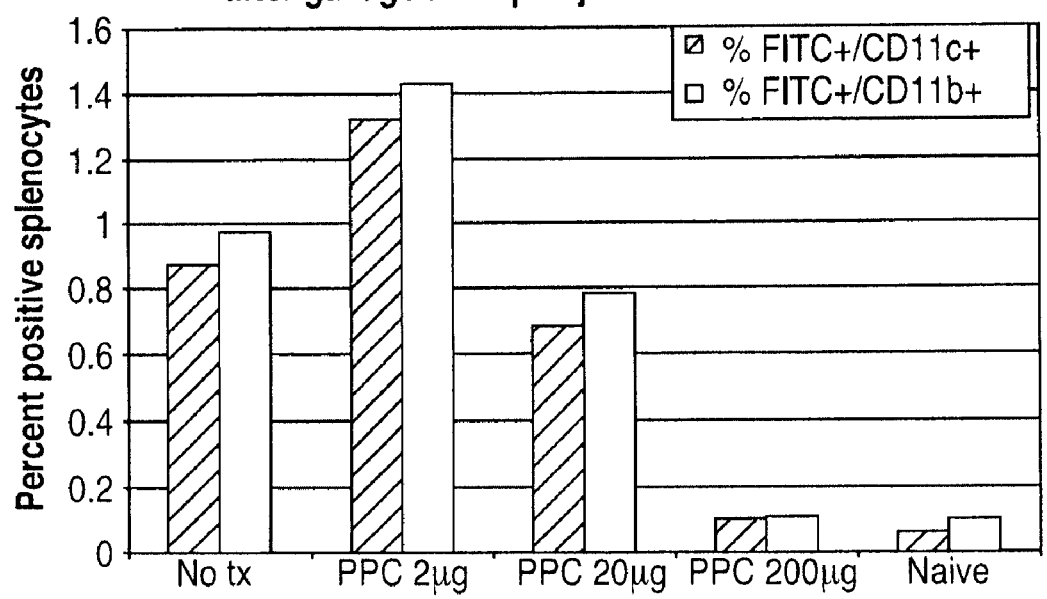
FIG. 21C shows phenotype of FITC+ splenocytes 6 hrs after gavage and i.p. injection of FITC-OVA.

FIG. 21C is a diagram showing percentage of CD11c$^+$ and CD11b$^+$ cells in populations of splenocytes isolated from mice treated with different concentrations of PPC extract. In agreement with data reported in FIGS. 21A and 21B, FIG. 21C shows that there were approximately two times more of activated CD11c$^+$ and CD11b$^+$ splenocytes in mice gavaged with 2 µg of PPC extract when compared to mice not gavaged with PPC extract.

Example 18

Mice Vaccinated with a Combination of PPC Extract and Anti-Tumor DNA Vaccine are Less Susceptible to Developing Tumors than Mice Immunized with the Vaccine Alone To examine whether PPC extract can function as a vaccine adjuvant for a DNA vaccine in an animal model, C57BI/6 mice (10 per group) were vaccinated with either vaccine alone, 2 injections into the calf muscle each containing 50 µg of the plasmid DNA, pzOVA, in 50 µl of phosphate buffered saline or a combination of vaccine and gavage with different concentrations of PPC: 2 µg, 20 µg or 200 µg. The control group of mice was gavaged with 200 µg of the PPC extract without vaccination. Sixteen days later the mice were challenged with $3 \times 10^6$ EG7.OVA tumor cells and monitored for development of tumors. The results of these studies are shown in FIG. 22A.

Figure 22A:
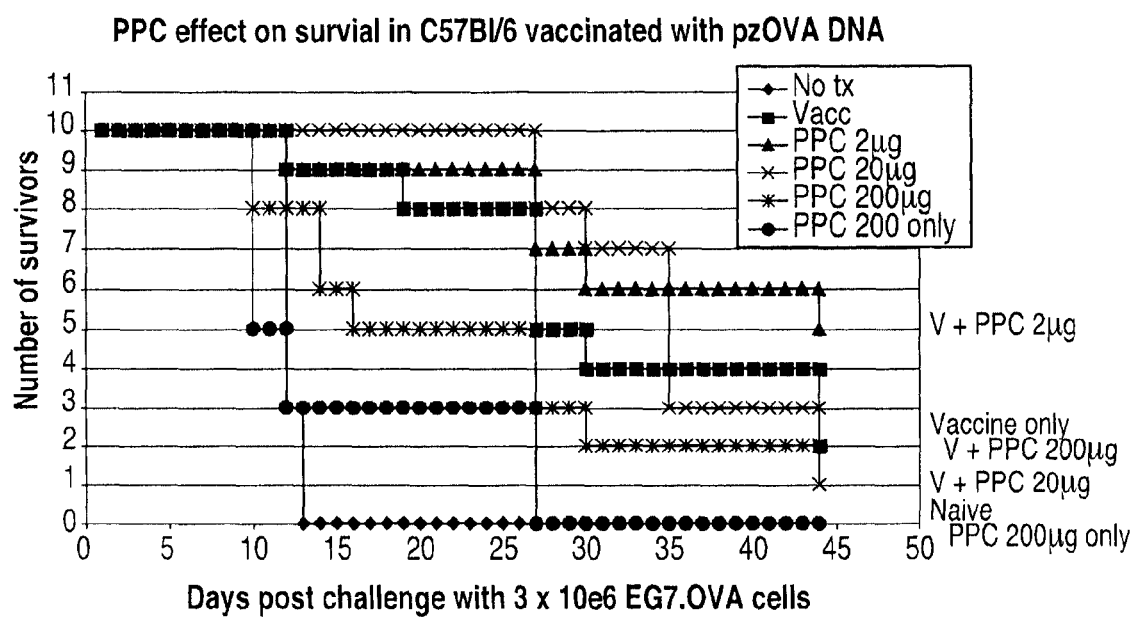
FIG. 22A shows number of mice with EG7.OVA tumors.

As seen in FIG. 22A, by day 27 post-tumor challenge, all ten mice in the No Treatment and PPC 200 µg only groups had developed tumors. At this same time 7 mice in the PPC 200 µg+Vaccine group, 5 mice in the Vaccine only group, 3 mice in the PPC 2 µg+Vaccine group, and only 2 mice in the PPC 20 µg+Vaccine group had developed tumors.

Figure 22B:
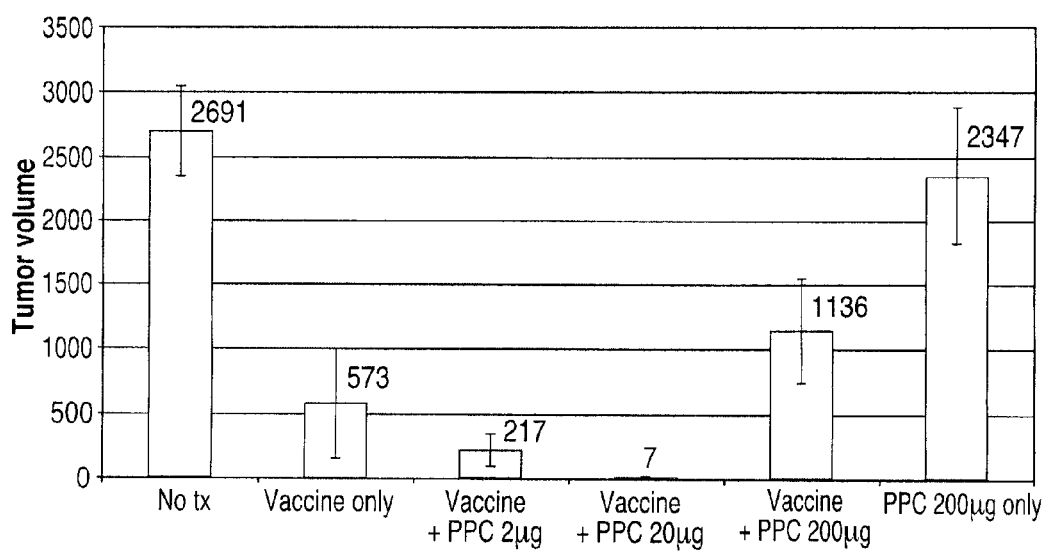
FIG. 22B shows day 12 tumor volumes: C57BI/6 vaccinated with pzOVA then challenged 16 days later with EG7.OVA tumor cells.

The effect of PPC extract on tumor volume was also studied. As shown in FIG. 22B, by day 12 post tumor challenge, mice that were not vaccinated developed tumors that were on average five times larger than tumors in mice that were vaccinated with the vaccine alone. Furthermore, tumor volumes in mice vaccinated with the vaccine and 2 µg of PPC extract were at least two times smaller than the volumes of tumors from mice vaccinated with the vaccine alone. These data suggest that PPC extract exhibits an anti-tumor activity when administered with vaccine.

The effect of PPC extract on survival of immunized and challenged mice was also studied. Results are shown in FIG. 22C. As can be seen, at day thirty post-challenge, none of the ten mice survived in a control group which was not vaccinated prior to a challenge with tumor cells and no mice survived in a group gavaged with PPC alone. Moreover, four out of ten mice survived in the group vaccinated with the vaccine alone and seven out of ten mice survived in a group immunized with a combination of vaccine and 2 µg of PPC extract. In summary, these data show that PPC extract improves outcomes and exhibits anti-tumor activity when combined with a vaccine.

Example 19

Serum Amyloid Protein (SAP) Inhibits PPC-induced Adherence of Total Human PBMC Human PBMC were plated in a 96-well plate at a concentration of $1\times10^6$/ml in AimV serum-free media (Invitrogen/BRL). Cells were incubated either with PPC extract alone (at 9 μg/ml, 6.25 μg/ml, 12.5 μg/ml, 25 μg/ml, 50 μg/ml, 100 μg/ml, 200 μg/ml or 400 μg/ml) or with PPC extract (at 9 μg/ml, 6.25 μg/ml, 12.5 μg/ml, 25 μg/ml, 50 μg/ml, 100 μg/ml, 200 μg/ml or 400 μg/ml) and 10 μg/ml of SAP.

Figure 23:
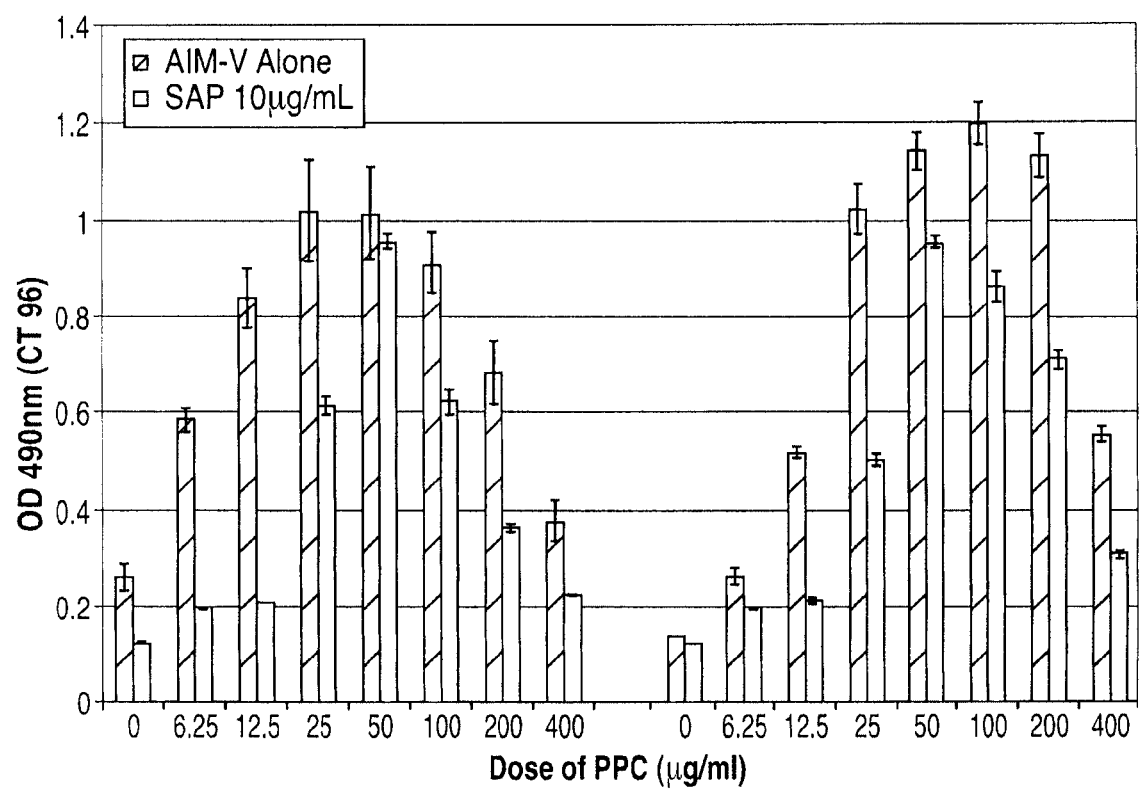
FIG. 23 shows ability of serum amyloid protein (SAP) to inhibit the PPC-induced adherence of hPBMC. Data from two different donors are shown.

Seventy two hours later, non-adherent cells were removed and the effects of PPC extract and SAP on cell adherence were measured by absorbance at 490 nm. As seen in FIG. 23, SAP inhibited the PPC-induced adherence, suggesting that both the active components of PPC extract and SAP may assert their effects on mononuclear cells via the same pathway by interacting with FcγR.

Example 20

IL-8 Production by PBMC Exposed to PPC for 24 Hours in AimV or RPMI/10% FCS Human PBMC were plated in a 96-well plate at a concentration of $1\times10^6$/ml in 200 μl in either in AimV serum-free media or in RPMI with 10% heat-inactivated fetal calf serum (Hyclone). Cells were then incubated with 25 μg/ml, 50 μg/ml or 100 μg/ml of PPC extract for 24 hours. IL-8 production by the cells was then measured in ELISA assay using the Human IL-8 ELISA development kit from PeproTech. The wells of a Maxisorp 96 well plate was coated with capture antibody by adding 100 μl of 0.5 μg/ml capture antibody and incubating the plate in the refrigerator overnight. After the overnight incubation the wells were blocked with 1% BSA in phosphate buffered saline for 1 hour at room temperature and then washed with PBS/0.05% Tween-20. The standards and PBMC culture supernatants were added to the appropriate wells and incubated for 2 hours at room temperature. The wells were then washed and 100 μl of biotinylated detection antibody (0.25 μg/ml) was added and incubated for 2 hours at room temperature. Next, 100 μl of a 1:100 dilution of streptavidin peroxidase (KPL, Inc) was added and incubated at room temperature for 30 minutes. The wells were washed extensively and then 100 μl of KPS's Sure Blue TMB-1 was added to each well. The reaction was stopped by adding 100 μl of 0.6N sulfuric acid. The absorbance at a wavelength of 450 nm was measured and the levels of IL-8 determined from the standard curve.

Figure 24:
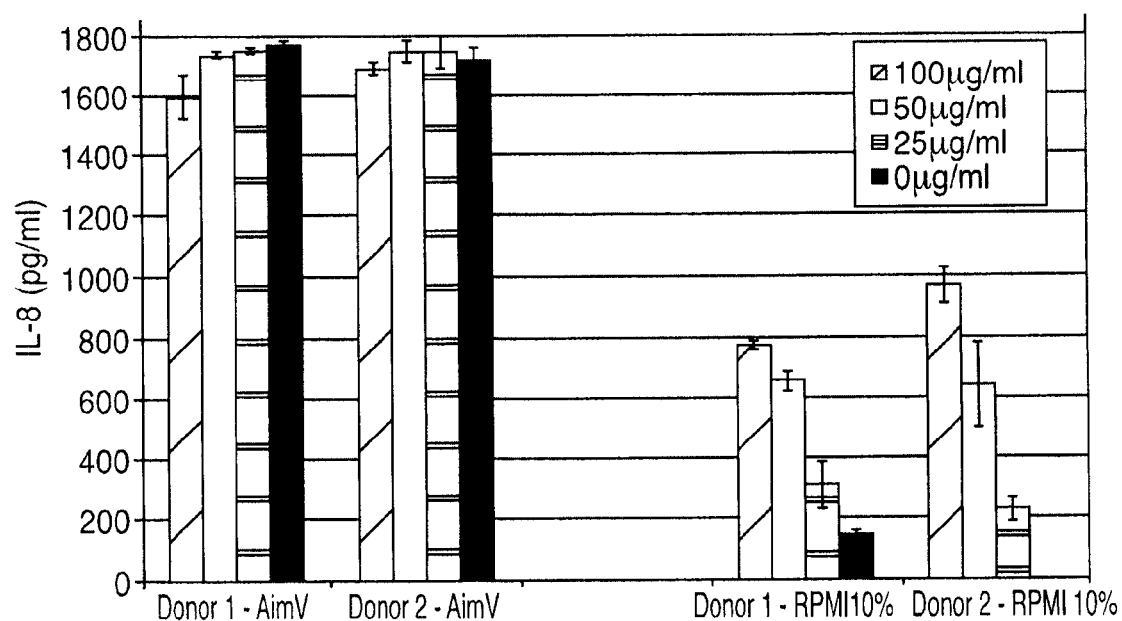
FIG. 24 shows IL-8 production by PBMC exposed to pine cone extract for 24 hours in AimV or RPMI/10% FCS.

As seen in FIG. 24, in the absence of serum, PPC does not affect the high background level of IL-8 production (diagrams donor 1—AimV and donor 2—AimV). However, when human PBMC are grown in the presence of serum, PPC overcomes the serum-associated inhibition of IL-8 production in a dose-dependent manner (FIG. 24, diagrams donor 1—RPMI/10% FCS and donor 2—RPMI/10% FCS).

Example 21

PPC Induces Development of IFN-Alpha Producing Myeloid Dendritic Cells

Human PBMC were isolated from adult donors and cultured with serum and in the presence of either GM-CSF/IL4 or PPC (12.5 and 50 μg/ml). After 4 days of culture, the cells were stimulated with the TLR ligands, LPS (TLR4), poly Inosine:Cytosine (pI:C) (TLR3) and PAM3Cys (TLR2). Following 2 additional days of culture, the culture supernatants were assayed for IL12 and IFN-alpha production by enzyme-linked immunosorbent assay (ELISA).

Figure 25A:
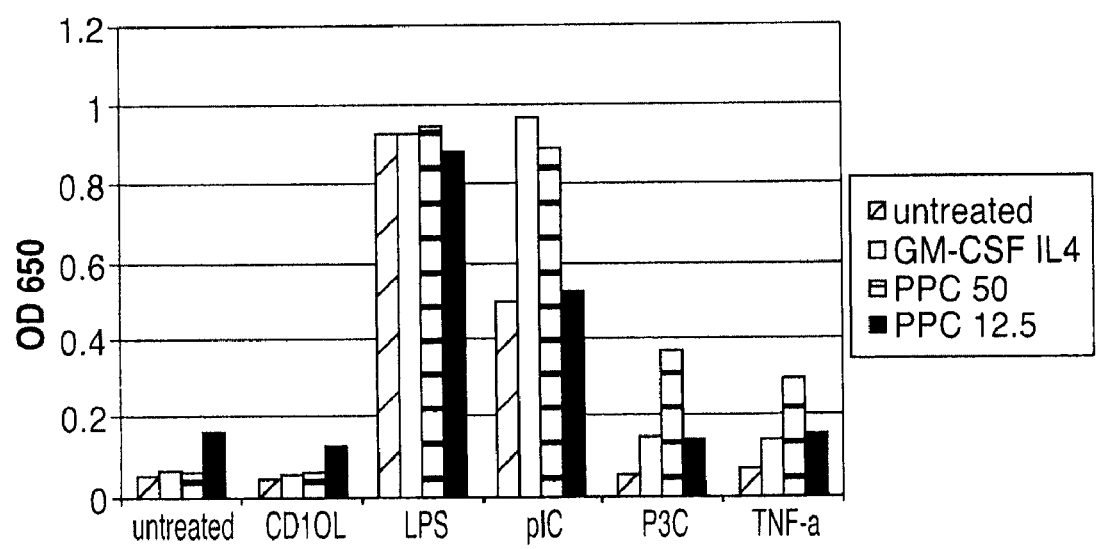
FIG. 25A shows IL12 production in response to TLR ligands and DC maturation factors. The DCs were cultured as described in the text under the indicated primary culture conditions (legend, right), followed by an additional 2 days of culture with the indicated stimuli. The supernatants were assayed for IL12 by ELISA as described. Similar results were obtained in four independent experiments.
Figure 25B:
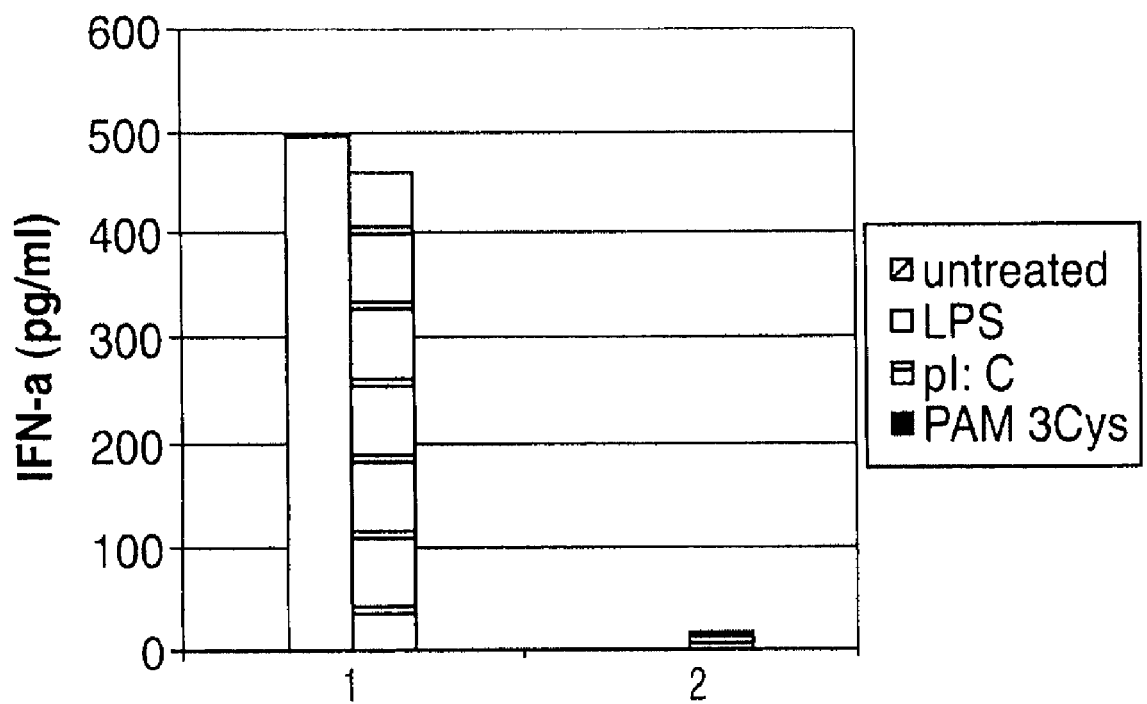
FIG. 25B shows TLR ligands stimulate IFN-alpha production by PPC-DCs. PPC-DCs (1) and GM/IL4-DCs were cultured as described in the text for 4 days. The cells were then stimulated with the indicated ligands for 48 hrs. The culture supernatants were assayed for IFN-alpha by ELISA. Similar results have been obtained in two independent experiments.

IL12 production was stimulated by all three ligands under all three primary culture conditions (FIG. 25A). PAM3Cys-induced IL12 production was most substantial for the PPC-DCs, suggesting a more active TLR2 pathway in the latter cell-type. Interestingly, the LPS and pI:C treatments both stimulated IFN-alpha production in PPC-DCs, but not in the untreated or GM-CSF/IL4-derived mDCs (FIG. 25B). Moreover, no IFN-alpha was produced in response to PAM3Cys, consistent with the known signaling pathway of the TLR2 protein. These data have important implications for DC therapy employing PPC-DC.

Example 23

Activity of Pine Cone Extract in a Whole Cell Anti-Tumor Vaccine

This example illustrates the effectiveness of the pine cone extract of the present invention in a whole cell anti-tumor vaccine. Balb/c mice were vaccinated by subcutaneous injection with $5\times10^5$ mitomycin C treated CT26.CL25 tumor cells.

Figure 26A:
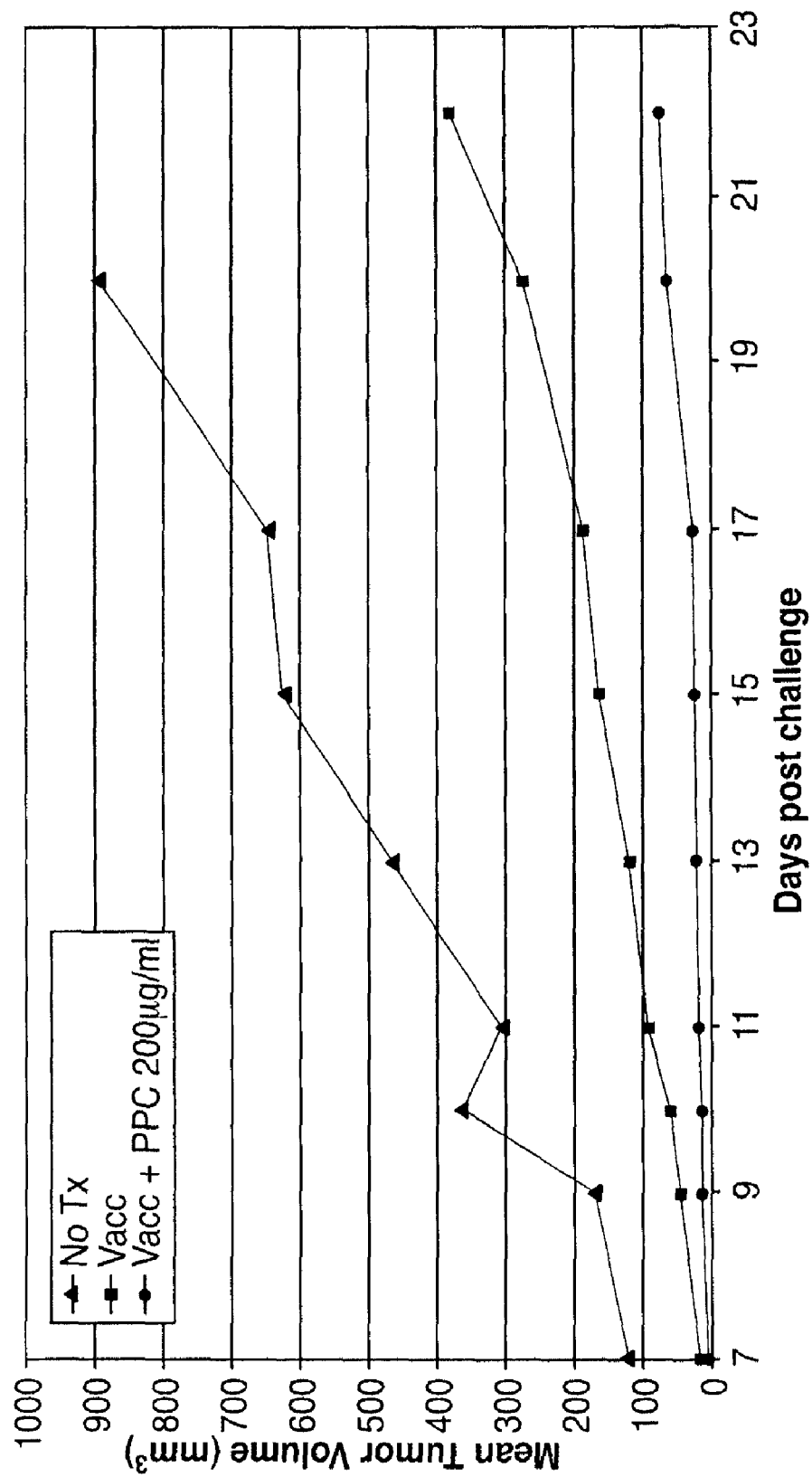
FIG. 26A shows effect of vaccine, pine cone alkaline extract, and combinations thereof, on tumor volume subsequent to s.c. injection of a whole cell tumor vaccine and subsequent challenge with live tumor cells.

Beginning immediately after vaccination, pine cone extract was provided in water for 16 hours continuously at a concentration of 200 μg/ml to one group of mice while another group received the vaccine only and one group received neither of the vaccine or PPC. Mice were challenged with live tumor cells at seven days post-vaccination. As shown in FIG. 26A, compared to vaccine alone, tumor volume in mice that were vaccinated and administered 200 μg/ml pine cone extract of the present invention was essentially zero.

This example also shows that the immunity produced when the pine cone extract of the present invention has a long effect, showing that the pine cone extract does not interfere with the development of antigen-specific memory response. As shown in FIG. 26B mice that failed to develop tumors after the initial challenge also failed to develop tumors after being challenged with $8\times10^5$ tumor cells on Day 43 post-initial tumor challenge and again with $1.6\times10^6$ tumor cells on Day 68 post-initial tumor challenge. The finding that mice who received PPC during the vaccination prevented establishment of tumors following these further challenges shows that PPC does not prevent the establishment of a vaccine-induced immunologic memory.

Example 24

Adjuvant Activity of Pine Cone Extract in an In-Situ Vaccine

This example shows that the pine cone extract of the present invention can be a potent adjuvant for pre-existing immunogens, for example weakly immunogenic or nonimmunogenic tumors, where the release of pre-existing in situ immunogen is promoted by a suitable treatment, such as chemotherapy, radiotherapy, or electrochemotherapy.

Figure 27A:
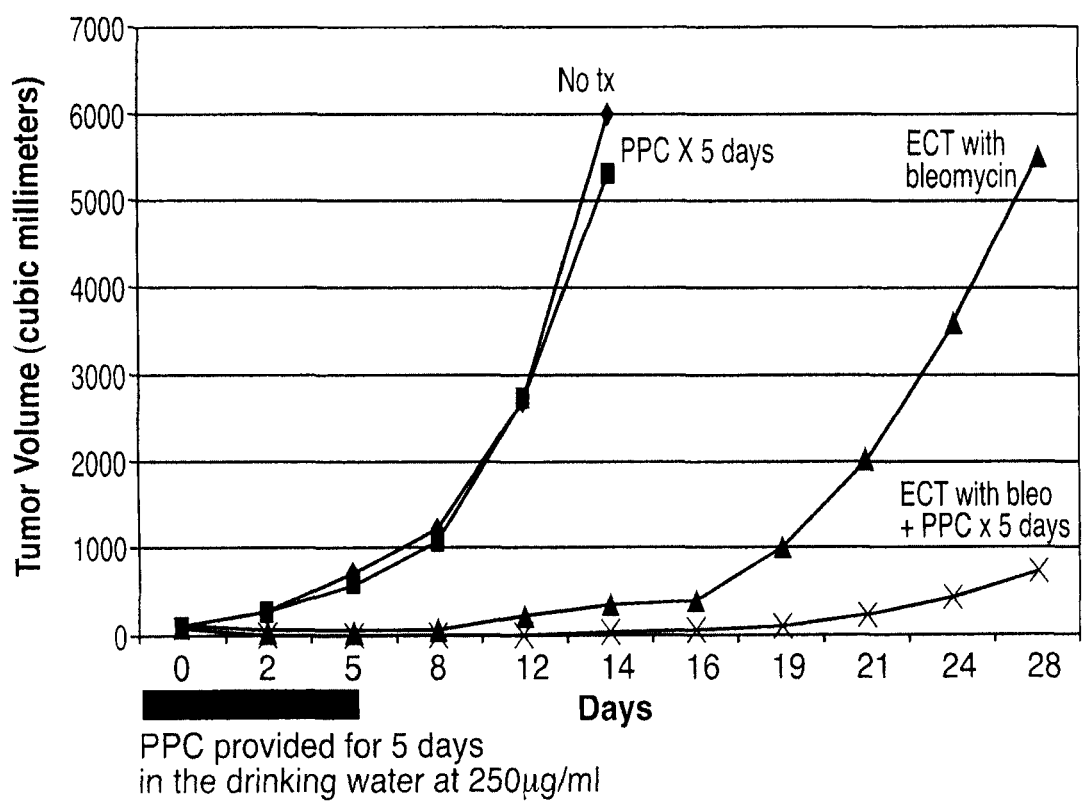
FIG. 27A shows suppression of melanoma tumor volume by combined electrochemotherapeutic delivery of bleomycin and pine cone alkaline extract adjuvant.

Subcutaneous melanoma was established in C75B1/6 mice by subcutaneous injection with B16-F10 cells, which are highly metastatic and have very low immunogenicity. Once the tumors were palpable, mice were treated by electro-chemotherapy comprising intratumor injection with bleomycin followed by electrical stimulation essentially as described in U.S. Pat. Nos. 5,702,359; 6,418,341; 6,451,002; 6,569, 149; and 6,714,816, which are hereby incorporated by reference herein. Pine cone extract was provided to the appropriate mice groups in their drinking water at a concentration of 200 μg/ml for five days post electrochemotherapy. As shown in FIG. 27A pine cone extract alone did not decrease tumor cell volume compared to untreated mice. Electrochemotherapy alone suppressed tumor volume, but melanoma tumor volume was markedly reduced in mice also provided with pine cone extract.

Figure 27B:
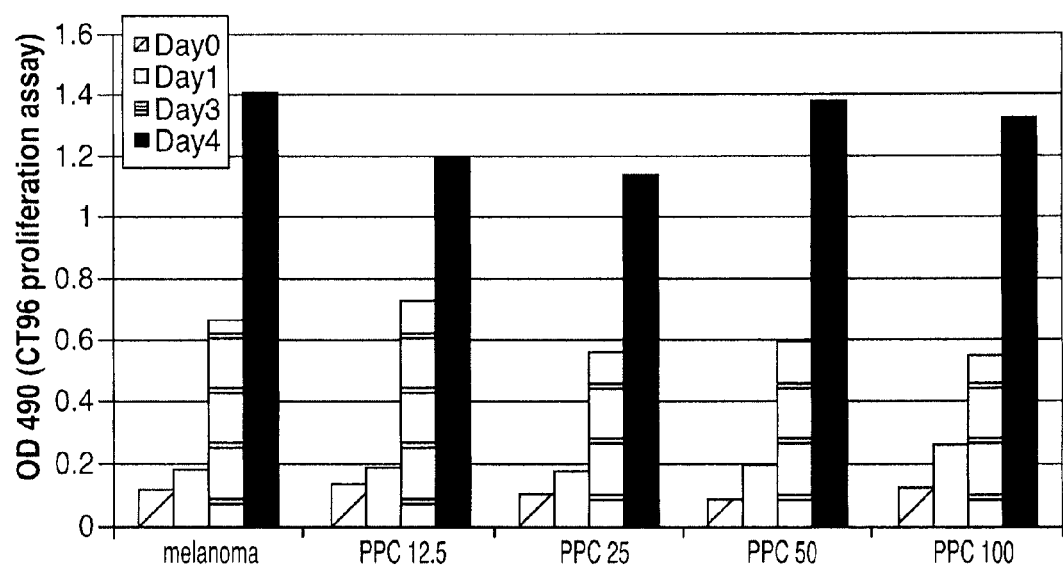
FIG. 27B shows failure of pine cone extract to affect growth of melanoma tumor cells in vitro.

In vitro cell grown of this melanoma cell line was not significantly affected by the pine cone extract of the present invention at concentrations up to at least 100 μl/ml (FIG. 27B).

Example 25

Pine Cone Extract is not a Broadly Acting T-Cell Mitogen

This example shows that oral delivery of the pine cone extract of the present invention does not cause non-specific activation of T-cells. Balb/c mice were gavaged with 10 μg of the pine cone extract of the present invention and then injected i.p. with 25 μg of an IFNγ capture antibody. A control group of mice was injected with anti-CD3E antibody, a known T-cell mitogen. After 6 hours, serum was collected and analyzed for anti-IFNγ/IFNγcomplexes by ELISA (FIG. 28). Pine cone extract alone was essentially devoid of non-specific T-cell mitogenic activity.

Example 26

Pine Cone Extract Enhances Cytotoxic T-Lymphocyte (CTL) in the Primary Response

Pine cone extract increases the number of CTL detected in memory, or secondary, responses. This example shows that pine cone extract significantly increases the primary response to the vaccine, accounting for at least part of the observed increase in memory responses.

Figure 29:
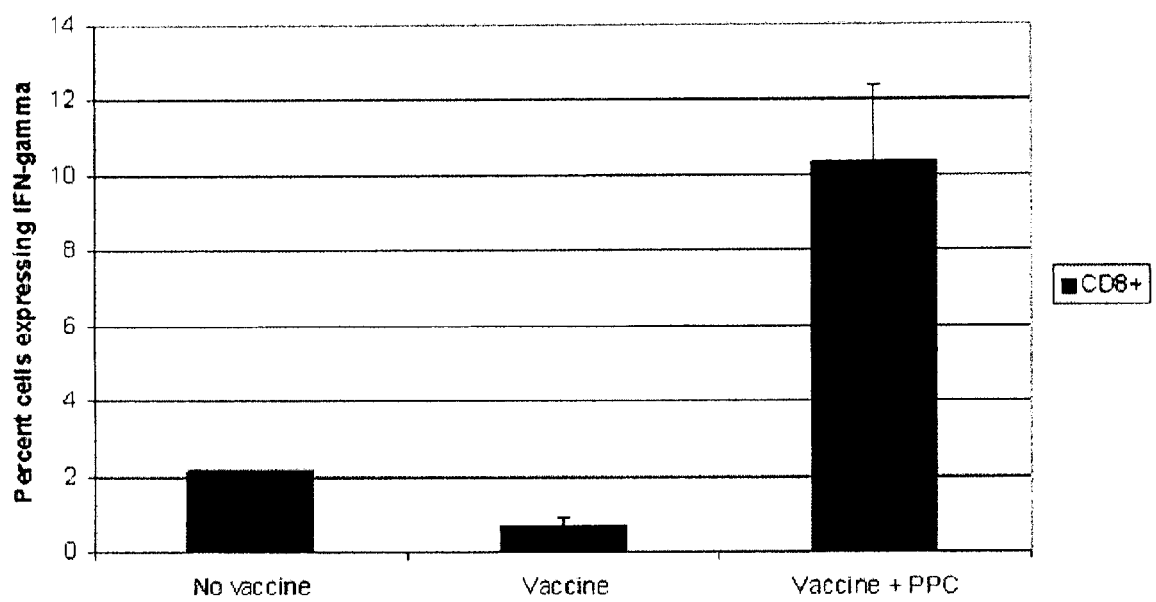
FIG. 29 shows effect of a single oral dose of pine cone extract on the number of CD8+ splenocytes producing intracellular IFN-γ in splenocyte culture stimulated for four days with a vaccine antigen-specific β-galactosidase peptide.

Mice were vaccinated with mitomycin C treated CT26.C125 cells expressing β-galactosidase. Splenocytes were obtained from mice vaccinated seven days earlier and still in their primary response. Four day cultures were stimulated with a β-galactosidase peptide and intracellular IFNγ production by CD8+ cells was assessed (FIG. 29). A single oral dose of the pine cone extract of the present invention significantly enhanced the number of CD8+ splenocytes producing intracellular IFNγ, showing an increase in CTL due to pine cone extract administered during the primary response.

Example 27

Evaluation of PPC as an Adjuvant for a Model Protein Vaccine

A study was conducted to determine whether orally administered PPC functions as an adjuvant for a model protein vaccine. Seven groups of female BALB/c mice, approximately 6 weeks old, were randomized to one of 7 groups (n=5 per group). The study groups are shown in Table 7.

TABLE 7

Study Group Overview

| Group | Treatment |
|---|---|
| 1 | Naïve (no vaccine) |
| 2 | Vaccine + gavage with water |
| 3 | Vaccine + gavage with 2 μg PPC |
| 4 | Vaccine + gavage with 20 μg PPC |
| 5 | Vaccine + gavage with 200 μg PPC |
| 6 | Vaccine + gavage with 200 μg imiquimod |
| 7 | Vaccine + 200 μg /ml PPC in drinking water ad labitum |

Mice were immunized by subcutaneous injection of 100 μg of whole ovalbumin (OVA) protein on day 0 (prime) and day 14 (boost). Immediately following immunization the mice were gavaged with 100 μl water, or with water containing PPC at 2, 20 or 200 μg. As a positive control, one group of mice was gavaged with 200 μg of imiquimod (R837) at the time of immunization. Another group of mice received PPC 200 μg/ml ad labitum in their drinking water over the entire 21 days of the study. On day 21, serum levels of OVA specific IgG1 and IgG2a were determined by ELISA.

To perform the ELISA, Maxisorp plates were coated with 100 mg/ml OVA, respectively, for about 1.5 hours and maintained at 37° C. Plates were washed three times with buffer and then blocked with Super Blocking Buffer in TBS (Pierce, Rockford, Ill.) containing Tween for about 1 hour at 37° C. Serum samples were serially diluted fourfold in buffer, added to the plates and incubated overnight at 4° C. Plates were washed three times with buffer and incubated with 100 ml of a 1/2000 dilution of HRP-conjugated anti-IgG1 or IgG2a detection antibody for 2 h at room temperature. The plates were then washed with buffer and developed with TMB peroxidase substrate for 10-30 minutes at room temperature. The reaction was stopped and absorbance at 450 nm was determined using a MicroQuant plate spectrophotometer. The titer for each sample was presented as the dilution that gives an absorbance 0.5 IgG2a and IgG1 data were represented as mean values of individual mice per group±standard deviation of the mean.

Figure 30:
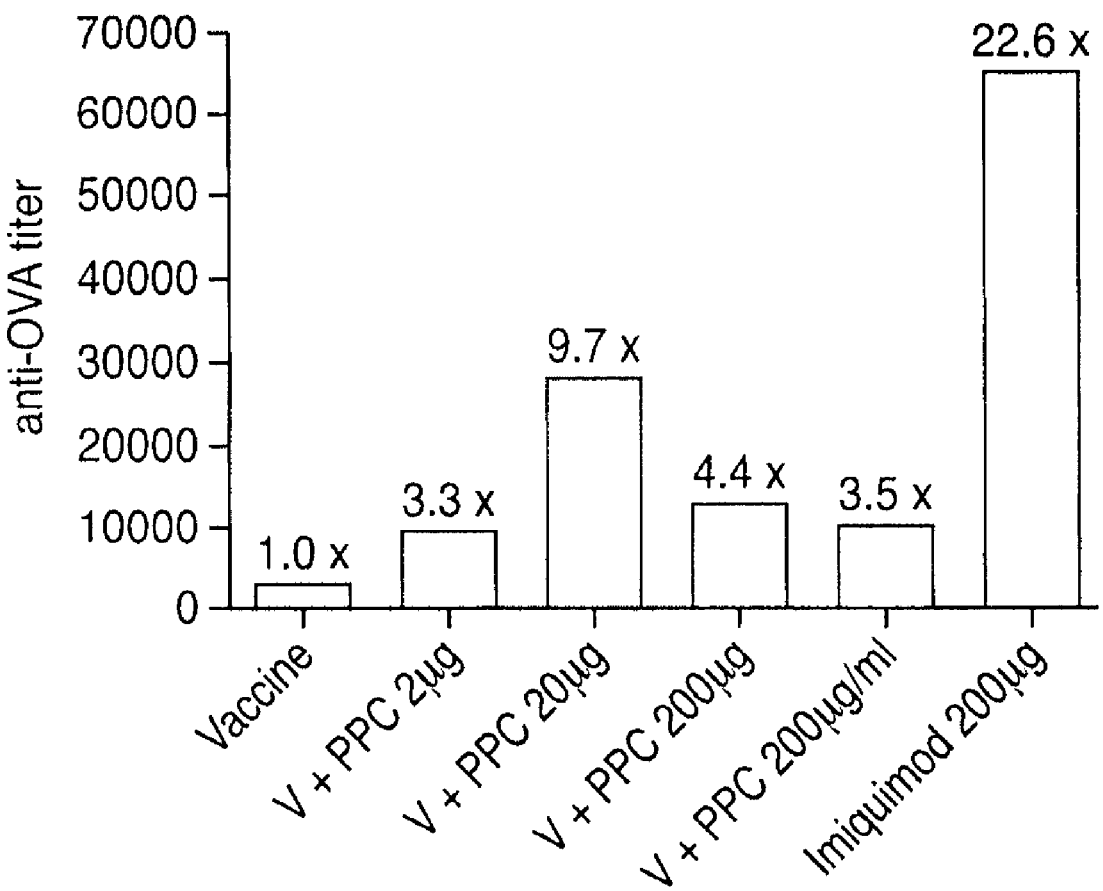
FIG. 30 shows that at all doses, PPC enhanced production of OVA-specific IgG2a antibodies.

As shown in FIG. 30, PPC at all doses enhanced production of OVA-specific IgG2a antibodies. Gavage with 20 μg PPC was the optimal dose of PPC in this experiment. Imiquimod greatly enhanced OVA-specific IgG2a levels. These results suggest that PPC boosts Th1 mediated vaccine responses.

Figure 31:
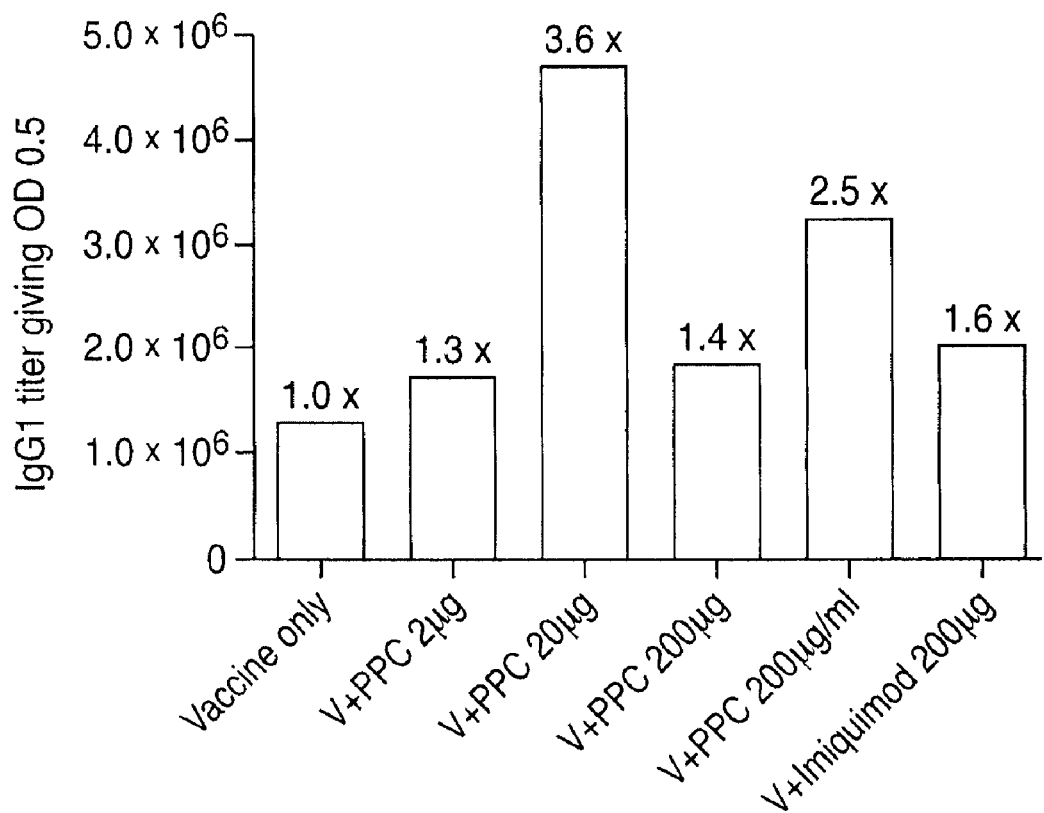
FIG. 31 shows that PPC gavage with 20 µg at the time of both primary and boost immunizations, or continuous delivery of 200 µg PPC enhanced serum levels of OVA-specific IgG1 antibodies.

As shown in FIG. 31, PPC gavage with 20 μg (but not 2 or 200 μg) at the time of both primary and secondary immunizations, or continuous delivery of 200 μg ml PPC enhanced serum levels of OVA specific IgG1 antibodies. Imiquimod did not affect IgG1 levels.

Figure 32:
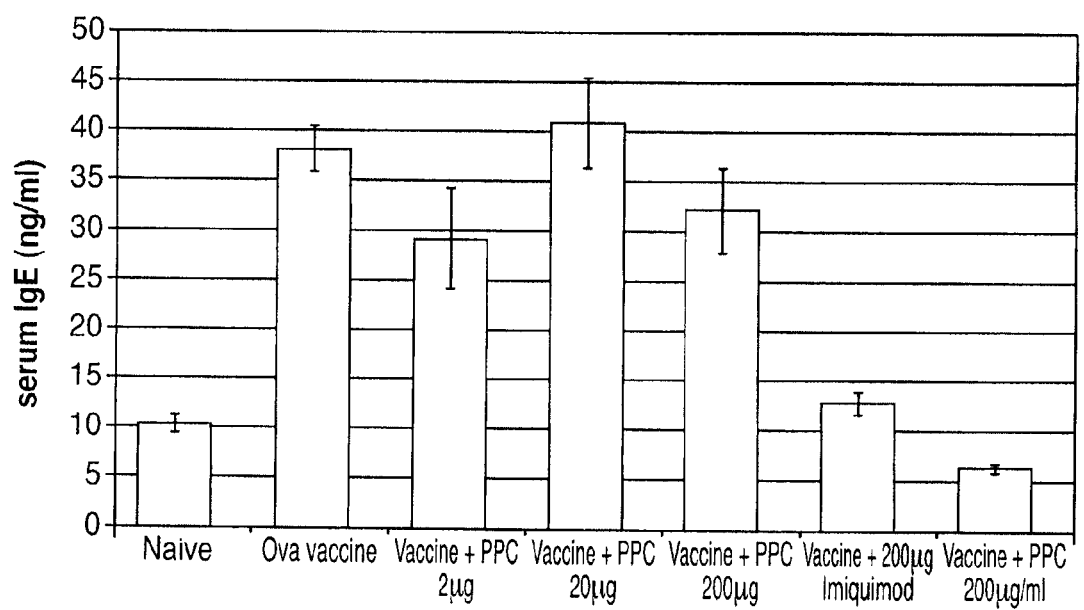
FIG. 32 shows PPC gavages (all doses) did not affect serum levels of IgE. Continuous delivery of 200 µg/ml PPC suppressed production of IgE antibodies.

As shown in FIG. 32, PPC gavages (all doses) did not affect the serum levels of IgE (total, OVA specific not measured). Continuous delivery of 200 μg/ml PPC suppressed production of IgE antibodies. Imiquimod suppressed the vaccine induced levels of IgE. Therefore, a while a single dose did not affect IgE levels in this model, continuous delivery did and could be important for use in allergic patients.

Example 28

Evaluation of PPC in C57Bl/6 Mice

C57Bl/6 mice were vaccinated with OVA (day 0) and provided PPC as a single gavage or continuously at 200 mg/ml according to the protocol in Example 27. Immediately following immunization the mice were gavaged with 100 μl water, or with water containing PPC at 2, 20 or 200 μg. Mice were given a booster immunization at day 14. Two weeks post delivery of the booster immunization, mice were challenged with 1 million EG7 OVA cells T cell lymphoma expressing OVA). A strong correlation was observed between the titers of antibodies generated in the protein vaccine protocol and the size of the tumors developing in the mice. Results are shown in Table 8.

TABLE 8

Correlation between PPC-associated Generation of Anti-OVA IgG1 and OVA-expressing Tumor Development.

| Treatment | Day 19 Tumor Size | IgG1 titers relative to vaccine only |
|---|---|---|
| OVA vaccine | 1398.7 | 1 |
| Vaccine + PPC 2 μg | 1325.0 | 1.3 |
| Vaccine + PPC 20 μg | 3009.8 | 3.6 |
| Vaccine + PPC 200 μg | 1368.3 | 1.4 |
| Vaccine + PPC Ad Labitum (200 μg/ml) | 1725.2 | 2.5 |

| | tumor size | IgG1 titer |
|---|---|---|
| Correlation Excludes OVA vaccine only | | |
| tumor size | 1 | |
| IgG1 liter | 0.96 | 1 |
| Correlation Includes OVA vaccine only | | |
| tumor size | 1 | |
| IgG1 titer | 0.94 | 1 |

These results suggest that when delivered along with a protein vaccine, PPC enhances the TH2/humoral response.

What is claimed is:

1. A method for suppressing the production of IgE antibodies in a vertebrate with elevated IgE levels comprising administering to the vertebrate a plant extract obtained by
    a) heat extracting, at a temperature of about 80° C. or above, defatted ground plant material with an alkaline solution comprising an alkaline agent;
    b) removing particulate matter with an average particle size greater than 0.2 μm and leaving a supernatant;
    c) adjusting pH of the resulting supernatant to about 6.0 to about 8.0;
    d) filtering the supernatant resulting from step c) to obtain a retentate fraction;
    e) drawing off the retentate fraction and removing particles with an average molecular mass of less than 10 kDa; and
    f) suspending the retentate fraction resulting from step e) in an aqueous solvent having a pH of about 6 to about 8 comprising alkaline agent.

2. The method of claim 1 wherein said extract comprises potassium.

3. The method of claim 1 wherein said elevated IgE levels are caused by exposure to an allergen.

4. The method of claim 1 wherein the extract is administered orally.

* * * * *